(12) United States Patent
Bocian et al.

(10) Patent No.: US 6,381,169 B1
(45) Date of Patent: Apr. 30, 2002

(54) HIGH DENSITY NON-VOLATILE MEMORY DEVICE

(75) Inventors: David F. Bocian, Riverside; Werner G. Kuhr, Oak Hills, both of CA (US); Jonathan S. Lindsey, Raleigh, NC (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/346,228

(22) Filed: Jul. 1, 1999

(51) Int. Cl.[7] .............................................. G11C 13/00
(52) U.S. Cl. ...................................... 365/151; 365/153
(58) Field of Search .................................. 365/151, 153

(56) References Cited

U.S. PATENT DOCUMENTS

| | | |
|---|---|---|
| 3,833,894 A | 9/1974 | Aviram et al. |
| 4,663,270 A | 5/1987 | Potember et al. |
| 4,670,860 A | 6/1987 | Wilson |
| 4,781,443 A * | 11/1988 | Giles .......................... 350/357 |
| 5,010,451 A | 4/1991 | Ueyama et al. |
| 5,016,063 A | 5/1991 | Beratan et al. |
| 5,035,835 A | 7/1991 | Asakawa et al. |
| 5,063,417 A | 11/1991 | Hopfield |
| 5,075,738 A | 12/1991 | Matsuda et al. |
| 5,135,637 A | 8/1992 | Eida et al. |
| 5,222,060 A | 6/1993 | Kuroda et al. |
| 5,252,698 A | 10/1993 | Bhardwaj et al. |
| 5,264,876 A | 11/1993 | Kawade et al. |
| 5,312,896 A | 5/1994 | Bhardwaj et al. |
| 5,432,379 A | 7/1995 | Eguchi et al. |
| 5,434,842 A | 7/1995 | Weiss et al. |
| 5,506,420 A | 4/1996 | Kossovsky et al. |
| 5,525,811 A | 6/1996 | Sakurai et al. |
| 5,539,100 A | 7/1996 | Wasielewski et al. |
| 5,707,845 A | 1/1998 | Ueyama et al. |
| 5,744,598 A | 4/1998 | Shalkos et al. |
| 5,804,850 A * | 9/1998 | Evans, Jr. et al. ...... 365/149 X |
| 5,840,443 A | 11/1998 | Gregg et al. |
| 5,858,666 A | 1/1999 | Weiss |

FOREIGN PATENT DOCUMENTS

| | | |
|---|---|---|
| EP | 0272935 | 12/1987 |
| EP | 0307210 | 9/1988 |
| EP | 0307211 | 9/1988 |
| EP | 0363147 | 10/1989 |
| WO | 99/24527 | 5/1999 |

OTHER PUBLICATIONS

Collier et al., "Electronically Configurable Molecular–Based Logic Gates", SCIENCE, vol. 285, Jul. 16, 1999, pp. 391–394.

"Ferrocene—Molecule of the Month" Jun. 1996, University of Oxford Web Page, http://www.ncl.ox.ac.uk/mom/ferrocene/ferrocene2.html.

"Ferrocene—Synthesis", Jun. 1996, University of Oxford Web Page, http://www.ncl.ox.ac.uk/mom/ferrocene/synthesis.html.

(List continued on next page.)

Primary Examiner—Huan Hoang
(74) Attorney, Agent, or Firm—Law Offices of Jonathan Alan Quine; Tom Hunter

(57) ABSTRACT

This invention provides novel high density memory devices that are electrically addressable permitting effective reading and writing, that provide a high memory density (e.g., $10^{15}$ bits/cm$^3$), that provide a high degree of fault tolerance, and that are amenable to efficient chemical synthesis and chip fabrication. The devices are intrinsically latchable, defect tolerant, and support destructive or non-destructive read cycles. In a preferred embodiment, the device comprises a fixed electrode electrically coupled to a storage medium having a multiplicity of different and distinguishable oxidation states wherein data is stored in said oxidation states by the addition or withdrawal of one or more electrons from said storage medium via the electrically coupled electrode.

93 Claims, 25 Drawing Sheets

OTHER PUBLICATIONS

Article Entitled "Encapsulated Electroactive Molecules" by Christopher B. Gorman, published in *Advanced Materials* 1997, 9 No. 14, pp. 1117–1119.

Article Entitled "Molecular Structure—Property Relationships for Electron–Transfer Rate Attenuation in Redox–Active Core Dendrimers" by Christopher B. Gorman, et al.,. *J. Am. Chem. Society* 1999, 121, 9958–9966.

* cited by examiner

101 X-axis Logic (Two Levels of Working Electrodes)

102

103 Y-axis Logic (Common Reference Electrode)

Scheme 1

Scheme 2

Scheme 4

Scheme 5

Scheme 8

Scheme 9

HIGH DENSITY NON-VOLATILE MEMORY DEVICE

CROSS-REFERENCE TO RELATED APPLICATIONS

This application is related to an application entitled "High Density Non-Volatile Memory Device Incorporating Thiol-Derivatized Porphyrins" (Ser. No. 09/346,221), filed on Jul. 1, 1999, naming Daniel Tomasz Gryko, Peter Christian Clausen, David F. Bocian, Werner G. Kuhr, and Jonathan S. Lindsey as inventors, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant Number N00014-99-1-0357 from the Office of Naval Research. The Government of the United States of America may have certain rights in the invention.

FIELD OF THE INVENTION

This invention relates to memory devices. In particular this invention provides a nonvolatile electronic memory device capable of storing information in extremely high density.

BACKGROUND OF THE INVENTION

Basic functions of a computer include information processing and storage. In typical computer systems, these arithmetic, logic, and memory operations are performed by devices that are capable of reversibly switching between two states often referred to as "0" and "1." In most cases, such switching devices are fabricated from semiconducting devices that perform these various functions and are capable of switching between two states at a very high speed using minimum amounts of electrical energy. Thus, for example, transistors and transistor variants perform the basic switching and storage functions in computers.

Because of the huge data storage requirements of modern computers, a new, compact, low-cost, very high capacity, high speed memory configuration is needed. To reach this objective, molecular electronic switches, wires, microsensors for chemical analysis, and opto-electronic components for use in optical computing have been pursued. The principal advantages of using molecules in these applications are high component density (upwards of $10^{18}$ bits per square centimeter), increased response speeds, and high energy efficiency.

A variety of approaches have been proposed for molecular-based memory devices. While these approaches generally employ molecular architectures that can be switched between two different states, all of the approaches described to date have intrinsic limitations making their uses in computational devices difficult or impractical.

For example, such approaches to the production of molecular memories have involved photochromic dyes, electrochromic dyes, redox dyes, and molecular machines. Each of these approaches, however, has intrinsic limitations that ultimately render it unsuitable for use in molecular memories. For example, photochromic dyes change conformation in response to the absorption of light (e.g. cis-trans interconversion of an alkene, ring opening of a spiropyran, interconversion between excited-states in bacteriorhodopsin, etc.). Typically, the molecular structure of the dye is interconverted abetween two states that have distinct spectral properties.

Reading and writing data with such photochromic dyes requires use of light, often in the visible region (400–700 nm). Light-mediated data storage has intrinsic diffraction-limited size constraints. Moreover, most photochromic schemes are limited to scanning and interrogating dyes deposited on a surface and are not amenable to 3-D data storage. Even with near-field optical approaches, which might allow reliable encoding/reading of data elements of 100×100 nm dimensions (Nieto-Vesperinas and Garcia, N., eds. (1996) *Optics at the Nanometer Scale*, NATO ASI Series E, Vol. 319, Kluwer Academic Publishers: Dordrecht) the inherent restricted dimensionality (2-D) limits data density to $10^{10}$ bits/cm$^2$. Strategies for 3-dimensional reading and writing of photochromic systems have been proposed that rely on two-photon excitation of dyes to encode data, and one-photon excitation to read the data (Birge et al. (1994) *Amer. Sci.* 82: 349–355, Parthenopoulos and Rentzepis (1989) *Science*, 245: 843–845), but it is believed that no high-density memory cubes have reached prototype stage in spite of the passage of at least a decade since their initial proposition. In addition, it is noted that these dyes often exhibit relatively slow switching times ranging from microsecond to millisecond durations.

Electrochromic dyes have been developed that undergo a slight change in absorption spectrum upon application of an applied electric field (Liptay (1969) *Angew. Chem., Int. Ed. Engl.* 8: 177–188). The dyes must be oriented in a fixed direction with respect to the applied field. Quite high fields (>$10^7$ V/cm) must be applied to observe an altered absorption spectrum which can result in heat/power dissipation problems. In addition, the change in the absorption spectrum is typically quite small, which can present detection difficulties. The dyes revert to the initial state when the applied field is turned off.

Redox dyes have been developed that undergo a change in absorption spectrum upon chemical or electrochemical reduction (typically a 2-electron, 2-proton reduction) (Otsuki et al. (1996) *Chem. Lett.* 847–848). Such systems afford bistable states (e.g., quinone/hydroquinone, azo/hydrazo). Redox dyes have only been examined in solution studies, where they have been proposed for applications as switches and sensors (de Silva et al. (1997) *Chem. Rev.* 97: 1515–1566). On a solid substrate, electrochemical reduction would need to be accompanied by a source of protons. The latter requirement may be difficult to achieve on a solid substrate. Furthermore, any optical reading scheme would pose the same 2-D limitations as described for photochromic dyes.

Yet another approach involves the design of molecular machines (Anell et al. (1992) *J. Am. Chem. Soc.* 114: 193–218). These elegant molecular architectures have moving parts that can be switched from one position to another by chemical or photochemical means. The chemically induced systems have applications as sensors but are not practical for memory storage, while the photochemically induced systems have the same fundamental limitations as photochromic dyes. Moreover, methods have not yet been developed for delineating the conformation/structure of the molecular machine that are practical in any device applications. $^1$H NMR spectroscopy, for example, is clearly the method of choice for elucidating structure/conformation for molecules in solution, but is totally impractical for interrogating a molecular memory element. None of the current architectures for molecular machines has been designed for assembly on a solid substrate, an essential requirement in a viable device.

In summary, photochromic dyes, electrochromic dyes, redox-sensitive dyes, and molecular machines all have fundamental limitations that have precluded their application as viable memory elements. These molecular architectures are typically limited by reading/writing constraints. Furthermore, even in cases where the effective molecular bistability is obtained, the requirement for photochemical reading restricts the device architecture to a 2-dimensional thin film. The achievable memory density of such a film is unlikely to exceed $10^{10}$ bits/cm$^2$. Such limitations greatly diminish the appeal of these devices as viable molecular memory elements.

SUMMARY OF THE INVENTION

This invention provides novel high density memory devices that are electrically addressable permitting effective reading and writing, that provide a high memory density (e.g., $10^{15}$ bits/cm$^3$), that provide a high degree of fault tolerance, and that are amenable to efficient chemical synthesis and chip fabrication. The devices are intrinsically latchable, defect tolerant, and support destructive or nondestructive read cycles.

In a preferred embodiment, this invention provides an apparatus for storing data (e.g., a "storage cell"). The storage cell includes a fixed electrode electrically coupled to a "storage medium" having a multiplicity of different and distinguishable oxidation states where data is stored in the (preferably non-neutral) oxidation states by the addition or withdrawal of one or more electrons from said storage medium via the electrically coupled electrode. In preferred storage cells, the storage medium stores data at a density of at least one bit, preferably at a density of at least 2 bits, more preferably at a density of at least 3 bits, and most preferably at a density of at least 5, 8, 16, 32, or 64 bits per molecule. Thus, preferred storage media have at least 2, 8, 16, 32, 64, 128 or 256 different and distinguishable oxidation states. In particularly preferred embodiments, the bits are all stored in non-neutral oxidation states. In a most preferred embodiment, the different and distinguishable oxidation states of the storage medium can be set by a voltage difference no greater than about 5 volts, more preferably no greater than about 2 volts, and most preferably no greater than about 1 volt.

The storage medium is electrically coupled to the electrode(s) by any of a number of convenient methods including, but not limited to, covalent linkage (direct or through a linker), ionic linkage, non-ionic "bonding", simple juxtaposition/apposition of the storage medium to the electrode(s), or simple proximity to the electrode(s) such that electron tunneling between the medium and the electrode(s) can occur. The storage medium can contain or be juxtaposed to or layered with one or more dielectric material(s). Preferred dielectric materials are imbedded with counterions (e.g. Nafion). The storage cells of this invention are fully amenable to encapsulation (or other packaging) and can be provided in a number of forms including, but not limited to, an integrated circuit or as a component of an integrated circuit, a non-encapsulated "chip", etc. In some embodiments, the storage medium is electronically coupled to a second electrode that is a reference electrode. In certain preferred embodiments, the storage medium is present in a single plane in the device. The apparatus of this invention can include the storage medium present at a multiplicity of storage locations, and in certain configurations, each storage location and associated electrode(s) forms a separate storage cell. The storage present on a single plane in the device or on multiple planes and said storage locations are present on multiple planes of said device. Virtually any number (e.g., 16, 32, 64, 128, 512, 1024, 4096, etc.) of storage locations and/or storage cells can be provided in the device. Each storage location can be addressed by a single electrode or by two or more electrodes. In other embodiments, a single electrode can address multiple storage locations and/or multiple storage cells.

In preferred embodiments, one or more of the electrode(s) is connected to a voltage source (e.g. output of an integrated circuit, power supply, potentiostat, microprocessor (CPU), etc.) that can provide a voltage/signal for writing, reading, or refreshing the storage cell(s). One or more of the electrode (s) is preferably connected to a device (e.g., a voltammetric device, an amperometric device, a potentiometric device, etc.) to read the oxidation state of said storage medium. In particularly preferred embodiments, the device is an impedance spectrometer or a sinusoidal voltammeter. Various signal processing methods can be provided to facilitate readout in the time domain or in the frequency domain. Thus, in some embodiments, the readout device(s) provide a Fourier transform (or other frequency analysis) of the output signal from said electrode. In certain preferred embodiments, the device refreshes the oxidation state of said storage medium after reading said oxidation state.

A wide variety of molecules can be used as storage molecules and hence comprise the storage medium. Preferred molecules include, but are not limited to a porphyrinic macrocycle, a metallocene, a linear polyene, a cyclic polyene, a heteroatom-substituted linear polyene, a heteroatom-substituted cyclic polyene, a tetrathiafulvalene, a tetraselenafalvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, and a peri-bridged naphthalene dichalcogenide. Even more preferred molecules include a porphyrin, an expanded porphyrin, a contracted porphyrin, a ferrocene, a linear porphyrin polymer, and a porphyrin array. Certain particularly preferred storage molecules include a porphyrinic macrocycle substituted at a β-position or at a meso-position. Molecules well suited for use as storage molecules include the molecules described herein (e.g. the molecules of Formulas I–XXVIII).

Particularly preferred methods and/or devices of this invention utilize a "fixed" electrode. Thus, in one embodiment, methods and/or devices in which the electrode (s) are moveable (e.g. one or ore electrodes is a "recording head", the tip of a scanning tunneling microscope (STM), the tip of an atomic force microscope (AFM), or other forms in which the electrode is movable with respect to the storage medium are excluded. In certain embodiments, methods and/or devices and/or storage media, and/or storage molecules in which the storage molecule is an alkanethiolferrocene are excluded. Similarly in certain embodiments, methods and/or devices and/or storage media, in which the storage molecules are responsive to light and/or in which the oxidation state of a storage molecule is set by exposure to light are excluded.

In another embodiment, this invention provides an information storage medium. The information storage medium can be used to assemble storage cells and/or the various memory devices described herein. In a preferred embodiment the storage medium comprises one or more different storage molecules. When different species of storage molecule are present, each species of storage molecule oxidation state(s) different from and distinguishable from the oxidation state(s) of the other species of storage molecule comprising the storage medium. In preferred embodiments, the storage molecule(s) include a porphyrinic macrocycle, a metallocene, a linear polyene, a cyclic polyene, a heteroatom-substituted linear polyene, a heteroatom-substituted cyclic polyene, a tetrathiafulvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, or a peri-bridged naphthalene dichalcogenide. In even more preferred embodiment, the storage molecule(s) include a porphyrin, an expanded porphyrin, a contracted porphyrin, a ferrocene, a linear porphyrin polymer, or a porphyrin array. Preferred storage molecules contain two or more covalently linked redox-active subunits. In various preferred embodiments, the storage molecules include any of the storage molecules as described herein (e.g. the molecules of Formulas I–XXVIII).

In still another embodiment this invention provides a collection of molecules for the production of a data storage medium. A preferred collection comprises a plurality of storage molecules wherein each species of storage molecule has an oxidation state different from and distinguishable from the oxidation states of the other species of storage molecules comprising the collection. In various preferred embodiments, the storage molecules include any of the storage molecules as described herein (e.g. the molecules of Formulas I–XXVIII).

This invention also provides particularly preferred molecules for the storage of information (storage molecules). The molecules preferably have at least one non-neutral oxidation state and more preferably have at least two different and distinguishable non-neutral oxidation states. In various preferred embodiments, the storage molecules include any of the storage molecules as described herein (e.g. the molecules of Formulas I–XXVIII).

This invention also provides methods of storing data. The methods involve i) providing an apparatus, e.g., comprising one or more storage cells as described herein; and ii) applying a voltage to the electrode at sufficient current to set an oxidation state of said storage medium (the storage medium comprising one or more storage cells). In preferred embodiments, the voltage ranges is less than about 5 volts, more preferably less than about 2 volts, and most preferably less than about 1 or less than about 0.5 volts. The voltage can be the output of any convenient voltage source (e.g. output of an integrated circuit, power supply, logic gate, potentiostat, microprocessor (CPU), etc.) that can provide a voltage/signal for writing, reading, or refreshing the storage cell(s).

The method can further involve detecting the oxidation state of the storage medium and thereby reading out the data stored therein. The detection (read) can optionally involve refreshing the oxidation state of the storage medium (particularly in static-hole devices). The read (detecting) can involve analyzing a readout signal in the time or frequency domain and can thus involve performing a Fourier transform on the readout signal. The detection can be by any of a variety of methods including, but not limited to a voltammetric method. One particularly preferred readout utilizes impedance spectroscopy. The readout (detecting) can involve exposing the storage medium to an electric field to produce an electric field oscillation having characteristic frequency and detecting the characteristic frequency. In preferred embodiments, the storage cells used in the methods of this invention have storage media comprising one or more of the storage molecules described herein (e.g. the molecules of Formulas I–XXVIII).

This invention additionally provides the memory devices of this invention (e.g. memory cells) in a computer system. In addition computer systems utilizing the memory devices of this invention are provided. Preferred computer systems include a central processing unit, a display, a selector device, and a memory device the storage devices (e.g. storage cells) of this invention.

DEFINITIONS

The term "oxidation" refers to the loss of one or more electrons in an element, compound, or chemical substituent/subunit. In an oxidation reaction, electrons are lost by atoms of the element(s) involved in the reaction. The charge on these atoms must then become more positive. The electrons are lost from the species undergoing oxidation and so electrons appear as products in an oxidation reaction. An oxidation is taking place in the reaction $Fe^{2+}(aq) \rightarrow Fe^{3+}(aq)+e^-$ because electrons are lost from the species being oxidized, $Fe^{2+}(aq)$, despite the apparent production of electrons as "free" entities in oxidation reactions. Conversely the term reduction refers to the gain of one or more electrons by an element, compound, or chemical substituent/subunit.

An "oxidation state" refers to the electrically neutral state or to the state produced by the gain or loss of electrons to an element, compound, or chemical substituent/subunit. In a preferred embodiment, the term "oxidation state" refers to states including the neutral state and any state other than a neutral state caused by the gain or loss of electrons (reduction or oxidation).

The term "multiple oxidation states" means more than one oxidation state. In preferred embodiments, the oxidation states may reflect the gain of electrons (reduction) or the loss of electrons (oxidation).

The terms "different and distinguishable" when referring to two or more oxidation states means that the net charge on the entity (atom, molecule, aggregate, subunit, etc.) can exist in two different states. The states are said to be "distinguishable" when the difference between the states is greater than thermal energy at room temperature (e.g. 0° C. to about 40° C.).

The term "electrode" refers to any medium capable of transporting charge (e.g. electrons) to and/or from a storage molecule. Preferred electrodes are metals or conductive organic molecules. The electrodes can be manufactured to virtually any 2-dimensional or 3-dimensional shape (e.g. discrete lines, pads, planes, spheres, cylinders, etc.).

The term "fixed electrode" is intended to reflect the fact that the electrode is essentially stable and unmovable with respect to the storage medium. That is, the electrode and storage medium are arranged in an essentially fixed geometric relationship with each other. It is of course recognized that the relationship alters somewhat due to expansion and contraction of the medium with thermal changes or due to changes in conformation of the molecules comprising the electrode and/or the storage medium. Nevertheless, the overall spatial arrangement remains essentially invariant. In a preferred embodiment this term is intended to exclude systems in which the electrode is a movable "probe" (e.g. a writing or recording "head", an atomic force microscope (AFM) tip, a scanning tunneling microscope (STM) tip, etc.).

The term "working electrode" is used to refer to one or more electrodes that are used to set or read the state of a storage medium and/or storage molecule.

The term "reference electrode" is used to refer to one or more electrodes that provide a reference (e.g. a particular reference voltage) for measurements recorded from the working electrode. In preferred embodiments, the reference electrodes in a memory device of this invention are at the same potential although in some embodiments this need not be the case.

The term "electrically coupled" when used with reference to a storage molecule and/or storage medium and electrode refers to an association between that storage medium or molecule and the electrode such that electrons move from the storage medium/molecule to the electrode or from the electrode to the storage medium/molecule and thereby alter the oxidation state of the storage medium/molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the storage medium/molecule may simply be contacted with the electrode surface. There also need not necessarily be any contact between the electrode and the storage medium/molecule where the electrode is sufficiently close to the storage medium/molecule to permit electron tunneling between the medium/molecule and the electrode.

The term "redox-active unit" or "redox-active subunit" refers to a molecule or component of a molecule that is capable of being oxidized or reduced by the application of a suitable voltage.

The term "subunit", as used herein, refers to a redox-active component of a molecule.

The terms "storage molecule" or "memory molecule" refer to a molecule having one or more oxidation states that can be used for the storage of information (e.g. a molecule comprising one or more redox-active subunits). Preferred storage molecules have two or more different and distinguishable non-neutral oxidation states.

The term "storage medium" refers to a composition comprising two or more storage molecules. The storage medium can contain only one species of storage molecule or it can contain two or more different species of storage molecule.

The term "storage medium" as used herein refers to a collection of storage molecules. Preferred storage media comprise a multiplicity (at least 2) of different and distinguishable (preferably non-neutral) oxidation states. The multiplicity of different and distinguishable oxidation states can be produced by the combination of different species of storage molecules, each species contributing to said multiplicity of different oxidation states and each species having a single non-neutral oxidation state. Alternatively or in addition, the storage medium can comprise one or more species of storage molecule having a multiplicity of non-neutral oxidation states. The storage medium can contain predominantly one species of storage molecule or it can contain a number of different storage molecules. The storage media can also include molecules other than storage molecules (e.g. to provide chemical stability, suitable mechanical properties, to prevent charge leakage, etc.).

The term "electrochemical cell" consists minimally of a reference electrode, a working electrode, a redox-active medium (e.g. a storage medium), and, if necessary, some means (e.g., a dielectric) for providing electrical conductivity between the electrodes and/or between the electrodes and the medium. In some embodiments, the dielectric is a component of the storage medium.

The terms "memory element", "memory cell", or "storage cell" refer to an electrochemical cell that can be used for the storage of information. Preferred "storage cells" are discrete regions of storage medium addressed by at least one and preferably by two electrodes (e.g. a working electrode and a reference electrode). The storage cells can be individually addressed (e.g. a unique electrode is associated with each memory element) or, particularly where the oxidation states of different memory elements are distinguishable, multiple memory elements can be addressed by a single electrode. The memory element can optionally include a dielectric (e.g. a dielectric impregnated with counterions).

The term "storage location" refers to a discrete domain or area in which a storage medium is disposed. When addressed with one or more electrodes, the storage location may form a storage cell. However if two storage locations contain the same storage media so that they have essentially the same oxidation states, and both storage locations are commonly addressed, they may form one functional storage cell.

Addressing a particular element refers to associating (e.g., electrically coupling) that memory element with an electrode such that the electrode can be used to specifically determine the oxidation state(s) of that memory element.

The term "storage density" refers to the number of bits per volume and/or bits per molecule that can be stored. When the storage medium is said to have a storage density greater than one bit per molecule, this refers to the fact that a storage medium preferably comprises molecules wherein a single molecule is capable of storing at least one bit of information.

The terms "read" or "interrogate" refer to the determination of the oxidation state(s) of one or more molecules (e.g. molecules comprising a storage medium).

The term "refresh" when used in reference to a storage molecule or to a storage medium refers to the application of a voltage to the storage molecule or storage medium to re-set the oxidation state of that storage molecule or storage medium to a predetermined state (e.g. an oxidation state the storage molecule or storage medium was in immediately prior to a read).

The term "$E_{1/2}$" refers to the practical definition of the formal potential (E°) of a redox process as defined by $E = E° + (RT/nF)\ln(D_{ox}/D_{red})$ where R is the gas constant, T is temperature in K (Kelvin), n is the number of electrons involved in the process, F is the Faraday constant (96,485 Coulomb/mole), $D_{ox}$ is the diffusion coefficient of the oxidized species and $D_{red}$ is the diffusion coefficient of the reduced species.

A voltage source is any source (e.g. molecule, device, circuit, etc.) capable of applying a voltage to a target (e.g. an electrode).

The term "present on a single plane", when used in reference to a memory device of this invention refers to the fact that the component(s) (e.g. storage medium, electrode(s), etc.) in question are present on the same physical plane in the device (e.g. are present on a single lamina). Components that are on the same plane can typically be fabricated at the same time, e.g., in a single operation. Thus, for example, all of the electrodes on a single plane can typically be applied in a single (e.g., sputtering) step (assuming they are all of the same material).

The phrase "output of an integrated circuit" refers to a voltage or signal produced by a one or more integrated circuit(s) and/or one or more components of an integrated circuit.

A "voltammetric device" is a device capable of measuring the current produced in an electrochemical cell as a result of the application of a voltage or change in voltage.

An "amperometric device" is a device capable of measuring the current produced in an electrochemical cell as a result of the application of a specific potential field potential ("voltage").

A potentiometric device is a device capable of measuring potential across an interface that results from a difference in the equilibrium concentrations of redox molecules in an electrochemical cell.

A "coulometric device" is a device capable of the net charge produced during the application of a potential field ("voltage") to an electrochemical cell.

An impedance spectrometer is a device capable of determining the overall impedance of an electrochemical cell.

A "sinusoidal voltammeter" is a voltammetric device capable of determining the frequency domain properties of an electrochemical cell.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, sub-phthalocyanines, and porphyrin isomers). Preferred porphyrinic macrocycles comprise at least one 5-membered ring.

The term porphyrin refers to a cyclic structure typically composed of four pyrrole rings together with four nitrogen atoms and two replaceable hydrogens for which various metal atoms can readily be substituted. A typical porphyrin is hemin.

The term "multiporphyrin array" refers to a discrete number of two or more covalently-linked porphyrinic macrocycles. The multiporphyrin arrays can be linear, cyclic, or branched.

A linker is a molecule used to couple two different molecules, two subunits of a molecule, or a molecule to a substrate.

A substrate is a, preferably solid, material suitable for the attachment of one or more molecules. Substrates can be formed of materials including, but not limited to glass, plastic, silicon, minerals (e.g. quartz), semiconducting materials, ceramics, metals, etc.

The term "odd hole oxidation state", refers to the case where the number of electron equivalents added or removed from a molecule or molecules is not an integer multiple of the number of redox-active (e.g. oxidizable or reducable) subunits in the molecule or molecules.

The phrase "hole hopping" refers to the exchange of oxidation states between subunits of thermodynamically similar potentials.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, and aryl group may be phenyl ($C_6H_3$) or naphthyl ($C_{10}H_9$). It is recognized that the aryl, while acting as substituent can itself have additional substituents (e.g. the substituents provided for $S^n$ in the various Formulas herein).

The term "alkyl" refers to a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl ($(CH_3)_2CH_3$—).

The term "halogen" refers to one or the electronegative elements of group VIIA of the periodic table (fluorine, chlorine, bromine, iodine, astatine).

The term "nitro" refers to the $NO_2$ group.

The term "amino" refers to the $NH_2$ group.

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CH unit is replaced with a nitrogen atom.

The term "cyano" refers to the —CN group.

The term "thiocyanato" refers to the —SCN group.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not imited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, pertluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the OH of the carboxyl group is replaced by some other substituent (RCO—). Examples include, but are not limited to acetyl, benzoyl, etc In preferred embodiments, when a metal is designated by "M" or "Me", where n is an integer, it is recognized that the metal may be associated with a counterion.

The term "substituent" as used in the formulas herein, particularly designated by S or $S^n$ where n is an integer, in a preferred embodiment refer to redox-active groups (subunits) that can be used to adjust the redox potential(s) of the subject compound. Preferred substituents include, but are not limited to, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In preferred embodiments, a substituted aryl group is attached to a porphyrin or a porphyrinic macrocycle, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl.

Particularly preferred substituents include, but are not limited to, 4-chlorophenyl, 3-acetamidophenyl, 2,4-dichloro-4-trifluoromethyl). Preferred substituents provide a redox potential range of less than about 5 volts, preferably less than about 2 volts, more preferably less than about 1 volt.

The phrase "provide a redox potential range of less than about X volts" refers to the fact that when a substituent providing such a redox potential range is incorporated into a compound, the compound into which it is incorporated has an oxidation potential less than or equal to X volts, where X is a numeric value.

DETAILED DESCRIPTION

This invention provides novel high density memory devices that are electrically addressable permitting effective reading and writing, that provide a high memory density (e.g., $10^{15}$ bits/cm$^3$), that provide a high degree of fault tolerance, and that are amenable to efficient chemical synthesis and chip fabrication. The devices are intrinsically latchable, defect tolerant, and support destructive or non-destructive read cycles.

Figure 1:
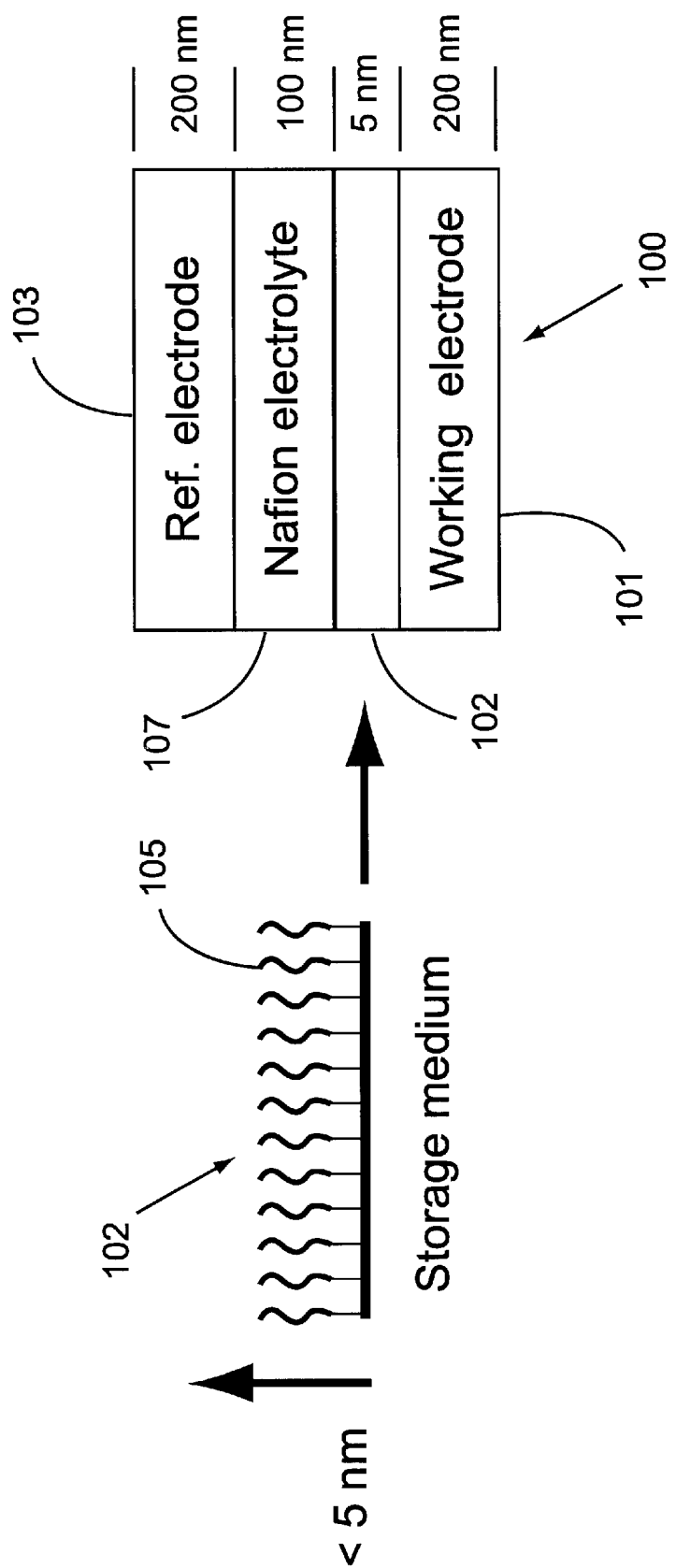
FIG. 1 illustrates a basic molecular memory unit "storage cell" of this invention. The basic memory device, a "storage cell" 100 comprises a working electrode 101 electrically coupled to a storage medium 102 comprising a multiplicity of storage molecules 105. The storage cell optionally includes an electrolyte 107 and a reference electrode 103. The storage medium has a multiplicity of different and distinguishable oxidation states, preferably a multiplicity of different and distinguishable non-neutral oxidation states, and can change oxidation (charge) state when a voltage or signal is applied thereby adding or removing one or more electrons.

One embodiment of this invention is illustrated in FIG. 1. The basic memory device, a "storage cell" 100 comprises a working electrode 101 electrically coupled to a storage medium 102 comprising a multiplicity of storage molecules 105. The storage cell optionally includes an electrolyte 107 and a reference electrode 103. The storage medium has a multiplicity of different and distinguishable oxidation states, preferably a multiplicity of different and distinguishable non-neutral oxidation states, and can change oxidation (charge) state when a voltage or signal is applied thereby adding or removing one or more electrons. Each oxidation state represents a particular bit. Where the storage medium supports eight different and distinguishable oxidation states it stores one byte.

The storage medium remains in the set oxidation state until another voltage is applied to alter that oxidation state. The oxidation state of the storage medium can be readily determined using a wide variety of electronic (e.g. amperometric, coulometric, voltammetric) methods thereby providing rapid readout.

The storage medium comprises molecules having a single oxidation state and/or molecules having multiple different and distinguishable non-neutral oxidation states. Thus, for example, in one embodiment, the storage medium can comprise eight different species of storage molecules each having one non-neutral oxidation state and thereby store one byte. In another embodiment, the storage medium can comprise one species of molecule that has eight different and distinguishable oxidation states and store one byte in that manner as well. As explained herein, a large number of different molecules having different numbers of oxidation states can be used for the storage medium.

Because molecular dimensions are so small (on the order of angstroms) and individual molecules in the devices of this invention can store multiple bits, the storage devices of this invention therefore offer remarkably high storage densities (e.g. $>10^{15}$ bits/cm$^3$).

Moreover, unlike prior art, the devices of this invention are capable of a degree of self-assembly and hence easily fabricated. Because the devices are electrically (rather than optically) addressed, and because the devices utilize relatively simple and highly stable storage elements, they are readily fabricated utilizing existing technologies and easily incorporated into electronic devices. Thus, the molecular memory devices of this invention have a number of highly desirable features:

Because the storage medium of the devices described herein is electrically-addressed, the devices are amenable to the construction of a multilayered chip architecture. An architecture compatible with such a three-dimensional structure is essential to achieve the objective of $10^{15}$ bits/cm$^3$. In addition, because writing and reading is accomplished electrically, many of the fundamental problems inherent with photonics are avoided. Moreover, electrical reading and writing is compatible with existing computer technology for memory storage.

In addition, the devices of this invention achieve a high level of defect tolerance. Defect tolerance is accomplished through the use of clusters of molecules (up to several million in a memory cell). Thus, the failure of one or a few molecules will not alter the ability to read or write to a given memory cell that constitutes a particular bit of memory. In preferred embodiments, the basis for memory storage relies on the oxidation state(s) of porphyrins or other porphyrinic macrocycles of defined energy levels. Porphyrins and porphyrinic macrocycles are well known to form stable radical cations. Indeed, the oxidation and reduction of porphyrins provide the foundation for the biological processes of photosynthesis and respiration. Porphyrin radical cations can be formed chemically on the benchtop exposed to air. We know of no other class of molecules with such robust electroactive properties.

Preferred storage molecules of this invention molecule (e.g., SHMU or DHMU) can hold multiple holes, corresponding to multiple bits. In contrast, the dyes (photochromic, electrochromic, redox) and molecular machines are invariably bistable elements. Bistable elements exist either in a high/low state and hence can only store a single bit. The SHMU and DHMU are unique molecular nanostructures providing resilient storage of multiple bits.

Reading can be accomplished non-destructively or destructively as required in different chip applications. The speed of reading is conservatively estimated to lie in the MHz to GHz regime. Memory storage is inherently latchable due to the stability of the porphyrin or other porphyrinic macrocycle radical cations. Oxidation of the porphyrins or other porphyrinic macrocycles can be achieved at relatively low potential (and at predesignated potentials through synthetic design), enabling memory storage to be achieved at very low power. Porphyrins and porphyrin radical cations ate stable across a broad range of temperatures, enabling chip applications at low temperature, room temperature, or at elevated temperatures.

Fabrication of the devices of this invention relies on known technology. The synthesis of the storage media takes advantage of established building block approaches in porphyrin and other porphyrinic macrocycle chemistry. Synthetic routes have been developed to make the porphyrin and porphyrinic macrocycle building blocks, to join them in covalent nanostructures, and to purify them to a high level (>99%).

In preferred embodiments, the storage medium nanostructures are designed for directed self-assembly on gold surfaces. Such self-assembly processes are robust, result in the culling out of defective molecules, and yield long-range order in the surface-assembled cluster.

Porphyrin-thiols have been assembled on electroactive surfaces. The arrays that define the addressable bits of memory can be achieved through conventional microfabrication techniques. The storage molecules are self-assembled onto these electrode arrays and attached to the gold surface using conventional dipping methods.

I. Uses of the Storage Device

One of ordinary skill in the art will appreciate that the memory devices of this invention have wide applicability in specialized and general-purpose computer systems. Of course commercial realization of the device(s) will be facilitated by the adoption of computer architecture standards compatible with this technology. In addition, commercial adoption of this technology will be facilitated by the use of other molecular electronic components that will serve as on-chip buffers and decoders (that is, molecular logic gates), and the like. In addition, commercialization will be facilitated by the development of a full manufacturing infrastructure.

Regardless, prior to the development of a fully integrated design and manufacturing platform for molecular electronic information storage and transfer, even early generation prototype molecular memory devices described herein have utility in highly specialized military and/or stealthy applications. For example, a prototype 1024/512-bit molecular memory device has sufficient capacity to hold a substantial base of personal and/or other proprietary information. This information could be transported anywhere in the world virtually undetected owing to the extremely small size of the device. If detected, the memory device is easily erased simply by applying a low potential reverse bias current across all memory cells. This protection mechanism can be readily incorporated into any type of transport architecture designed for the memory device.

The memory devices of this invention have sufficient capacity to hold targeting information that could be used in miniaturized, expendable delivery vehicles. Even a memory device that degrades upon multiple read cycles is extremely useful if the number of read cycles is highly limited (perhaps only one). A memory device that degrades upon multiple read cycles or simply with time is also useful in applications where long-term data persistence is not needed or is strategically unwise. Thus, numerous strategically important applications for early generation memory devices present themselves. Successes of the memory devices in these applications will foster even more rapid full-scale commercialization of the technology.

II. Architecture of the Storage Device

Figure 2:
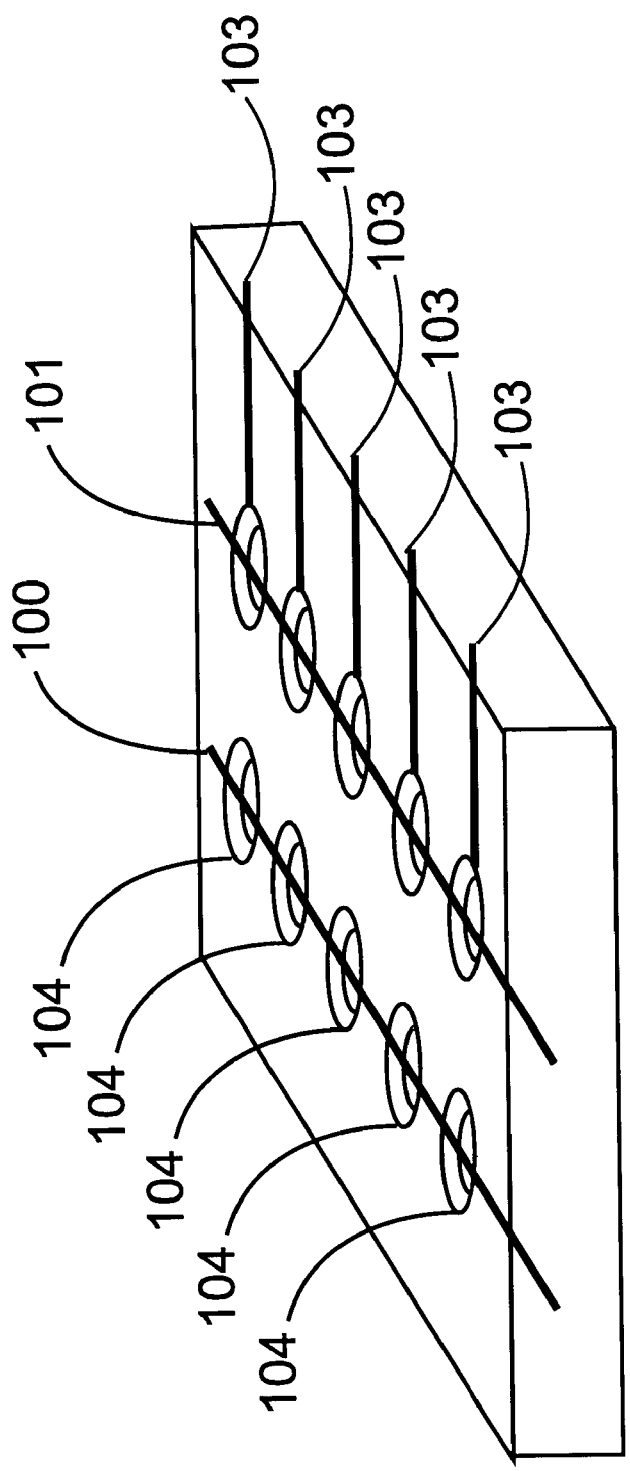
FIG. 2 illustrates the disposition of the storage cell(s) of this invention on a chip.

The basic storage cell (electrode(s) and storage medium) of this invention can be incorporated into a functional device in a wide variety of configurations. One chip-based embodiment of this invention is illustrated in FIG. 2. As illustrated in FIG. 2 the storage medium 102 is disposed in a number of storage locations 104. Each storage location is addressed by a working electrode 101 and a reference electrode 103 so that the storage medium 102 combined with the electrodes forms a storage cell 100 at each storage location.

Figure 3:
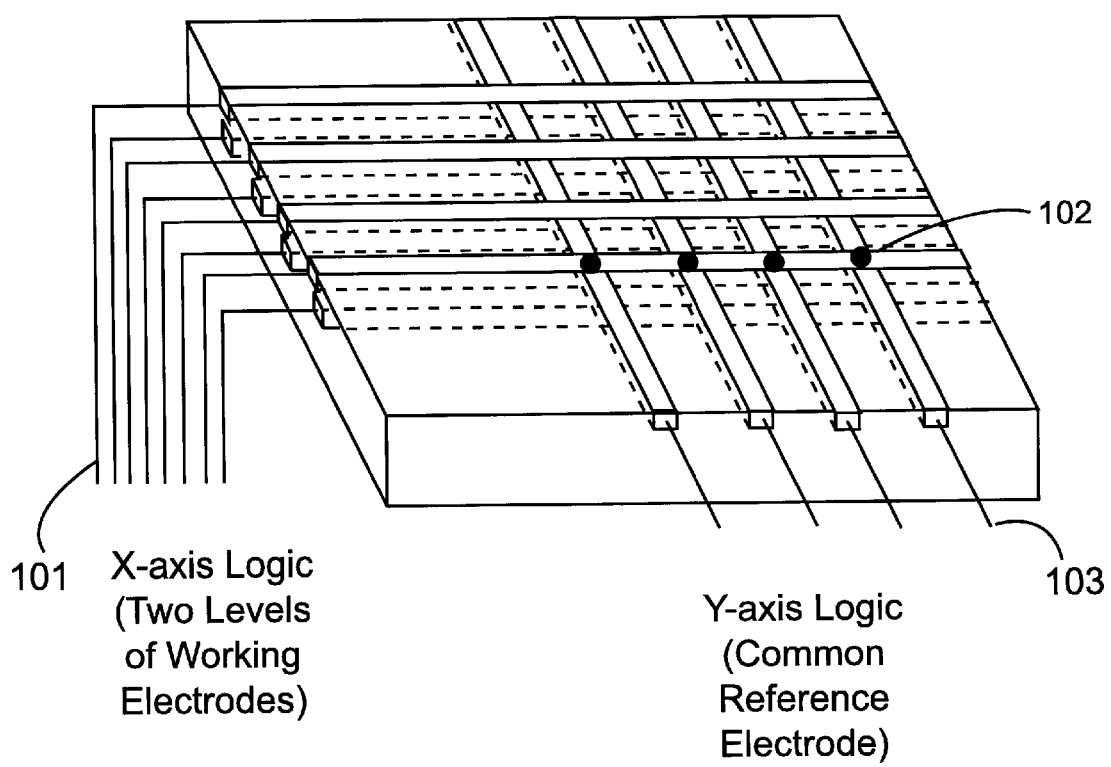
FIG. 3 illustrates a preferred chip-based embodiment of this invention. A two-level chip is illustrated showing working electrodes 101, orthogonal reference electrodes 103, and storage elements 104.

One particularly preferred chip-based embodiment is illustrated in FIG. 3. In the illustrated embodiment, a plurality of working electrodes 101 and reference electrodes 103 are illustrated each addressing storage media 102 localized at discrete storage locations thereby forming a plurality of storage cells 100. Multiple storage cells can be associated with a single addressing electrode as long as oxidation states of the storage cells are distinguishable from each other. It should be noted that this forms a functional definition of a storage cell. Where two discrete areas of storage medium are addressed by the same electrode(s) if the storage media comprise the same species of storage molecule the two discrete areas will functionally perform as a single storage cell, i.e. the oxidation states of both locations will be commonly set, and/or read, and/or reset. The added storage location, however, will increase the fault tolerance of the storage cell as the functional storage cell will contain more storage molecules. In another embodiment, each individual storage cell is associated with a single addressing electrode.

In preferred embodiments, the storage medium comprising the storage cells of a memory device are all electrically coupled to one or more reference electrodes. The reference electrode(s) can be provided as discrete electrodes or as a common backplane.

The chip illustrated in FIG. 3 has two levels of working electrodes and hence two levels of storage cells 100 (with numerous storage cells on each level). Of course, the chip can be fabricated with a single level of electrodes and memory element or literally hundreds or thousands of different levels of storage cell(s), the thickness of the chip being limited essentially by practical packaging and reliability constraints.

In particularly preferred embodiments, a layer of dielectric material optionally imbedded with counterions to ensure electrical connectivity between the working and reference electrode(s) and stability of the cationic species in the absence of applied potential (latching) is disposed in the storage cell. In some embodiments, the dielectric material can be incorporated into the storage medium itself.

While, in some preferred embodiments, feature sizes are rather large (e.g. memory elements approximately (10×10× 10 µm) and electrode thickness ~200 nm, feature size can be reduced at will so that feature sizes are comparable to those in conventional silicon-based devices (e.g., 50 nm–100 nm on each axis).

Figure 4:
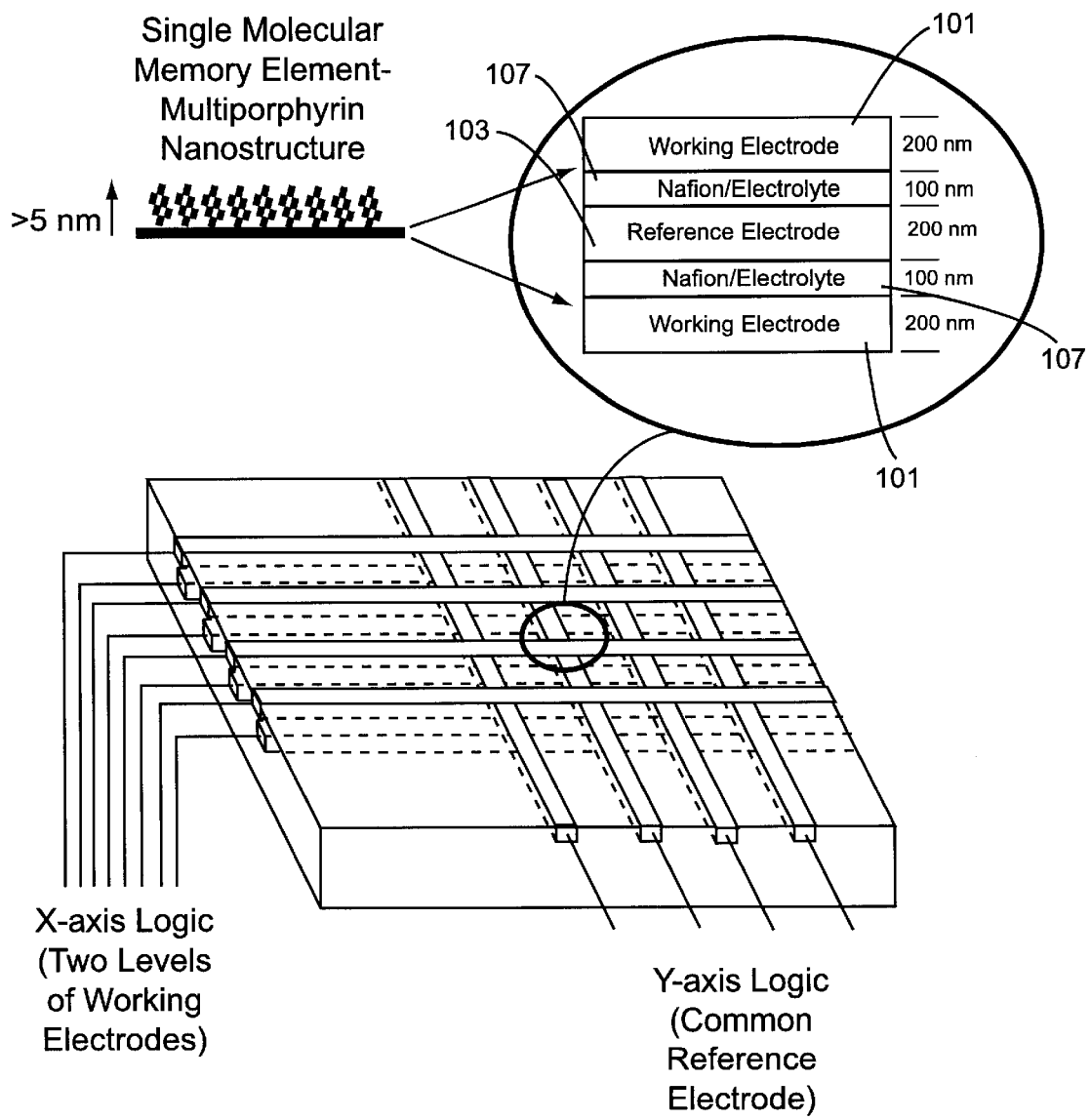
FIG. 4. The three-dimensional architecture of a single memory storage cell (memory element) on the chip.

In a preferred embodiment, the storage device includes: (1) A gold working electrode (e.g., 200 nm thick), deposited on a nonconducting base, and line-etched to achieve electrode widths of 10's to 100's of nm. (2) A monolayer of self-assembled porphyrinic nanostructures (storage molecules 105) attached to the gold surface via the sulfur atom of the thiophenol group. (3) A 100-nm thick layer of dielectric material 107 embedded with counterions to ensure electrical connectivity to the reference electrode and stability of the cationic species in the absence of applied potential (latching). (4) A 200-nm thick nonpolarizable reference electrode 103 line etched in the same fashion as those of the working electrode 101, but assembled with lines orthogonal to the latter electrode. (5) A mirror image construct that utilizes the same reference electrode. Thus, in one embodiment, the three-dimensional architecture of a single memory storage location (memory element) on the chip will look as indicated in FIG. 4.

While the discussion herein of electrodes is with respect to gold electrodes, it will be recognized that numerous other materials will be suitable. Thus, electrode materials include, but are not limited to gold, silver, copper, other metals, metal alloys, organic conductors (e.g. doped polyacetylene, doped polythiophene, etc.), nanostructures, crystals, etc.

Similarly, the substrates used in the fabrication of devices of this invention include, but are not limited to glasses, silicon, minerals (e.g. quartz), plastics, ceramics, membranes, gels, aerogels, and the like.

III. Fabrication and Characterization of the Storage Device

A) Fabrication

The memory devices of this invention can be fabricated using standard methods well known to those of skill in the art. In a preferred embodiment, the electrode layer(s) are applied to a suitable substrate (e.g. silica, glass, plastic, ceramic, etc.) according to standard well known methods (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*). In addition, examples of the use of micromachining techniques on silicon or borosilicate glass chips can be found in U.S. Pat. Nos. 5,194,133, 5,132,012, 4,908,112, and 4,891,120.

In one preferred embodiment a metal layer is beam sputtered onto the substrate (e.g,. a 10 nm thick chromium adhesion layer is sputtered down followed by a 200 nm thick layer of gold). Then maskless laser ablation lithography (see below), performed e.g., with a Nd:YAG laser, is used to create features with micron dimensions, or with an excimer laser to create features of nanometer dimensions) will create an array of parallel lines of conductor (e.g., gold), used as the working electrodes with dimensions ranging between a few microns to a tens of nanometers;

Once the electrode array is formed, the entire array, or portions of the array, or individual electrodes are wetted (e.g. immersed or spotted) with one or more solutions of the appropriate derivatized storage media (e.g. thiol-substituted porphyrin nanostructures), and the constituents of the memory medium (e.g., monomeric porphyrin subunits) self-assemble on the micro-sized gold arrays to form the memory elements. It will be appreciated that different solutions can be applied to different regions of the electrode array to produce storage cells comprising different storage medium. Methods of spotting different reagents on surfaces (e.g. on glass surfaces) at densities up to tens of thousands of different species/spots per $cm^2$ are known (see, e.g., U.S. Pat. No. : 5,807,522).

Then a suitable electrolyte layer (e.g. a thin layer of Nafion polymer) approximately 1 nm to 1000 nm, preferably about 100 nm to about 500 nm, more preferably about 10 nm to about 100 nm and most preferably about one hundred nanometers thick) will be cast over the entire surface of the chip. This polymer serves to hold the electrolyte for electrochemical reaction. Finally, the entire chip is coated with a layer (e.g., 10 nm to about 1000 nm, more preferably 100 nm to about 300 nm and most preferably about 200 nm of conducting material (e.g. silver) which acts as a reference electrode 103.

The chip is then turned 90 degrees, and maskless laser ablation lithography will be performed again to create a second array of parallel lines that are perpendicular to the original set. This forms a three dimensional array of individual memory elements, where each element is formed by the intersection of these two perpendicular linear arrays (see FIG. 4).

Each individual element can be addressed by selecting the appropriate X and Y logic elements, corresponding to one gold working electrode and one reference electrode separated by the Nafion polymer/electrolyte layer. Since this structure is inherently three dimensional, it should be possible to extend the array into the Z-direction, creating a 3-D array of memory elements as large as it is feasible to connect to.

These structures are initially created on the micron scale. It is possible to decrease the size of these structures to sub-micron dimensions. It is possible to create these structures on a scale similar to silicon microstructures created with conventional nanolithographic techniques (i.e. 100–200 nm). This would allow the interfacing of the memory elements with conventional silicon-based semiconductor electronics.

In the laser-ablation lithography discussed above, coherent light is sent through a beam splitter (50% transmittance) and reflected by a mirror to make two nearly parallel identical beams (Rosenwald et al. (1998) *Anal. Chem.*, 70: 1133–1140). These beams are sent through e.g., a 50 cm focal length lens for ease in focusing to a common point. The placement of the beams is fine-tuned to allow complete overlap of the mode structure of the laser spot. Higher order interference patterns are minimized through the use of high quality optics (1/10 wave surface flatness). This ensures that the variation between intensity maxima and minima in the first order will be several orders of magnitude larger than those formed with second and higher orders. This produces a well-defined pattern of lines across the electrode surface, where the spacing between points of positive interference (D) can be approximated by the Bragg Equation: $n\lambda = 2D\sin(\theta/2)$, where $\lambda$=wavelength, $\theta$=angle between the beams, and n is order. For example, when a Nd:YAG is used at 1064 nm, the recombination of the two beams in this manner generates an interference pattern with ~2 micron spacing when the angle between the 2 beams is 15°. The interference pattern spacing can easily be changed by modifying the angle between the beams. Attenuation of the beam was accomplished by inserting one or more neutral density filters before the beam splitter. In this way, the exposure of the gold layer to the Nd-YAG interference pattern can be performed at different beam attenuations to produce power densities between 1 and 100 $MW/cm^2$.

B) Electrically Coupling Storage Medium to Electrode

In the storage devices of this invention, the storage medium is electrically coupled to one or more electrodes. The term "electrical coupling" is used to refer to coupling schemes that permit the storage medium to gain or lose electrons to the electrode. The coupling can be a direct attachment of the storage medium to the electrode, or an indirect attachment (e.g. via a linker). The attachment can be a covalent linkage, an ionic linkage, a linkage driven by hydrogen bonding or can involve no actual chemical attachment, but simply a juxtaposition of the electrode to the storage medium. In some embodiments, the electrode can be some distance (e.g., about 5 Å to about 50 Å) from the storage medium and electrical coupling can be via electron tunneling.

In some preferred embodiments, a "linker" is used to attach the molecule(s) of the storage medium to the electrode. The linker can be electrically conductive or it can be short enough that electrons can pass directly or indirectly between the electrode and a molecule of the storage medium.

The manner of linking a wide variety of compounds to various surfaces is well known and is amply illustrated in the literature. Means of coupling the molecules comprising the storage medium will be recognized by those of skill in the art. The linkage of the storage medium to a surface can be covalent, or by ionic or other non-covalent interactions. The surface and/or the molecule(s) may be specifically derivatized to provide convenient linking groups (e.g. sulfur, hydroxyl, amino, etc.).

The linker can be provided as a component of the storage medium molecule(s) or separately. Linkers, when not joined to the molecules to be linked are often either hetero- or homo-bifunctional molecules that contain two or more reactive sites that may each form a covalent bond with the respective binding partner (i.e. surface or storage medium molecule). When provided as a component of a storage molecule, or attached to a substrate surface, the linkers are preferably spacers having one or more reactive sites suitable for bonding to the respective surface or molecule.

Linkers suitable for joining molecules are well known to those of skill in the art and include, but are not limited to any of a variety of, a straight or branched chain carbon linker, or a heterocyclic carbon linker, amino acid or peptide linkers, and the like. Particularly preferred linkers include, but are not limited to 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, and 4,4"-terphenyl. Linkers include molecules that join one or more molecules of the storage medium to the electrode(s).

C) Addressing the Memory Cells

Addressing of the storage cell(s) in the devices of this invention is relatively straightforward. In a simple approach a discrete pair of electrodes (one working and one reference electrode) can be connected to every storage cell. Individual reference electrodes, however are not required and can be replaced with one or more common reference electrodes connected to all or to a subset of all of the storage elements in a particular device. Alternatively, the common reference electrodes can be replaced with one or more conductive "backplanes" each communicating to all, or to a subset, of the storage cells in a particular device.

Where the storage cells contain identical storage media, each storage cell is preferably addressed with a separate working electrode so that the storage (oxidation) states of the storage cells can be distinguished from each other. Where the storage cells contain different storage media such that the oxidation states of one storage cell is different and distinguishable from the oxidation states of another storage cell, the storage cells are preferably addressed by a common working electrode thereby reducing the number of electrodes in a device.

In one preferred embodiment, the storage devices of this invention contain (64, 128, 256, 512, 1024 or more storage locations per layer (64, 128, 256, 512, 1024 or more locations in the mirror image architecture) with each location capable of holding a multiple-bit SHMU or DHMU word. Accordingly, a preferred 1024-bit SHMU or a preferred 512-bit DHMU chip will contain 8 wiring interconnects on each of the three electrode grids in the 3-dimensional WPDRDPW architecture illustrated in FIG. 4.

D) Characterization of the Memory Device

The performance (e.g. operating characteristics) of the memory devices of this invention is characterized by any of a wide variety of methods, most preferably by electrochemical methods (amperometry, sinusoidal voltammetry and impedance spectroscopy, see, e.g., Howell et al. (1986) *Electroanal. Chem.*, 209: 77–90; Singhal et al. (1997) *Anal. Chem.*, 69: 1662–1668; Schick et al. (1989) *Am. Chem. Soc.* 111: 1344–1350), atomic force microscopy, electron microscopy and imaging spectroscopic methods. Surface-enhanced resonance and Raman spectroscopy are also used to examine the storage medium on the electrodes.

Among other parameters, characterization of the memory devices (e.g., memory cells) involves determining the number of storage medium molecules (e.g., porphyrin arrays) required for defect-tolerant operation. Defect tolerance includes factors such as reliably depositing the required number of holes to write the desired digit and accurately detecting the numbers/hopping rates of the holes.

The long-term resistance of electron holes to charge-recombination in the solid-phase medium of the device package is also determined. Using these parameters, the device architecture can be optimized for commercial fabrication.

IV. Architecture of the Storage Medium

The storage medium used in the devices of this invention comprises one or more species of storage molecule. A preferred storage medium is characterized by having a multiplicity of oxidation states. Those oxidation states are provided by one or more redox-active units. A redox-active unit refers to a molecule or to a subunit of a molecule that has one or more discrete oxidation states that can be set by application of an appropriate voltage. Thus, for example, in one embodiment, the storage medium can comprise one species of redox-active molecule where that molecule has two or more (e.g. 8) different and distinguishable oxidation states. Typically, but not necessarily, such multi-state molecules will be composed of several redox-active units (e.g. porphyrins or ferrocenes). In another exemplary embodiment, the storage medium can comprise two or more different species of storage molecule. Each storage molecule comprises at least one redox-active unit, but can easily contain two or more redox-active units. Where each species of storage molecule has a single, non-neutral, oxidation state, the storage medium achieves multiple bit storage by having a plurality of such molecules where each molecule has a different and distinguishable oxidation state (e.g. each species of molecule oxidizes at a different and distinguishable potential). Of course, each species of molecule can have a multiplicity of different and distinguishable oxidation states. Thus, a storage medium comprising eight different species of storage molecule where each of the eight species has eight different and distinguishable oxidation states, will be able to store 64 (8×8) bits of information.

As indicated above, the storage medium can be broken down into individual, e.g., spatially segregated, storage locations. Each storage element can have a storage medium that is the same or different from the other storage elements in the chip and/or system. Where the storage elements are of identical composition, in preferred embodiments, they are separately addressed so that information in one element can be distinguished from information in another element. Where the storage elements are of different composition they can be commonly addressed (where the oxidation states of the commonly addressed storage elements are distinguishable) or they can be individually addressed.

In certain preferred embodiments the storage medium is juxtaposed to a dielectric medium to insure electrical connectivity to a reference voltage (e.g. a reference electrode, a reference backplane, etc.). In particularly preferred embodiments, a layer of dielectric material is imbedded with counterions to ensure electrical connectivity to the reference electrode and stability of the cationic species in the absence of applied potential (latching) is disposed between the reference working electrode(s).

Dielectric materials suitable for the devices of this invention are well known to those of skill in the art. Such materials include, but are not limited to nafion, cellulose acetate, polystyrene sulfonate, poly(vinylpyridine), electronically conducting polymers such as polypyrrolic acid and polyaniline, etc.

The porphyrinic macrocycles identified herein are ideally suited for molecular based memory storage. The porphyrinic macrocycles, and especially the porphyrins, have unique electroactive properties, a well-developed modular synthetic chemistry, and in conjunction with thiols, and other linkers described herein, undergo directed self-assembly on electroactive surfaces.

In addition, as described below, the porphyrinic macrocycles are well suited for the design of multi-bit storage systems. In preferred embodiments, this invention contemplates three fundamental architectures for the storage medium; static hole single-unit (SHSU) storage (e.g. SHSU molecules), static hole multi-unit (SHMU) storage (e.g. SHSU molecules), and dynamic hole multi-unit (DHMU) storage (e.g. DHMU molecules).

A) Static Hole Single Unit (SHSU) Storage

In the simplest embodiments of this invention, the storage medium comprises one or more molecules wherein each molecule has one non-neutral oxidation state. Thus, each molecule is capable of storing one bit (e.g. bit=1 when oxidized and bit=0 when neutral). A number of different species of static hole single unit storage molecules can be assembled into a single storage medium. Thus, for example a number of different ferrocenes, or a number of different porphyrins, or combinations of porphyrin and ferrocene monomers can be combined into a single storage medium.

In one preferred embodiment, a molecule comprising a static hole single unit molecular memory has the formula shown in Formula I.

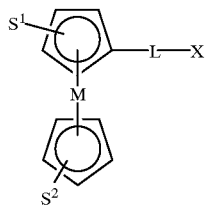

where L is a linker, M is a metal (e.g., Fe, Ru, Os, Co, Ni, Ti, Nb, Mn, Re, V, Cr, W), $S^1$ and are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. In preferred embodiments, a substituted aryl group is attached to the porphyrin, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. Particularly preferred substituents include, but are not limited to, 4-chlorophenyl, 3-acetamidophenyl, 2,4-dichloro-4-trifluoromethyl). Preferred substituents provide a redox potential range of less than about 2 volts. X is selected from the group consisting of a substrate, a reactive site that can covalently couple to a substrate, and a reactive site that can ionically couple to a substrate. It will be appreciated that in some embodiments, L—X can be replaced with another substituent ($S^3$) like $S^1$ or $S^2$. In certain embodiments, L—X can be present or absent, and when present preferably is 4-(2-(4-mercaptophenyl)ethynyl)phenyl, 4-mercaptomethylphenyl, 4-hydroselenophenyl, 4-(2-(4-hydroselenophenyl)ethynyl)phenyl, 4-hydrotellurophenyl, or 4-(2-(4-hydrotellurophenyl)ethynyl)phenyl.

The oxidation state of molecules of Formula I is determined by the metal and the substituents. Thus, particular preferred embodiments are illustrated by Formulas II–VII, (listed sequentially) below:

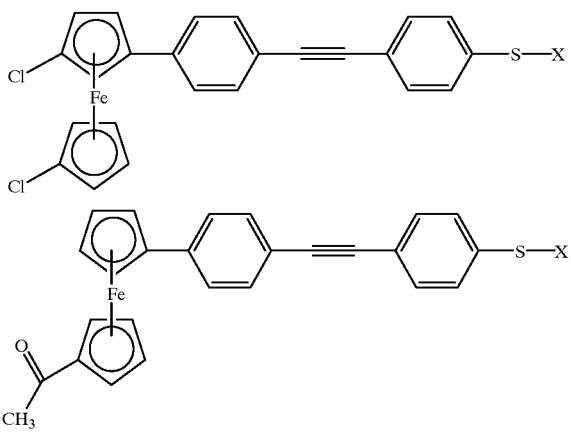

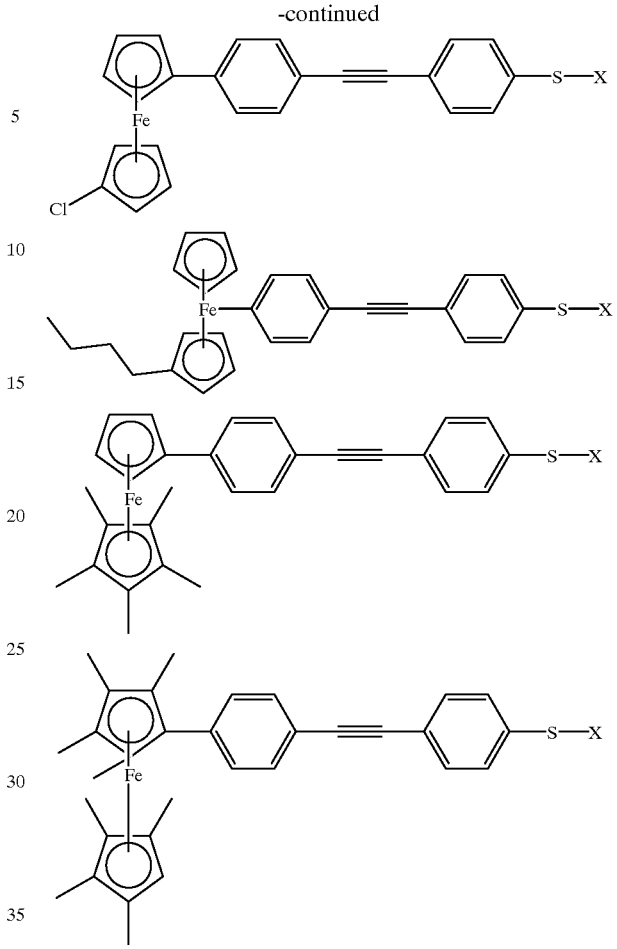

The ferrocenes listed above in Formulas II through VII provide a convenient series of one-bit molecules having different and distinguishable oxidation states. Thus the molecules of Formulas II through VII have oxidation states ($E_{1/2}$) of +0.55 V, +0.48 V, +0.39 V, +0.17 V, −0.05 V, and −0.18 V, respectively, and provide a convenient series of molecules for incorporation into a storage medium of this invention. It will be appreciated that the oxidation states of the members of the series can be routinely altered by changing the metal (M) or the substituents.

B) Static Hole Multi-unit (SHSU) Storage

Static hole multi-unit (SHSU) molecular memories typically comprise a multiplicity of redox-active subunits. In a preferred embodiment, the redox-active subunits are covalently linked to form a single molecule and are selected to have different and distinguishable oxidation states, preferably a multiplicity of different and distinguishable non-neutral oxidation states. Thus, in this configuration a single molecule can have multiple (e.g. 2, 4, 8, 16, 32, 64, 128, 512 etc.) different non-neutral oxidation states.

In one particularly preferred embodiment the static hole multi-unit molecular memory is a "static hole multiporphyrin molecular memory" (SHMMM) storage system. In this embodiment, the redox-active subunits are porphyrinic macrocycles, most preferably porphyrins. The porphyrins can be arranged in a wide variety of configurations (e.g. linear polymers, branched polymers, arrays, etc.), however, linear configurations are well suited to the practice of this invention.

One particularly preferred linear configuration is illustrated by Formula VIII.

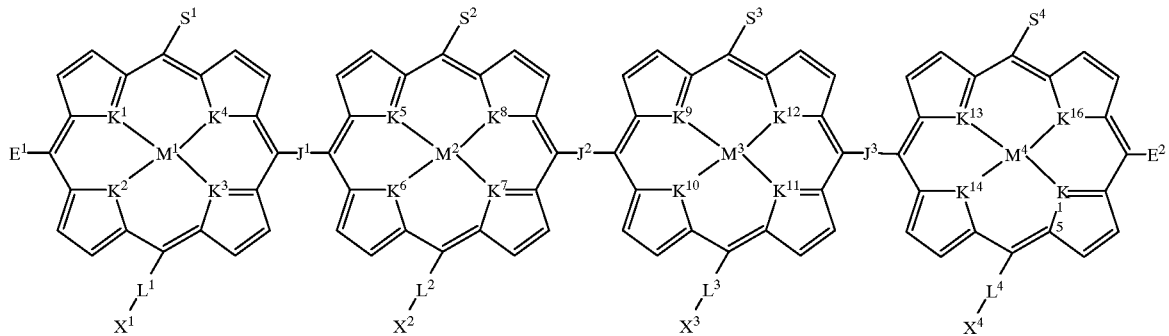

VIII where $S^1$, $S^2$, $S^3$, and $S^4$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts, $M^1$, $M^2$, $M^3$, and $M^4$ are independently selected metals (e.g., Zn, Mg, Cd, Hg, Cu, Ag, Au, Ni, Pd, Pt, Co, Rh, Ir, Mn, B, Al, Ga, Pb, and Sn), $K^1$, $K^2$, $K^3$, $K^4$, $K^5$, $K^6$, $K^7$, $K^8$, $K^9$, $K^{10}$, $K^{11}$, $K^{12}$, $K^{13}$, $K^{14}$, $K^{15}$, and $K^{16}$ are independently selected from the group consisting of N, O, S, Se, Te, and CH, $J^1$, $J^2$, and $J^3$ are independently selected linkers, $L^1$, $L^2$, $L^3$, and $L^4$ are present or absent and, when present are independently selected linkers, $X^1$, $X^2$, $X^3$, and $X^4$ are independently selected from the group consisting of a substrate, a reactive site that can covalently couple to a substrate, and a reactive site that can ionically couple to a substrate, and $E^1$ and $E^2$ are terminating substituents independently aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, or carbamoyl wherein said substituents provide a redox potential range of less than about 2 volts. In preferred embodiments, the molecule has at least two, preferably at least 4, more preferably at least 8, and most preferably at least 16, at least 32, at least 64 or at least 128 different and distinguishable oxidation states. In some embodiments, one or more of the linker/reactive site subunits ($L^1$—$X^1$, $L^2$—$X^2$, $L^3$—$X^3$, or $L^4$—$X^4$), can be eliminated and replaced with a substituent independently selected from the same group as $S^1$, $S^2$, $S^3$, or $S^4$.

In preferred embodiments, the substituents are selected so that the molecule illustrated by Formula XVIII has at least 2, more preferably at least 4 and most preferably at least 8 different and distinguishable oxidation states.

In certain preferred embodiments, $J^1$, $J^2$, and $J^3$ are independently 4,4'-diphenylethyne, 4,4'-diphenylbutadiyne, 4,4'-biphenyl, 1-4-phenylene, 4,4'-stilbene, 1,4-bicyclooctane, 4,4'-azobenzene, 4,4'-benzylideneaniline, or 4,4''-terphenyl.

$L^1$—$X^1$, $L^2$—$X^2$, $L^3$—$X^3$, and $L^4$—$X^4$ are independently present or absent and, when present, can include 4-(2-(4-mercaptophenyl)ethynyl)phenyl, 4-mercaptomethylphenyl, 4-hydroselenophenyl, 4-(2-(4-hydroselenophenyl)ethynyl) phenyl, 4-hydrotellurophenyl, and 4-(2-(4-hydrotellurophenyl)ethynyl)phenyl.

In a particularly preferred embodiment, $K^1$, $K^2$, $K^3$, $K^4$, $K^5$, $K^6$, $K^7$, $K^8$, $K^9$, $K^{10}$, $K^{11}$, $K^{12}$, $K^{13}$, $K^{14}$, $K^{15}$, and $K^{16}$ are the same, $M^1$ and $M^3$ are the same, $M^2$ and $M^4$ are the same and different from $M^1$ and $M^3$, $S^1$ and $S^2$ are the same; and $S^3$ and $S^4$ are the same and different from $S^1$ and $S^2$.

In a most preferred embodiment, the metals ($M^1$, $M^2$, $M^3$, and $M^4$) and the substituents ($S^1$, $S^2$, $S^3$, and $S^4$) are selected so that each porphyrin has two non-neutral oxidation states. $L^1$—$X^1$, $L^2$—$X^2$, $L^3$—$X^3$, and $L^4$—$X^4$ provide convenient linkers for attaching the molecule to a substrate (e.g. an electrode). With each subunit having two oxidation states, the subunits can be configured so that the entire molecule has 8 different and distinguishable oxidation states. One such molecule is illustrated by Formula IX.

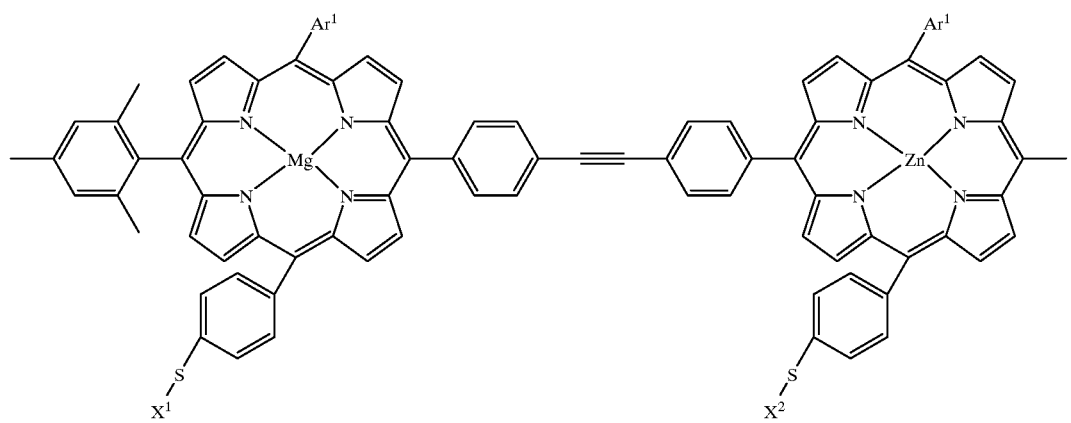

IX

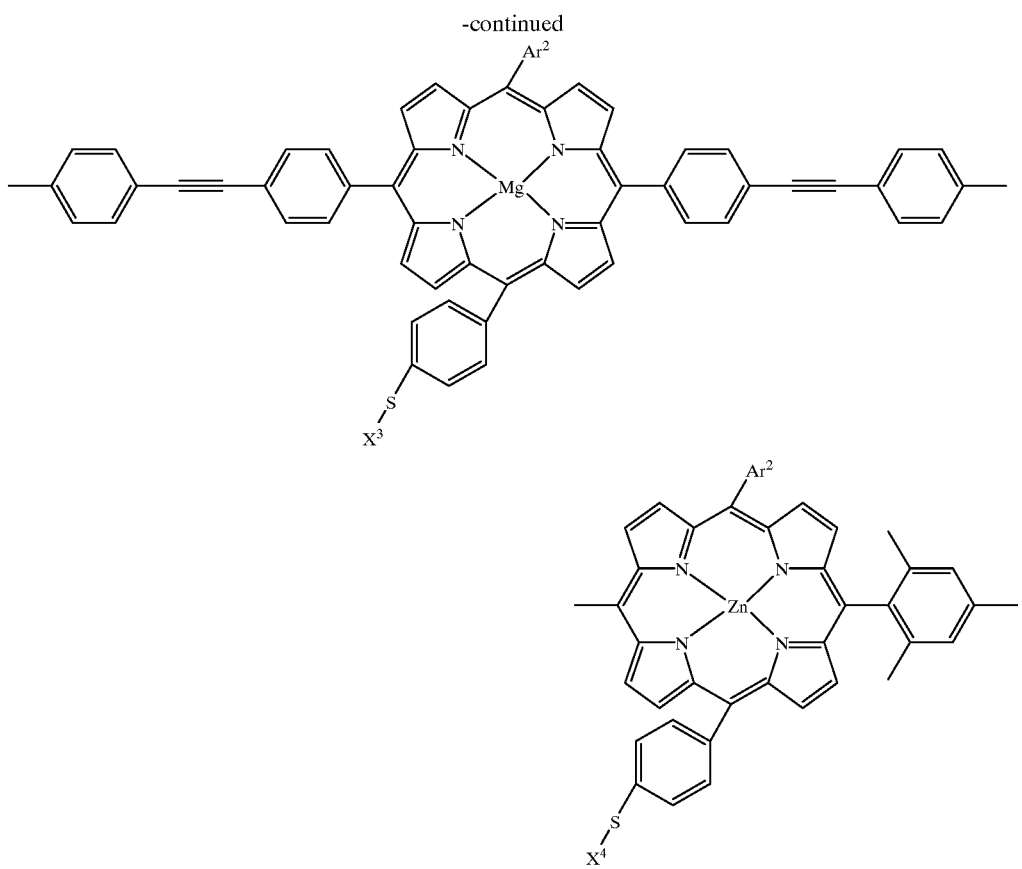

The porphyrin metalation state alters between Mg and Zn in proceeding from one end to the other. The different metalation state alters the redox characteristics of the porphyrins. In particular, magnesium porphyrins are more easily oxidized than zinc porphyrins. Differentiation of the oxidation potentials of the left-most pair of Zn and Mg porphyrins from those of the right-most pair is achieved through the use of different substituents ($Ar^2$, right pair; $Ar^1$, left pair) attached to the meso- (and/or to the β-) positions. The porphyrins are joined via linkers (e.g. p,p'-diarylethyne linkers). These constrain the porphyrins at fixed distances from each other. In addition, each porphyrin bears a linker (e.g., a thiol) for attachment to an electroactive surface such as gold.

Information is stored in the SHMU storage molecule by removing electrons from the porphyrin constituents (leaving a hole and forming a π-cation radical (Strachan et al. (1997) *J. Am. Chem. Soc.*, 119: 11191–11201; Li et al. (1997) *J. Mater. Chem.* 7: 1245–1262, and Seth et al. (1996) *J. Am. Chem. Soc.* 118: 11194–11207; Seth et al. (1994) *J. Am. Chem. Soc.* 116: 10578–10592). The redox characteristics of the Zn and Mg porphyrins in conjunction with the substituents $Ar^1$ and $Ar^2$ permit oxidation to form in sequence, ($MgAr^{1(+)}$, others neutral), ($MgAr^{1(+)}$, $ZaAr^{1(+)}$, with $MgAr^2$ and $ZnAr^2$ neutral], and so forth until two holes have been removed from all of the four metalloporphyrins, i.e., [$MgAr^{1(++)}$, $ZnAr^{1(++)}$, $MgAr^{2(++)}$, $ZnAr^{2(++)}$]. Thus, up to eight holes can be stored in the memory with each unique oxidation state serving as a digit of a basic eight-bit memory element. This is illustrated below in Table 1.

TABLE 1

Bit architecture in a prototype SHMU storage molecule.

| Memory | Subunit P1 $MgAr^1$ | Subunit P2 $ZnAr^1$ | Subunit P3 $MgAr^2$ | Subunit P4 $ZnAr^2$ |
|---|---|---|---|---|
| "parity" | 0 | 0 | 0 | 0 |
| 0 0 0 | + | 0 | 0 | 0 |
| 0 0 1 | + | + | 0 | 0 |
| 0 1 0 | ++ | + | 0 | 0 |
| 0 1 1 | ++ | ++ | 0 | 0 |
| 1 0 0 | ++ | ++ | + | 0 |
| 1 0 1 | ++ | ++ | + | + |
| 1 1 0 | ++ | ++ | ++ | + |
| 1 1 1 | ++ | ++ | ++ | ++ |

The synthetic methodologies already established permit the extension of the linear architecture, thus increasing the dynamic range of the basic memory element well beyond the three bits indicated. Conversely, the molecule could be reduced to two subunits thereby encoding 2 bits (+"parity"). In addition, subunits can be engineered that have more than two oxidation states. Thus for example, molecules and/or subunits can be engineered that have virtually any number (e.g., 2, 4, 8, 16, 32, 64, 128, etc.) of different and distinguishable oxidation states.

In other embodiments, single molecule, non-polymeric molecules can maintain multiple oxidation states and thereby support multiple bits. In preferred embodiments, such molecules comprise multiple redox-active subunits. Certain preferred molecules have 2, 3, 5, 8, or even more different and distinguishable non-neutral oxidation states. One such molecule is illustrated by Formula XI.

XI

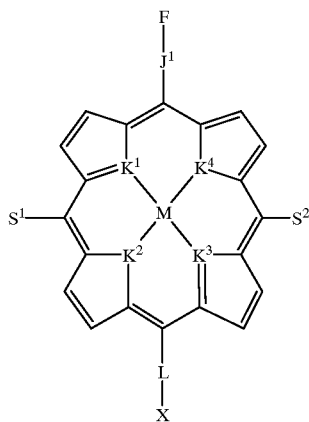

where, F is a redox-active subunit (e.g., a ferrocene, a substituted ferrocene, a metalloporphyrin, or a metallochlorin, etc.), $J^1$ is a linker, M is a metal (e.g., Zn, Mg, Cd, Hg, Cu, Ag, Au, Ni, Pd, Pt, Co, Rh, Ir, Mn, B, Al, Ga, Pb, and Sn), $S^1$ and $S^2$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts, $K^1$, $K^2$, $K^3$, and $K^4$ are independently selected from the group consisting of N, O, S, Se, Te, and CH; L is a linker; X is selected from the group consisting of a substrate, a reactive site that can covalently couple to a substrate, and a reactive site that can ionically couple to a substrate. In some embodiments L—X can be eliminated and replaced with a substituent independently selected from the same group as $S^1$ or $S^2$.

In preferred embodiments, the molecule has at least three different and distinguishable oxidation states. Particularly preferred variants of this storage molecule are illustrated by Formulas XII, XIII, and XIV, below:

XII

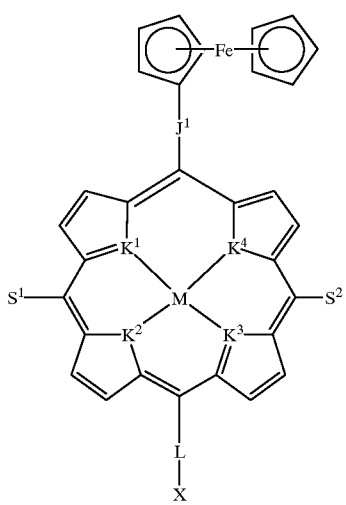

XIII

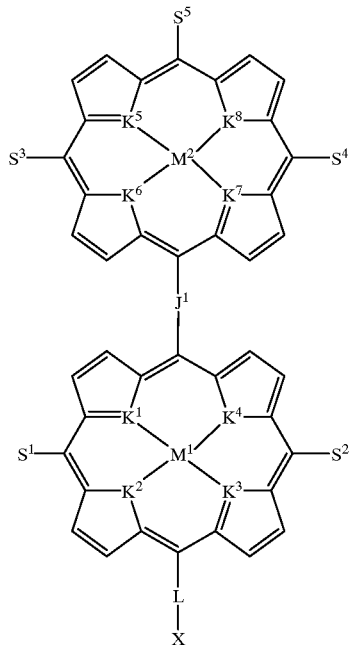

XIV

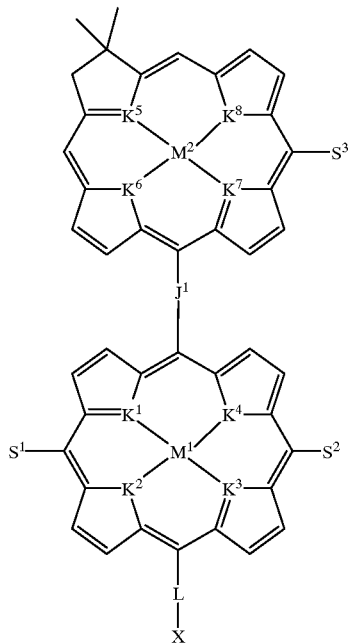

where $K^5$, $K^6$, $K^7$, and $K^8$ are independently selected from the group consisting of N, O, S, Se, Te, and CH; $S^2$ and $S^3$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts, and $M^2$ is a metal (e.g., Zn, Mg, Cd, Hg, Cu, Ag, Au, Ni, Pd, Pt, Co, Rh, Ir, Mn, B, Al, Ga, Pb, and Sn). These molecules can exist in three different and distinguishable oxidation states. The values of the oxidation states are determined by the metal (M), the substituent(s) ($S^1$, $S^2$, and $S^2$), and the redox-active subunit (e.g. porphyrin, chlorin, or ferrocene).

Even more preferred embodiments include the molecules of Formulas XV, XVI, and XVII.

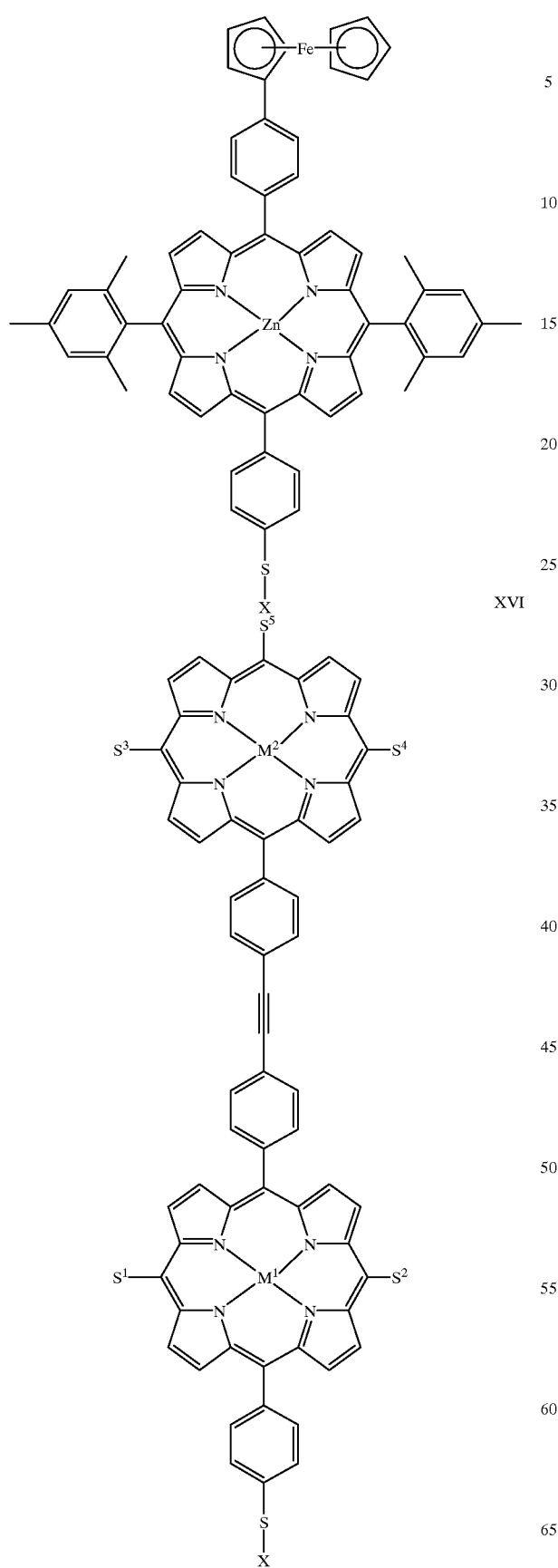
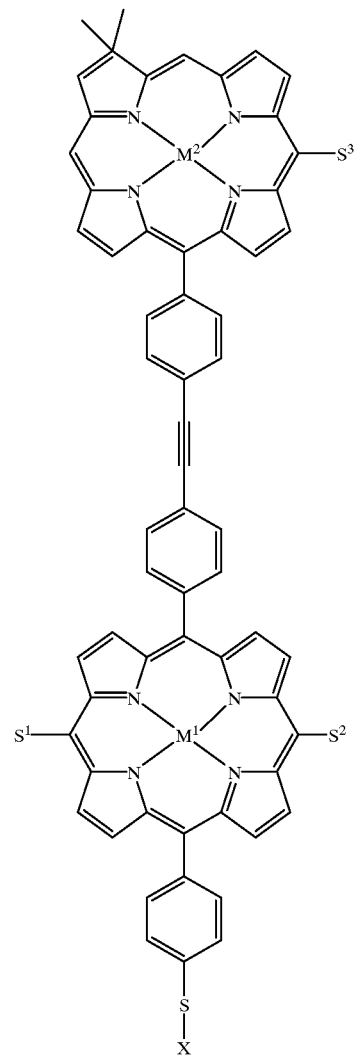
A molecule capable of storing even more information is illustrated in Formula XVIII.
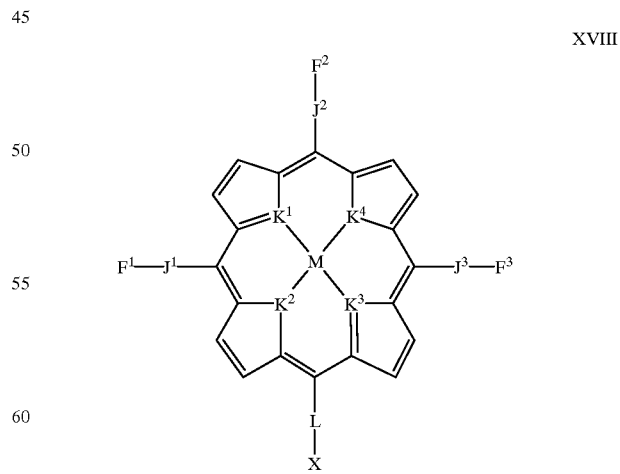
where M is a metal (e.g., Zn, Mg, Cd, Hg, Cu, Ag, Au, Ni, Pd, Pt, Co, Rh, Ir, Mn, B, Al, Ga, Pb, and Sn), $F^1$, $F^2$, and $F^3$ are independently selected ferrocenes or substituted ferrocenes, $J^1$, $J^2$, and $J^3$ are independently selected linkers, $K^1$, $K^2$, $K^3$, and $K^4$ are in dependently selected from the group consisting of N, O, S, Se, Te, and CH; L is a linker; and X is selected from the group consisting of a substrate, a reactive site that can covalently couple to a substrate, and a reactive site that can ionically couple to a substrate. In some embodiments, L—X can be eliminated and replaced with a substituent (i.e., a ferrocene, a substituted ferrocene, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. Preferred substituents provide a redox potential range of less than about 5 volts, preferably less than about 2 volts, more preferably less than about 1 volt. In preferred embodiments, $J^1$, $J^2$, and $J^3$ are selected from the group consisting of 4,4'-diphenylethyne, 4,4'-diphenylbutadiyne, 4,4'-biphenyl, 1-4-phenylene, 4,4'-stilbene, 1,4-bicyclooctane, 4,4'-azobenzene, 4,4'-benzylideneaniline, and 4,4"-terphenyl In certain particularly preferred embodiments, in the molecules of Formula XVIII, $K^1$, $K^2$, $K^3$ and $K^4$ are the same, M is a metal selected from the group consisting of Zn, Mg, Cd, Hg, Cu, Ag, Au, Ni, Pd, Pt, Co, Rh, Ir, Mn, B, Pb, Al, Ga, and Sn, $J^1$, $J^2$, and $J^3$ are the same; and $F^1$, $F^2$, and $F^3$ are all different. One preferred embodiment is a 5 bit molecule illustrated by Formula XIX.

XIX

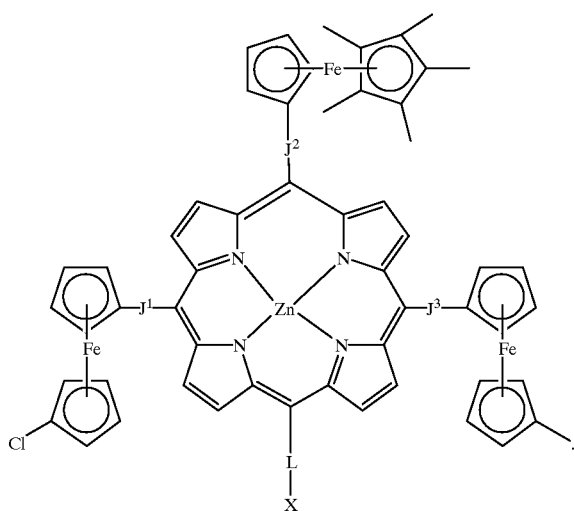

In this example, two oxidation states are determined by the porphyrin, and the remaining three states are determined by the three ferrocenes.

Still another preferred embodiment, includes molecules represented by Formula XX:

XX

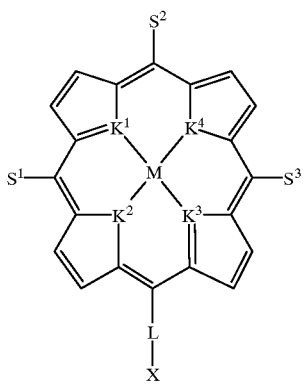

where $K^1$, $K^2$, $K^3$, and $K^4$ are independently selected from the group consisting of N, S, O, Se, Te, and CH; M is a metal or (H,H); $S^1$, $S^2$, and $S^3$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl; L is present or absent and, when present, is a linker; and X is selected from the group consisting of a substrate, a reactive site that can covalently couple to a substrate, and a reactive site that can ionically couple to a substrate. In some embodiments L—X can be eliminated and replaced with a substituent independently selected from the same group as $S^1$ or $S^2$ Preferred substituents ($S^1$, $S^2$, or $S^3$) provide a redox potential range of less than about 2 volts. In some preferred variants M is Zn, Mg, Cd, Hg, Cu, Ag, Au, Ni, Pd, Pt, Co, Rh, Ir, Mn, B, Al, Pb, Ga, or Sn. More preferably M is Zn, Mg, or (H,H). In some preferred variants, S is mesityl, $C_6F_5$, 2,4,6-trimethoxyphenyl, or n-pentyl. In some preferred variants, $S^1$, $S^2$, and $S^3$ are independently CONH(Et), $COCH_3$, or H. In some particularly preferred variants, L—X is absent or present, and when present, L—X is 4-(2-(4-mercaptophenyl)ethynyl)phenyl, 4-mercaptomethylphenyl, 4-hydroselenophenyl, 4-(2-(4-hydroselenophenyl)ethynyl) phenyl, 4-hydrotellurophenyl, or 4-(2-(4-hydrotellurophenyl)ethynyl)phenyl.

In some more preferred embodiments of Formula XX, $S^1$, $S^2$, and $S^3$ are all the same, $K^1$, $K^2$, $K^3$, and $K^4$ are all N; and L is p-thiophenyl. M is then preferably Zn or (H,H). Particularly preferred variants are listed in Table 2.

TABLE 2

Preferred variants of Formula XX.

| Variant | $S^1$ and/or $S^2$ and/or $S^3$ | X | M |
|---|---|---|---|
| 1 | Mesityl | SCONH(Et) | H,H |
| 2 | Mesityl | SCONH(Et) | Zn |
| 3 | Mesityl | $SCOCH_3$ | H,H |
| 4 | Mesityl | $SCOCH_3$ | Zn |
| 5 | Mesityl | SH | Zn |
| 6 | $C_6F_5$ | SCONH(Et) | H,H |
| 7 | $C_6F_5$ | SH | Zn |
| 8 | 2,4,6-trimethoxyphenyl | SCONH(Et) | H,H |
| 9 | 2,4,6-trimethoxyphenyl | SCONH(Et) | Zn |
| 10 | n-pentyl | SCONH(Et) | H,H |
| 11 | n-pentyl | SH | Zn |

In particularly preferred variants of the compounds indicated in Table 3, L can be a phenyl.

Other preferred molecules are illustrated by Formula XXI:

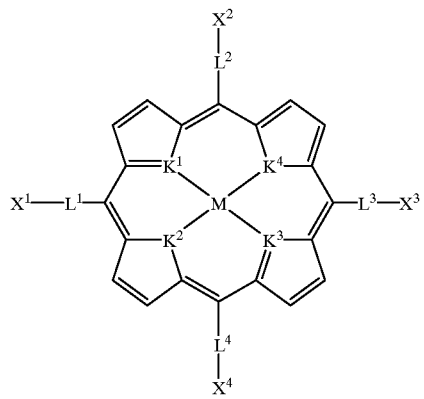

XXI where $K^1$, $K^2$, $K^3$, and $K^4$ are independently selected from the group consisting of N, O, S, Se, Te, and CH; M is a metal or (H,H); $L^1$, $L^2$, and $L^3$, and $L^4$ are independently present or absent and, when present, are linkers; and $X^1$, $X^2$, $X^3$, and $X^4$ are independently selected from the group consisting of a substrate, a reactive site that can covalently couple to a substrate, and a reactive site that can ionically couple to a substrate. In some embodiments L—X can be eliminated and/or replaced with a substituent independently selected from various substituents such as aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. Preferred substituents provide a redox potential range of less than about 5 volts, preferably less than about 2 volts, more preferably less than about 1 volt.

In preferred embodiments, M is Zn, Mg, Cd, Hg, Cu, Ag, Au, Ni, Pd, Pt, Co, Rh, Ir, Mn, B, Pb, Al, Ga, or Sn and in some embodiments, M is more preferably Zn, Mg, or (H,H). In certain preferred embodiments, $L^1$—$X^1$, $L^2$—$X^2$, $L^3$—$X^3$, and $L^4$—$X^4$ are independently present or absent and, when present, are independently 3-mercaptophenyl, 3-mercaptomethylphenyl, 3-(2-(4-mercaptophenyl)ethynyl)phenyl, 3-(2-(3-mercaptomethylphenyl)ethynyl)phenyl, 3-hydroselenophenyl, 3-hydroselenomethylphenyl, 3-(2-(4-hydroselenophenyl)ethynyl)phenyl, 3-(2-(3-hydroselenophenyl)ethynyl)phenyl, 3-hydrotellurophenyl, 3-hydrotelluromethylphenyl and 3-(2-(4-hydrotellurophenyl)ethynyl)phenyl, or 3-(2-(3-hydrotellurophenyl)ethynyl)phenyl Particularly preferred variants of Formula XXI are illustrated by the compounds of Formulas XXII, XXIII, and XXIV:

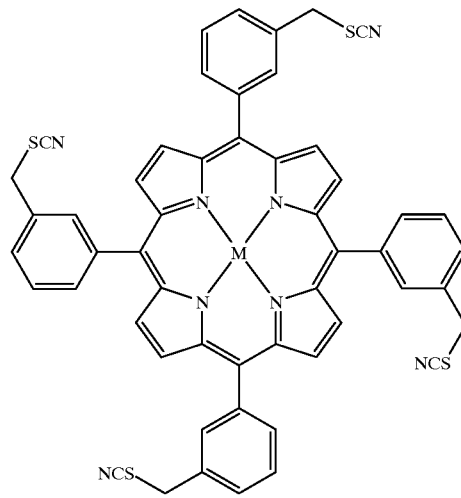

XXII

M = H,H; Zn

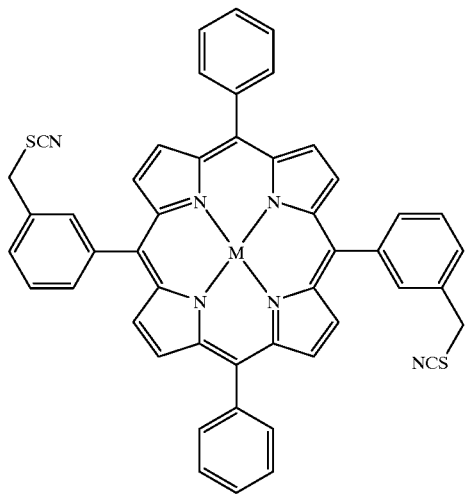

XXIII

M = H,H; Zn

XXIV

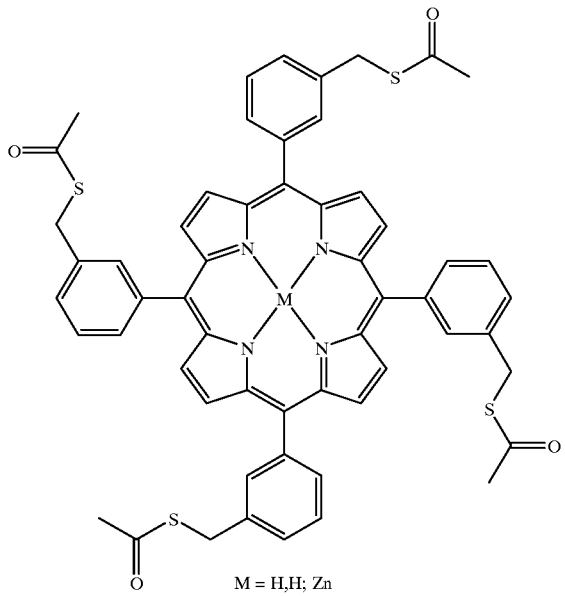

M = H,H; Zn

Using the examples and teaching provided herein, one of skill can produce a virtually limitless supply of data storage molecules suitable for use in the SHMU storage format of the apparatus of this invention.

C) Dynamic Hole Multi-unit (DHMU) Storage

In another embodiment, the data storage medium used in the devices of this invention includes one or more molecules that act as a dynamic multi-unit (DHMU) molecular memory storage. In one embodiment, such a storage molecule comprises a porphyrinic macrocycle containing at least two porphyrins of equal energies held apart from each other at a spacing less than about 50 Å such that said molecule has an odd hole oxidation state permitting the hole to hop between said two porphyrins and wherein said odd hole oxidation state is different from and distinguishable from another oxidation state of said porphyrinic macrocycle.

The basic unit of a dynamic hole multi-unit storage molecule is illustrated by Formula XXV.

$$P^1\text{—}P^2\text{—}P^3 \qquad \text{XXV.}$$

where $P^2$ is a redox-active subunit having an oxidation potential higher than $P^1$ or $P^3$ and $P^1$ and $P^3$ have the essentially the same oxidation potential. Thus, when an electron is withdrawn from the molecule, the "hole" does not reside on $P^1$ and, instead, "hops" from $P^1$ to $P^3$ and back again. Data are stored in the "hopping" hole. As will be explained below, this permits interrogation of the molecule without resetting the state of the molecule. Accordingly, a "read" can be performed without a "refresh".

One particularly preferred DHMU storage molecule is illustrated by Formula XXVI:

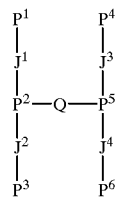

XXVI where $P^1$, $P^3$, $P^4$, and $P^6$ are independently selected porphyrinic macrocycles; $J^1$, $J^2$, $J^3$, and $J^4$ are independently selected linkers that permit electron transfer between the porphyrinic macrocycles; $P^2$ and $P^5$ are independently selected metallo-free porphyrinic macrocycles; and Q is a linker. Preferred "Q" linkers include, but are not limited to linkers such as 1,4-bis(4-terphen-4"-yl)butadiyne or a tetrakis(arylethyne), or linkers comprised of 1,12-carboranyl ($C_2B_{10}H_{12}$), 1,10-carboranyl ($C_2B_8H_{10}$), [n]staffane, 1,4-cubanediyl, 1,4-bicyclo[2.2.2]octanediyl, phenylethynyl, or p-phenylene units.

One particularly preferred variant of this molecule is illustrated in Formula XVII.

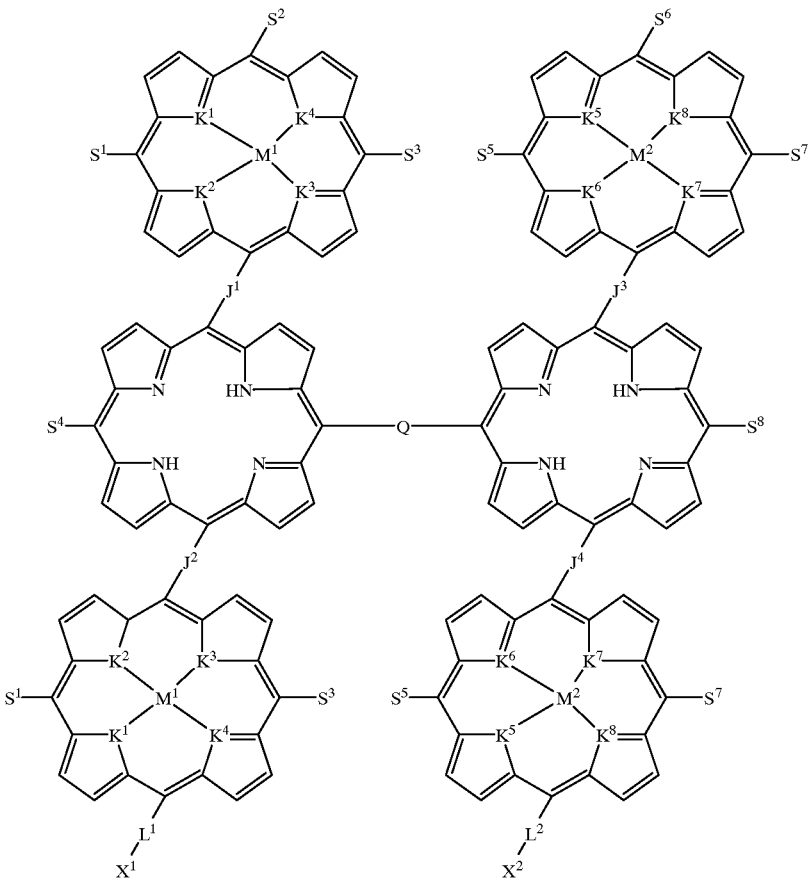

where $M^1$ and $M^2$ are independently selected metals; $S^1$, $S^2$, $S^3$, $S^4$, $S^5$, $S^6$, $S^7$, and $S^8$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl; $K^1$, $K^2$, $K^3$, $K^4$, $K^5$, $K^6$, $K^7$, and $K^8$ are independently selected from the group consisting of are independently selected from the group consisting of N, O, S, Se, Te, and CH; $L^1$ and $L^2$ are independently selected linkers; and $X^1$ and $X^2$ are independently selected from the group consisting of a substrate, a reactive site that can covalently couple to a substrate, and a reactive site that can ionically couple to a substrate. Preferred substituents ($S^1$, $S^2$, $S^3$, $S^4$, $S^5$, $S^6$, $S^7$ or $S^8$) provide a redox potential range of less than about 5 volts, more preferably less than about 2 volts, and most preferably less than about 1 volt. In some embodiments L—X can be eliminated and replaced with a substituent independently selected from the same group as $S^1$–$S^8$.

In particularly preferred DHMU storage molecules of Formula XVII, $S^1$, $S^2$, $S^3$, $S^5$, $S^6$, $S^7$, are the same, $S^4$ and $S^8$ are the same; $K^1$, $K^2$, $K^3$, $K^4$, $K^5$, $K^6$, $K^7$, and $K^8$ are the same, $J^1$, $J^2$, $J^3$ and $J^4$ are the same; and $M^1$ and $M^2$ are different. A preferred species is illustrated by Formula XXVIII:

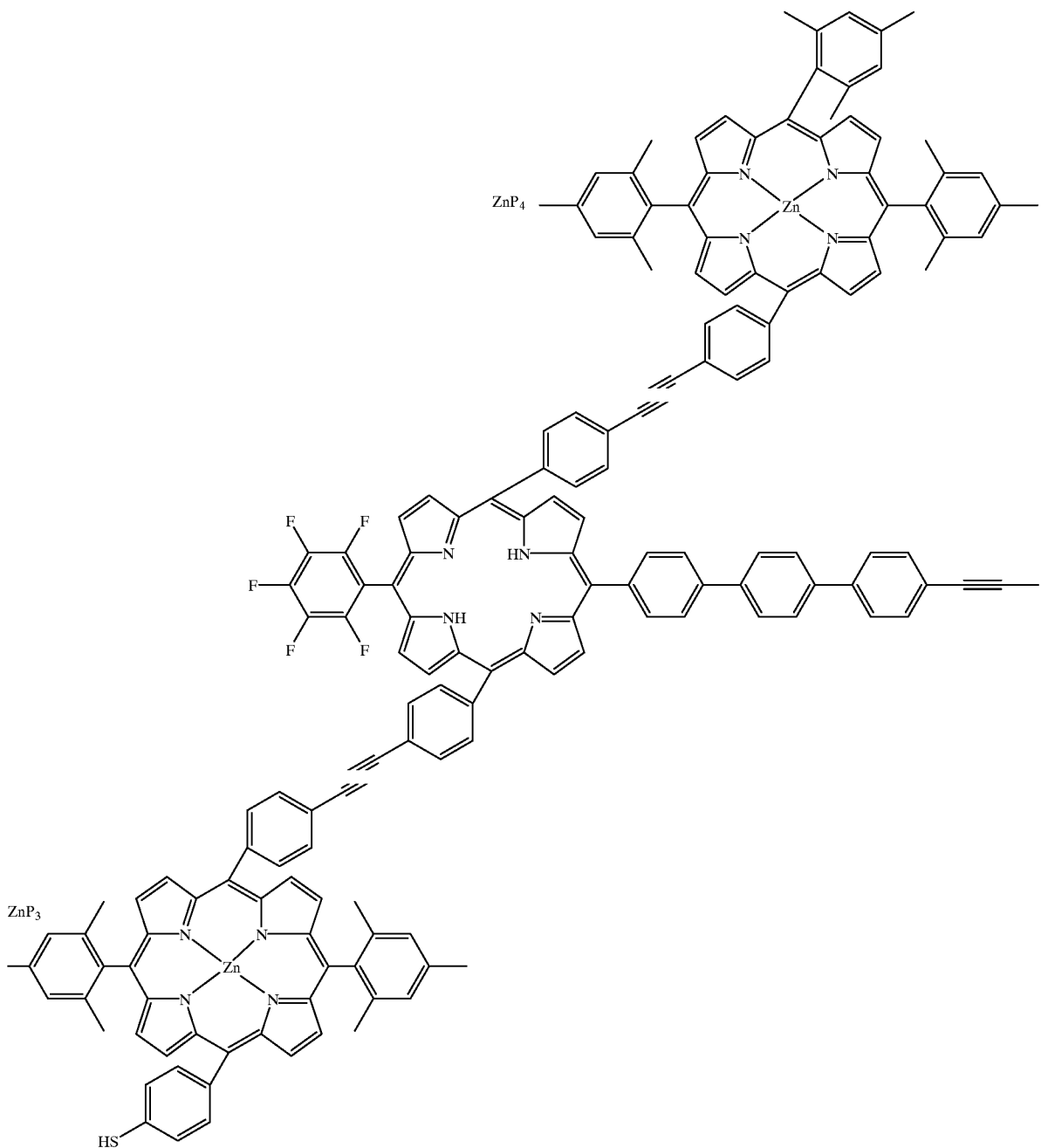
XVIII

-continued

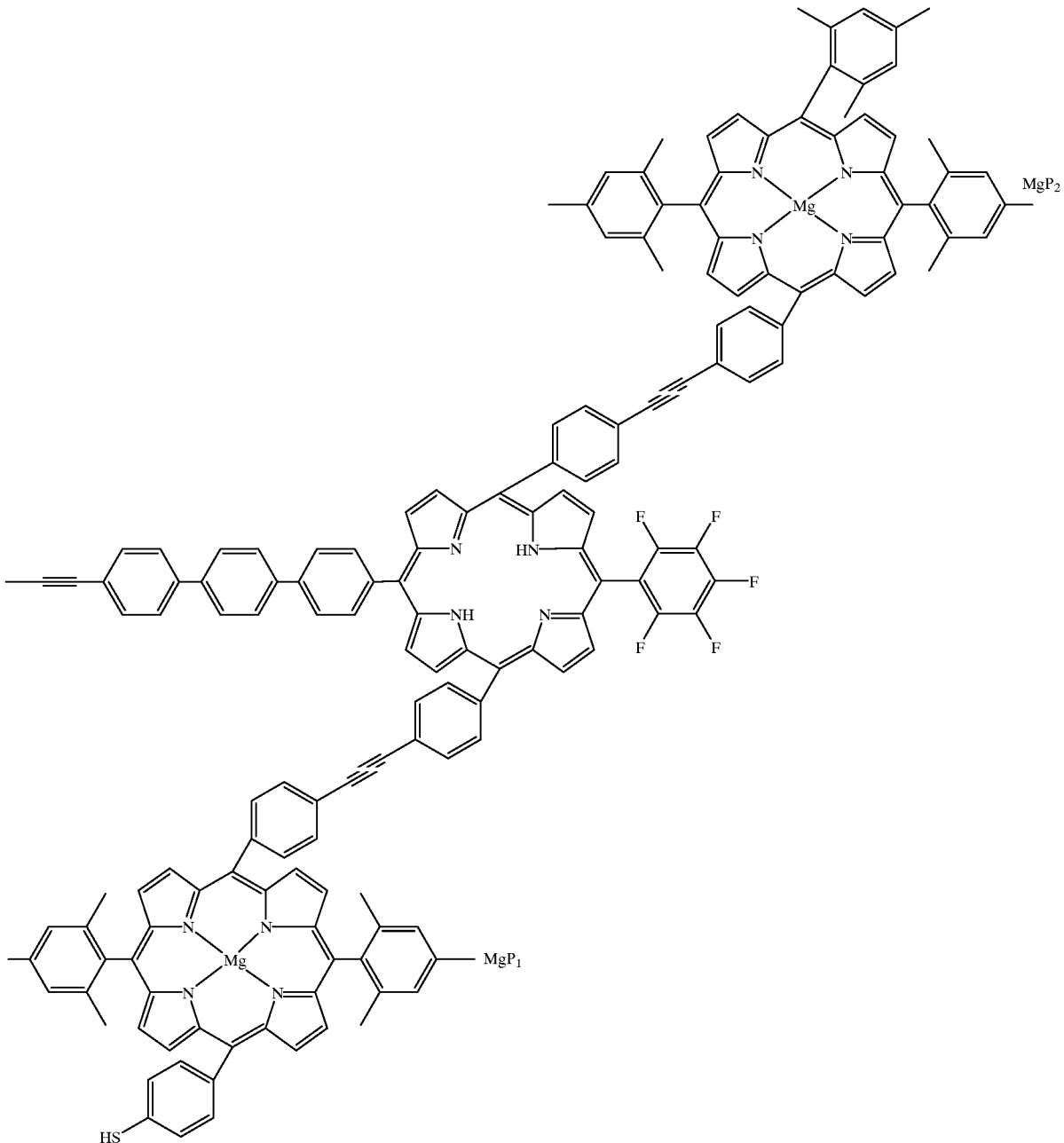

The overall architecture of these molecule consists of linear trimers (e.g. like Formula XXV) joined together by a linker (e.g., a 1,4-bis(4-terphen-4"-yl)butadiyne or a tetrakis (arylethyne) unit). In some preferred embodiments, trimers consist of metallo-free base-metallo porphyrins (see, e.g., Formula XVIII).

In preferred embodiments, the peripheral porphyrins in a given trimer have identical metals and substituents engendering equivalent redox potentials. The core free base porphyrins each have perfluorophenyl substituents to render the porphyrins more resistant to oxidation. The central linker (e.g., a 1,4-bis(4-terphen-4"-yl)butadiyne or a tetrakis (arylethyne)) serves as a structural unit to hold the trimers together. In addition, each porphyrin bears a linker (e.g., a p-thiophenol unit) for assembly on electroactive surfaces.

This nanostructure, although complex in appearance, is in fact substantially smaller than other nanostructures synthesized and known in the prior art.

Information is stored in the dynamic hole memory via oxidation of the porphyrinic macrocycles as described above for the static-hole memory. However, there are certain key differences that distinguish the two types of memory elements that are illustrated by reference to Formula XVIII. In compounds of Formula XVIII, the oxidation potentials of the two Mg porphyrins are essentially identical to one another (the difference is less than thermal energy at room temperature), as is also the case for the two Zn porphyrins. Thus, oxidation results in the following sequence of states: [$MgP_1^+$, others neutral], [$MgP_1^+$, $MgP_2^+$, both $ZnP_3$ and $ZnP_4$ neutral], [$MgP_1^+$, $MgP_2^+$, $ZnP_3^+$, $ZnP_4$], [$MgP_1^+$, $MgP_2^+$, $ZnP_3^+$, $ZnP_4^+$], [$MgP_1^{++}$, $MgP_2^+$, $ZnP_3^+$, $ZnP_4^+$], and so forth until two holes have been removed from each metalloporphyrin, i.e. [$MgP_1^{++}$, $MgP_2^{++}$, $ZnP_3^{++}$, $ZnP_4^{++}$]. Thus, up to eight holes can again be stored in the nanostructure.

However, the cases where one hole (or three holes) resides on either the Mg or the Zn porphyrins are unique. For these odd-hole oxidation states, the hole(s) rapidly hop between the two metalloporphyrins (100's of KHz to 100's of MHz, depending on the type of porphyrin. In contrast, when each Mg or Zn porphyrin contains the same number of holes, no hopping can occur.

Figure 5:
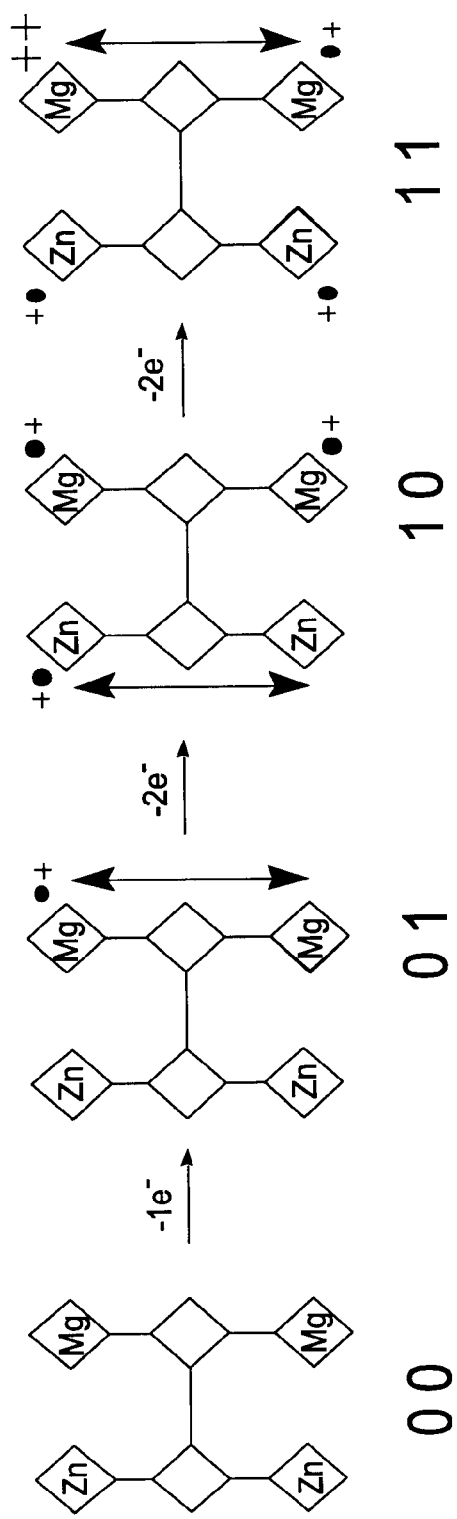
FIG. 5 illustrates the encoding of a prototypical DHMU storage molecule using hole-hopping states (the double-headed arrows indicate hole hopping).

In a preferred embodiment, information is stored only via the hole-hopping states of the multiporphyrin nanostructure, hence the designation "dynamic-hole" multi-unit storage. The encoding of a prototypical DHMU storage cell using the hole-hopping states is shown in FIG. 5 (the double-headed arrows indicate hole hopping). The synthetic methodologies already established permit extension of the architecture via addition of other trimeric units wherein the oxidation potential of the metalloporphyrin is different from that of the others, thus increasing the dynamic range of the basic memory element beyond that shown.

V. Synthesis and Characterization of Storage Medium Molecule(s)

A) Designing Oxidation States Into the Storage Medium Molecule(s)

Control over the hole-storage and hole-hopping properties of the redox-active units of the storage molecules used in the memory devices of this invention allows fine control over the architecture of the memory device.

Such control is exercised through synthetic design. The hole-storage properties depend on the oxidation potential of the redox-active units or subunits that are themselves or are that are used to assemble the storage media used in the devices of this invention. The hole-storage properties and redox potential can be tuned with precision by choice of base molecule(s), associated metals and peripheral substituents (Yang et al. (1999) *J. Porphyrins Phthalocyanines,* 3: 117–147).

For example, in the case of porphyrins, Mg porphyrins are more easily oxidized than Zn porphyrins, and electron withdrawing or electron releasing aryl groups can modulate the oxidation properties in predictable ways. Hole-hopping occurs among isoenergetic porphyrins in a nanostructure and is mediated via the covalent linker joining the porphyrins (Seth et al. (1994) *J. Am. Chem. Soc.,* 116: 10578–10592, Seth et al. (1996) *J. Am. Chem. Soc.,* 118: 11194–11207, Strachan et al. (1997) *J. Am. Chem. Soc.,* 119: 11191–11201; Li et al. (1997) *J. Mater. Chem.,* 7: 1245–1262, Strachan et al. (1998) *Inorg. Chem.,* 37: 1191–1201, Yang et al. (1999) *J. Am. Chem. Soc.,* 121: 4008–4018). Hole-hopping is not expected in the SHMU storage molecule(s) because each porphyrin has a different oxidation potential. Hole-hopping is expected among isoenergetic porphyrins in the DHMU molecule(s).

We have studied hole-hopping phenomena extensively in related nanostructures in solution. We also have prepared and characterized the electrochemical properties of a library of monomeric Mg or Zn porphyrins bearing diverse aryl groups (Yang et al. (1999) *J. Porphyrins Phthalocyanines,* 3: 117–147). The effects of metals on metalloprophyrin oxidation potentials are well known (Fuhrhop and Mauzerall (1969) *J. Am. Chem. Soc.,* 91: 4174–4181). Together, these provide a strong foundation for designing devices with predictable hole-storage and hole-hopping properties.

The design of compounds with predicted redox potentials is well known to those of ordinary skill in the art. In general, the oxidation potentials of redox-active units or subunits are well known to those of skill in the art and can be looked up (see, e.g., *Handbook of Electrochemistry of the Elements*). Moreover, in general, the effects of various substituents on the redox potentials of a molecule are generally additive. Thus, a theoretical oxidation potential can be readily predicted for any potential data storage molecule. The actual oxidation potential, particularly the oxidation potential of the information storage molecule(s) or the information storage medium can be measured according to standard methods. Typically the oxidation potential is predicted by comparison of the experimentally determined oxidation potential of a base molecule and that of a base molecule bearing one substituent in order to determine the shift in potential due to that particular substituent. The sum of such substituent-dependent potential shifts for the respective substituents then gives the predicted oxidation potential.

B) Synthesis of Storage Medium Molecules

The basic synthetic methodologies used to construct the storage medium molecules of this invention are described in Prathapan et al. (1993) *J. Am. Chem. Soc.,* 115: 7519–7520, Wagner et al. (1995) *J. Org. Chem.,* 60: 5266–5273, Nishino et al. (1996) *J. Org. Chem.,* 61: 7534–7544, Wagner et al. (1996) *J. Am. Chem. Soc.,* 118: 11166–11180, Strachan et al. (1997) *J. Am. Chem. Soc.,* 119: 11191–11201, and Li et al. (1997) *J. Mater. Chem.,* 7: 1245–1262. These papers describe various strategies for the synthesis of a number of multi-porphyrin (porphyrinic macrocycle) compounds. More particularly, these papers which focus on light capture, energy funneling, and optical gating, has led to the preparation of nanostructures containing up to 21 covalently linked porphyrins (Fenyo et al. (1997) *J. Porphyrins Phthalocyanines,* 1: 93–99, Mongin et al. (1998) *J. Org. Chem.,* 63: 5568–5580, Burrell and Officer (1998) *Synlett* 1297–1307, Mak et al. (1998) *Angew. Chem. Int. Ed.* 37: 3020–3023, Nakano et al. (1998) *Angew. Chem. Int. Ed.* 37: 3023–3027, Mak et al. (1999) *Chem. Commun.,* 1085–1086). Two-dimensional architectures, such as molecular squares (Wagner et al. (1998) *J. Org. Chem.,* 63: 5042–5049), T-shapes (Johnson, T. E. (1995), Ph.D. Thesis, Carnegie Mellon University), and starbursts (Li et al. (1997) *J. Mater. Chem.,* 7: 1245–1262) all comprised of different covalently linked porphyrin constituents, have also been prepared.

In addition, the hole storage and dynamic hole mobility characteristics of the multiporphyrin nanostructures have been investigated in detail during the course of our other studies of these materials (Seth et al. (1994) *J. Am. Chem. Soc.,* 116: 10578–10592, Seth et al. (1996) *J. Am. Chem. Soc.,* 118: 11194–11207, Strachan et al. (1997) *J. Am. Chem. Soc.,* 119: 11191–11201; Li et al. (1997) *J. Mater. Chem.,* 7: 1245–1262, Strachan et al. (1998) *Inorg. Chem.,* 37: 1191–1201, Yang et al. (1999) *J. Am. Chem. Soc.,* 121: 4008–4018).

The general synthetic strategy involves the following approaches: (1) A modular building block synthesis of covalent multiporphyrin nanostructures; and (2) The directed self-assembly of the resulting nanostructures on electrode (e.g. gold electrode) surfaces.

The methods for synthesis, purification, and characterization for the molecular memory molecules (MMMs) generally follow those employed in the modular stepwise synthesis (Lindsey et al. (1994) *Tetrahedron,* 50: 8941–8968) of molecular wires (Wagner et al. (1994) *J. Am. Chem. Soc.,* 116: 9759–9760), optoelectronic gates (Wagner et al. (1996) *J. Am. Chem. Soc.,* 118: 3996–3997) and light-harvesting nanostructures (Prathapan et al. (1993) *J. Am. Chem. Soc.,*

115: 7519–7520, Johnson, T. E. (1995), Ph.D. Thesis, Carnegie Mellon University, Wagner et al. (1996) *J. Am. Chem. Soc.,* 118: 11166–11180, Li et al. (1997) *J. Mater. Chem.,* 7: 1245–1262, and Li et al. (1998) *J. Am. Chem. Soc.,* 120: 10001–10017). In preferred embodiments, the following synthetic methods form the foundation for the building block synthesis of multiporphyrin nanostructures:

(1) A room temperature one-flask synthesis of meso-substituted porphyrins (Lindsey et al. (1987) *J. Org. Chem.* 52: 827–836, Lindsey et al. (1994) *J. Org. Chem.* 59: 579–587, Li et al. (1997) *Tetrahedron,* 53: 12339–12360).

(2) Incorporation of bulky groups around the porphyrin to achieve enhanced solubility in organic solvents (Lindsey and Wagner (1989) *J. Org. Chem.,* 54: 828–836).

(3) A one-flask synthesis of dipyrromethanes, key building blocks in the synthesis of porphyrins bearing 2–4 different meso-substituents (Lee and Lindsey (1994) *Tetrahedron,* 50: 11427–11440, Littler et al. (1999) *J. Org. Chem.,* 64: 1391–1396).

(4) A synthesis of trans-substituted porphyrins without acidolytic scrambling (Littler et al. (1999) *J. Org. Chem.,* 64: 2864–2872).

(5) A 9-step synthesis of porphyrins bearing 4 different meso-substituents (Lee et al. (1995) *Tetrahedron,* 51: 11645–11672).

(6) Mild methods for inserting magnesium (Lindsey and Woodford (1995) *Inorg. Chem.* 34: 1063–1069, O'Shea et al. (1996) *Inorg. Chem.,* 35: 7325–7338) or other metals (Buchler, J. W. In *The Porphyrins;* Dolphin, D. Ed.; Academic Press: New York. 1978; Vol. I, pp. 389–483) into porphyrins.

(7) Efficient Pd-mediated coupling reactions (60–80% yields in 1–2 h at 35° C.) for constructing diphenylethyne linkers joining the porphyrins (Wagner et al. (1995) *J. Org. Chem.,* 60: 5266–5273).

In one embodiment, building blocks are synthesized using methods described by Wagner et al. (1996) *J. Am. Chem. Soc.,* 118: 11166–11180, Strachan et al. (1997) *J. Am. Chem. Soc.,* 119: 11191–11201, Wagner et al. (1996) *J. Am. Chem. Soc.,* 118: 3996–3997, Li et al. (1997) *J. Mater. Chem.,* 7: 1245–1262; Lindsey et al. (1994) *Tetrahedron,* 50: 8941–8968; Wagner et al. (1994) *J. Am. Chem. Soc.,* 116: 9759–9760; Lindsey and Wagner (1989) *J. Org. Chem.,* 54: 828–836; Lee and Lindsey (1994) *Tetrahedron,* 50: 11427–11440; Lee et al. (1995) *Tetrahedron,* 51: 11645–11672; Lindsey and Woodford (1995) *Inorg. Chem.* 34: 1063–1069; and Wagner et al. (1995) *J. Org. Chem.,* 60: 5266–5273.

The synthesis of the molecules that form the basis for the storage molecules (e.g., SHMU storage molecules, DHMU storage molecules, etc.) is performed using a modular building block approach. This approach employs a stepwise synthesis (rather than polymerization) and yields highly purified and well-characterized products. One approach, utilizes a series of redox-active "building blocks" (e.g., a series of monomeric porphyrinic macrocycles or ferrocene constituents) that can be linked to the gold substrate that will serve as one of the electrodes in the chip. Preferred monomeric redox-active units that are prepared have different oxidation potentials that fall in the range from 0 to 1.3 volts.

The two different redox-active units can be linked together to form a basic dimeric architecture. Similarly, two other different redox-active units (e.g. porphyrins) can be linked to form a second dimeric architecture. Then the two dimers can be linked to form a linear, or non-linear, tetrameric architecture consisting of four different types of redox-active units (e.g., porphyrins).

Figure 6:
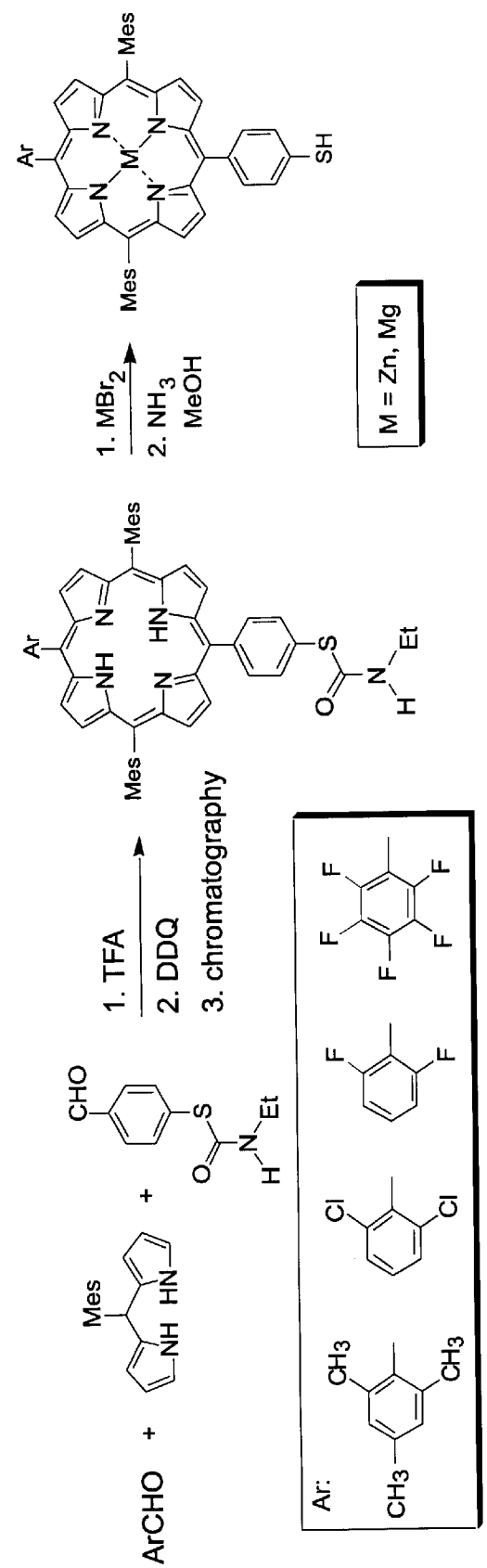
FIG. 6 illustrates porphyrin mono-thiols for attachment to a metal (e.g., gold) electrode.

One example of a preferred synthesis approach is shown in FIG. 6. The reaction of 5-mesityldipyrromethane (Lee and Lindsey (1994) *Tetrahedron,* 50: 11427–11440) with two aldehydes affords three porphyrins, including the desired mono-thiol porphyrin. The latter is metalated with Zn or Mg, and then the thiol protecting group can be removed. Of the various thiol protecting groups (Hsung et al. (1995) *Tetrahedron Lett.,* 36: 4525–4528; Ricci et al. (1977) *J. Chem. Soc. Perkin Transactions I.,* 1069–1073) the S-acetyl or S-(N-ethyl-carbamoyl) group is stable toward the required synthetic conditions yet cleaved easily with methanolic diethylamine. The useful precursor 4-mercaptobenzaldehyde is readily available (Young et al. (1984) *Tetrahedron Lett.,* 25: 1753–1756). The resulting porphyrin mono-thiol can be assembled on a gold surface, or the protected thiol can be deprotected in situ on a gold surface.

Figure 7:
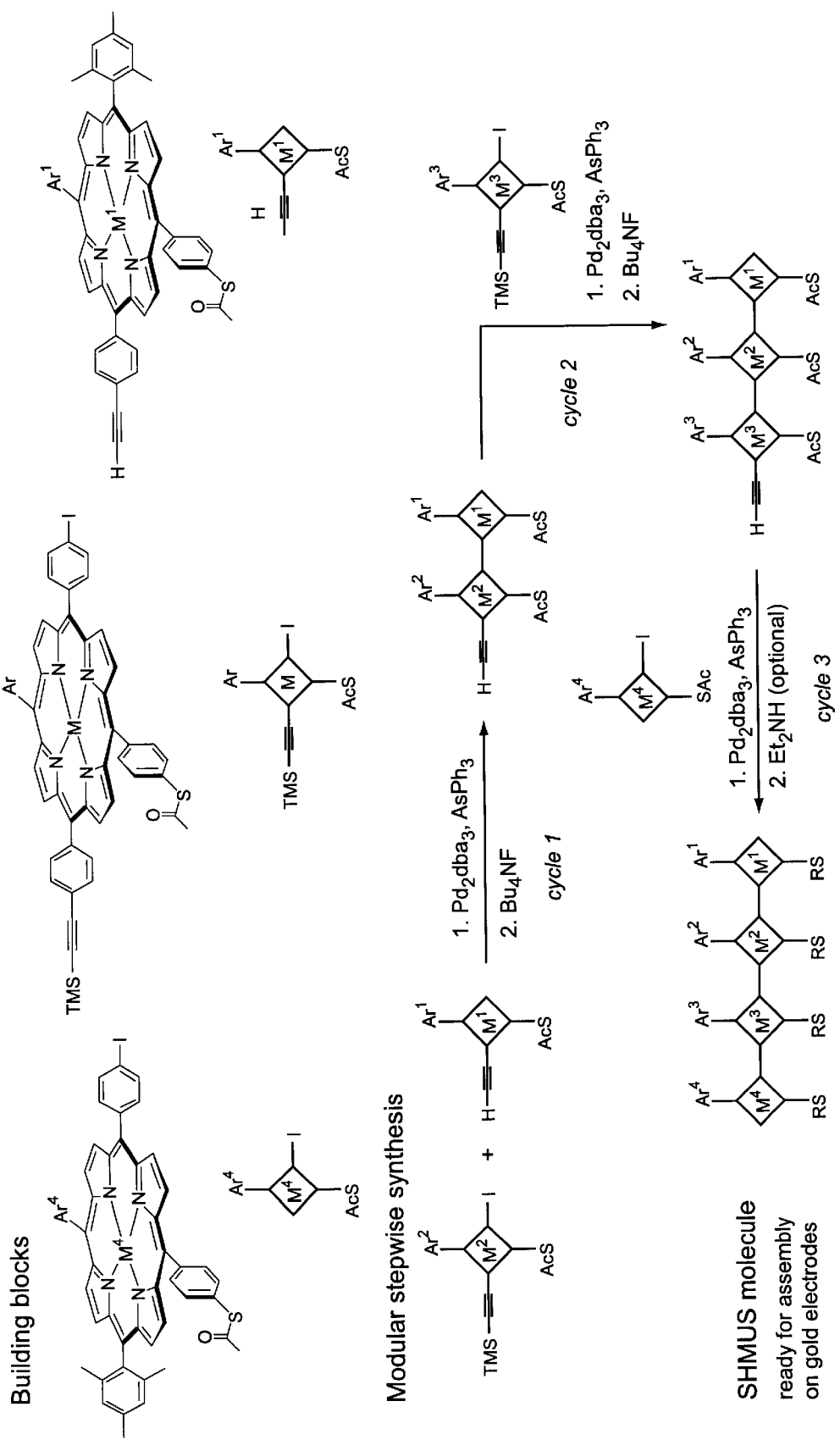
FIG. 7 illustrates the modular synthesis of a SHMU storage molecule.

The synthesis of an SHMU storage molecule is shown in FIG. 7. Four porphyrin building blocks are employed in the synthesis of this nanostructure. Each building block is available via established synthetic routes (either via the route we established for ABCD-porphyrins or via a 3+1 route involving a tripyrrane) (Lee et al. (1995) *Tetrahedron,* 51: 11645–11672). The fundamental methodology for joining the porphyrin building blocks involves Pd-mediated coupling of an ethynyl-porphyrin and an iodo-porphyrin (Wagner et al. (1995) *J. Org. Chem.,* 60: 5266–5273). Our optimized conditions for these coupling reactions afford 60–80% yields in 2–4 h. Purification is achieved using size-exclusion chromatography and characterization is accomplished with laser desorption mass spectrometry (see, e.g., Fenyo et al. (1997) *J. Porphyrins Phthalocyanines,* 1: 93–99). This synthetic route is tolerant toward diverse aryl groups and metals in the porphyrin unit.

The stepwise synthesis makes available the dimeric unit of the SHMU storage molecule upon one cycle of coupling. The dimer will be examined electrochemically. Following cleavage of the S-acetyl protecting group, the thiols may undergo oxidative coupling (forming the disulfides) during handling and processing. Such disulfides can be reduced to regenerate the thiols, or deposited on gold surfaces whereupon reduction in situ yields the bound thiol species. Alternatively, the S-acetyl groups can be cleaved in situ upon exposure to the metal (e.g., gold) surface (Tour et al. (1995) *J. Am. Chem. Soc.,* 117: 9529–9534). A number of porphyrin thiols have been prepared and deposited on metals but not for memory storage applications (see, e.g., Zak et al. (1993) *Langmuir,* 9: 2772–2774; Hutchison et al. (1993) *Langmuir* 9: 3277–3283; Bradshaw et al. (1994) *Gazz. Chim. Ital.* 124, 159–162; Postlethwaite et al. (1995) *Langmuir,* 11: 4109–4116; Akiyama et al. (1996) *Chem. Lett,* 907–908; Uosaki et al. (1997) *J. Am. Chem. Soc.,* 119: 8367–8368; Katz and Willner (1997) *Langmuir,* 13: 3364–3373; Ishida et al. (1998) *Chem. Lett.,* 267–268; Ishida et al. (1998) *Chem. Commun.,* 57–58). Nanostructures having up to 21 porphyrins are readily synthesized.

Figure 8:
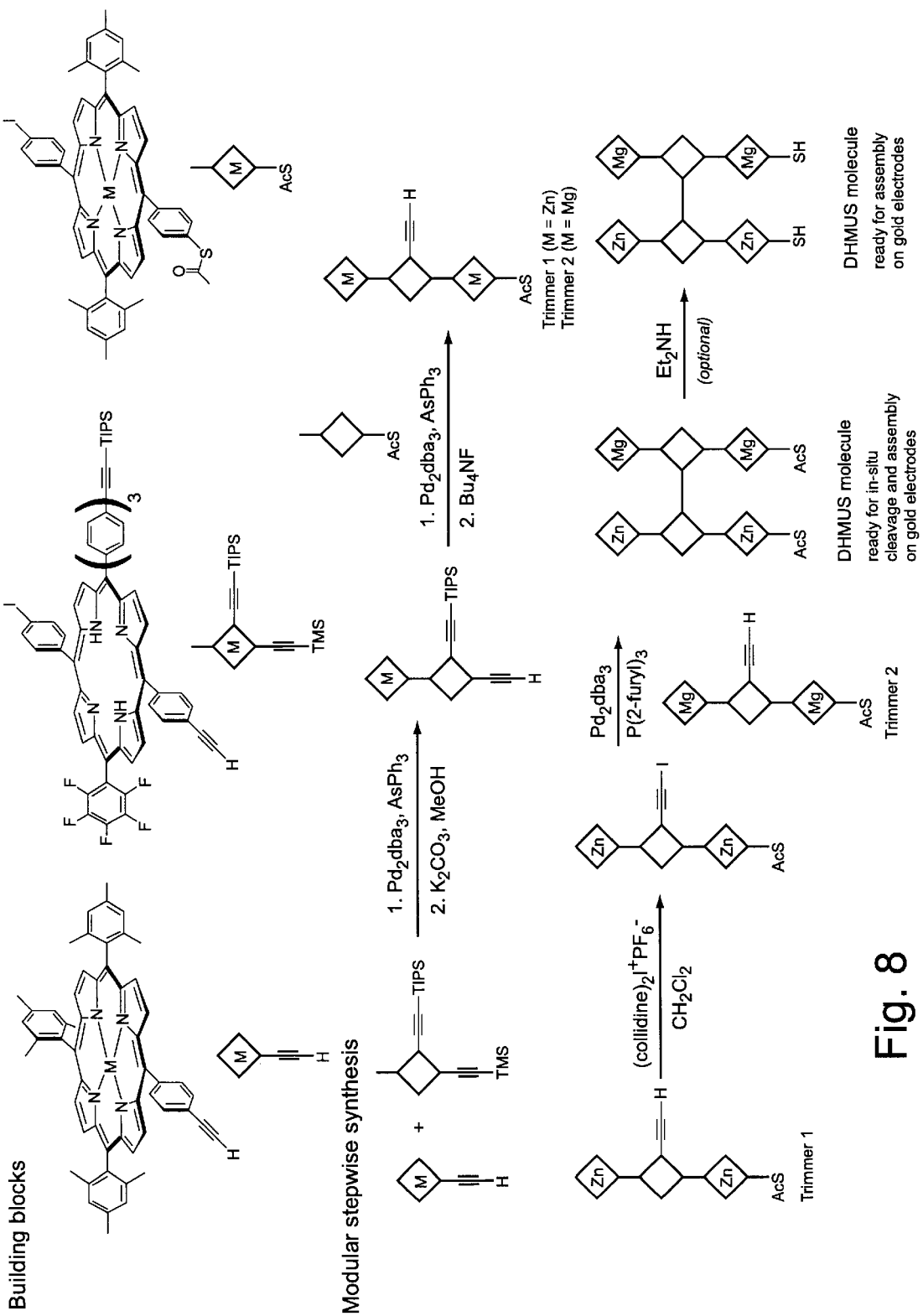
FIG. 8 illustrates a representative synthesis of a DHMU storage molecule. Three porphyrin building blocks are prepared and metalated with magnesium or zinc. The synthetic strategy builds the two arms of the DHMU storage molecule separately, which are then coupled in the penultimate step of the synthesis. Each arm is constructed via two Pd-mediated couplings, yielding the respective trimers. One trimer is iodinated at the ethyne, then joined with the other trimer in a heterocoupling process to form the H-like structure.

A representative synthesis of a DHMU storage molecule is shown in FIG. 8. Three porphyrin building blocks are prepared and metalated with magnesium or zinc. The synthetic strategy builds the two arms of the DHMU storage molecule separately, which are then coupled in the penultimate step of the synthesis. Each arm is constructed via two Pd-mediated couplings, yielding the respective trimers. One trimer is iodinated at the ethyne (Barluenga et al. (1987) *Synthesis,* 661–662; and Brunel and Rousseau (1995) *Tetrahedron Lett.,* 36: 2619–2622) then joined with the other trimer in a heterocoupling process to form the H-like structure. A variety of conditions can be employed for the heterocoupling reaction (Alami and Ferri (1996) *Tetrahedron Lett.,* 37: 2763–2766). We previously showed that Pd-mediated (copper-free) couplings can be employed for homocoupling reactions (Wagner et al. (1995) *J. Org. Chem.,* 60: 5266–5273). Copper-free couplings are preferred to avoid copper insertion in the free base porphyrin. Here the same Pd-mediated coupling is used to perform the heterocoupling. The final step is cleavage of the S-acetyl protecting group, which proceeds in methanolic $Et_2NH$. Such conditions do not alter any of the other functionalities in the molecule. Alternatively, the S-acetyl groups can be cleaved in situ upon exposure to the metal (e.g., gold) surface (Tour et al. (1995) *J. Am. Chem. Soc.,* 117: 9529–9534).

Using the synthesis strategies exemplified here and in the Examples, one of ordinary skill in the art can routinely produce relatively complex data storage molecules for use in the devices of this invention.

C) Characterization of the Storage Media

The storage media molecule(s), once prepared, can be characterized according to standard methods well known to those of skill in the art. The characterization of multiporphyrin nanostructures has been described (see, e.g., Strachan et al. (1997) *J. Am. Chem. Soc.,* 119: 11191–11201; Wagner et al. (1996) *J. Am. Chem. Soc.,* 118: 3996–3997; Li et al. (1997) *J. Mater. Chem.,* 7: 1245–1262; Seth et al. (1996) *J. Am. Chem. Soc.,* 118: 11194–11207; Seth et al. (1994) *J. Am. Chem. Soc.,* 116: 10578–10592). In a preferred embodiment, the electrochemical studies include cyclic and square-wave voltammetry to establish the redox potentials of the monomeric and multi-unit constituents of the storage media. Bulk electrochemical oxidations are performed on each of the storage materials to assess the hole-storage capabilities and the stability. Absorption and vibrational spectroscopic methods are used to assess the structural and electronic properties of both the neutral and oxidized materials. Electron paramagnetic resonance techniques are used to probe the hole-storage and hole-mobility characteristics of the oxidized storage molecules. Using the above-identified techniques, benchmarks for the expected performance characteristics of a storage molecule (e.g., oxidation potentials, redox reversibility, dynamic hole-mobility characteristics, etc.) can be ascertained.

D) Self-assembly of the Storage Medium Molecules on Target Substrates

In preferred embodiments, the storage molecules comprising the storage medium are designed to self-assemble on a substrate (e.g. a metal such as gold). The disk-like structure of the porphyrin macrocycles engenders self-assembly. Self-assembled monolayers of porphyrins on solid substrates are well known and have been extensively studied (see, e.g., Schick et al. (1989) *J. Am. Chem. Soc.,* 111: 1344–1350, Mohwald et al. (1986) *Thin Solid Films,* 141: 261–275).

To exert control over the pattern of self-assembly, reactive sites (e.g. thiols) or linkers bearing active sites are incorporated into the storage molecules (nanostructures). The reactive sites bind to the target (e.g. gold electrode) surface giving an organized self-assembled structure. In the case of porphyrins with thiol linkers attached to the meso-positions, the porphyrins arrange in upright orientations. Non-covalent interactions between storage molecules are typically weak, particularly when bulky aryl groups are attached to each of the porphyrins.

VI. Writing to the Storage Device

In preferred embodiments of the data storage devices of this invention, information is written to a particular memory location via application of a potential of the requisite value and temporal duration at the appropriate working and reference electrode(s) to achieve the desired digital value. The information can be erased via application of a potential of the opposite sign.

The writing process is illustrated with respect to storage of data in a static hole multi-unit storage molecule (SHMU storage molecule). One particular such molecular memory is illustrated by Formula IX and the writing process is summarized below in Table 3.

Figure 9:
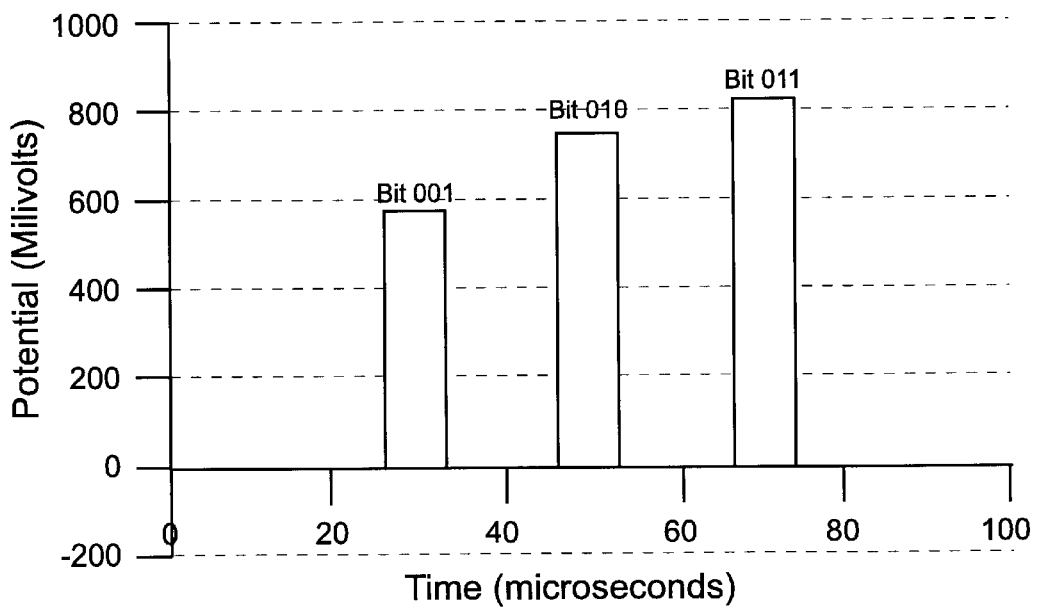
FIG. 9 illustrates writing to a molecular memory of this invention. In preferred embodiments, this is accomplished through the application of very short (e.g., microsecond) pulses applied at a voltage sufficient to oxidize a storage medium (e.g., a porphyrin) to the appropriate redox state as summarized in this figure. Thus, each redox state of the composite multiunit nanostructure (e.g. porphyrinic array) can be independently accessed to provide one bit of resolution. This can be accomplished via the electrochemical oxidation of the molecule in stepwise increments.

As shown in Table 3, each porphyrin has two redox processes, each of which is separated by at least 150 mV. To activate bit 001, a potential greater than 0.38 V (but less than 0.51 V) would be applied to the memory element to oxidize the magnesium porphyrin to its first oxidation state. The other porphyrins in the SHMU storage molecule could then be sequentially oxidized through the various redox states to provide the different bits. In preferred embodiments, this is accomplished through the application of very short (e.g., microsecond) pulses applied at a voltage sufficient to oxidize a porphyrin to the appropriate redox state. This process is summarized in FIG. 9. Thus, each redox state of the composite porphyrinic nanostructure can independently accessed to provide one bit of resolution. This can be accomplished via the electrochemical oxidation of the molecule in stepwise increments.

TABLE 3

Redox properties of model metalloporphyrins (MP).

| Bit | Redox process | $E^0$ (V vs. Ag/AgCl) |
|---|---|---|
| 000 | All redox components in neutral state | |
| 001 | $MgPZnP \leftrightarrow MgP^+ZnP + 1\ e^-$ | 0.38 |
| 010 | $MgP^+ZnP \leftrightarrow MgP^+ZnP^+ + 1\ e^-$ | 0.51 |
| 011 | $MgP^+ZnP^+ \leftrightarrow MgP^{2+}ZnP^+ + 1\ e^-$ | 0.71 |

There is a great advantage to the small size of each memory element, which is essentially a modified electrode surface. When each memory element is reduced to submicron dimensions, the area of the surface allows the presence of only a few hundred data storage (e.g., porphyrin) molecules. Using Faraday's law, Q=nFN (where Q equals the total charge, n equals the number of electrons per molecule, F is 96,485 Coulombs/mole and N is the number of moles of electroactive species present), it can be determined that only a small charge ($1.6 \times 10^{-16}$ C; if passed in 1 μs, would result in a current of roughly 160 pA) must pass in order to change the electrochemical charge corresponding to each bit.

Additionally, the intrinsic limitation to the speed of most electrochemical experiments lies in the time required to charge the electrode to the appropriate potential (the charging current, which has a time dependence of exp(–t/RC)). Since the capacitance of the electrode is directly proportional to its area, miniaturization of each element of the system to submicron dimensions will greatly increase its speed. For example, a square gold electrode with 0.1 μm dimensions would have a capacitance of approximately $2 \times 10^{-19}$F, leading to an RC time constant of only 2 picoseconds. For this reason, electrode charging currents should be insignificant in determining the ultimate performance of these devices.

The voltage used to write the data can be derived from any of a wide variety of sources. In a simple embodiment, the voltage can simply be the output from a power supply. However, in preferred embodiments, the voltage will be the output from some element of an electronic circuit. The voltage can be a signal, the representation of a logic state, the output from a gate, from an optical transducer, from a central processing unit, and the like. In short, virtually any voltage source that can be electrically coupled to the devices of this invention can be used to write data to the storage media therein.

VII. Reading From the Storage Device

The storage device(s) of this invention can be read according to any of a wide variety of methods well known to those of ordinary skill in the art. Essentially any method of detecting the oxidation state of a compound can be utilized in the methods of this invention. However, where the readout is destructive of the state of the memory cell(s) (e.g in certain SHSU or SHMU memories), the read will preferably be followed by a refresh to reset the oxidation state of the storage cell.

In particularly preferred embodiments, the storage medium 102 of a storage cell 100 is set to neutral (e.g., 0 potential for the system, but which might not be at true zero voltage with respect to ground) using the working electrode. The oxidation state of the memory cell is then set by changing the potential at the reference electrode 103 (e.g. by setting the reference electrode negative to the desired voltage). The oxidation state of the storage cell is then measured (e.g. using sinusoidal voltammetry) via the working electrode 101. In this preferred format, the oxidation state is assayed by measuring current. By measuring current at the working electrode 101 and setting the state with the reference electrode 103, the measurement is not made at the place the potential is applied. This makes it far simpler to discriminate the oxidation state. If the potential were applied to the electrode through which the current was measured unnecessary noise would be introduced into the system.

A) Reading From Static Hole Storage Media

In the case of static hole storage media (e.g. SHSU and SHMU), the reading of information from a particular memory location is achieved extremely rapidly by sweeping a potential over the full range used to establish the dynamic range of the storage element. The fidelity of the measurement is dependent on how well the oxidation state of the individual storage element can be determined. Traditionally, electrochemical methods could only improve the signal to noise ratio by discriminating the faradaic signal from the background components in the time domain through application of pulse waveforms (i.e., differential pulse polarography, square wave voltammetry). These methods discriminate the faradaic current from the charging current in the time domain, since charging currents decay much more rapidly than the faradaic current (exp(-t/RC) vs $t^{-\frac{1}{2}}$, respectively). However, the analytical faradaic current is not totally discriminated from the charging current, and most of the signal is discarded because sampling is done late in the pulse cycle.

Figure 10:
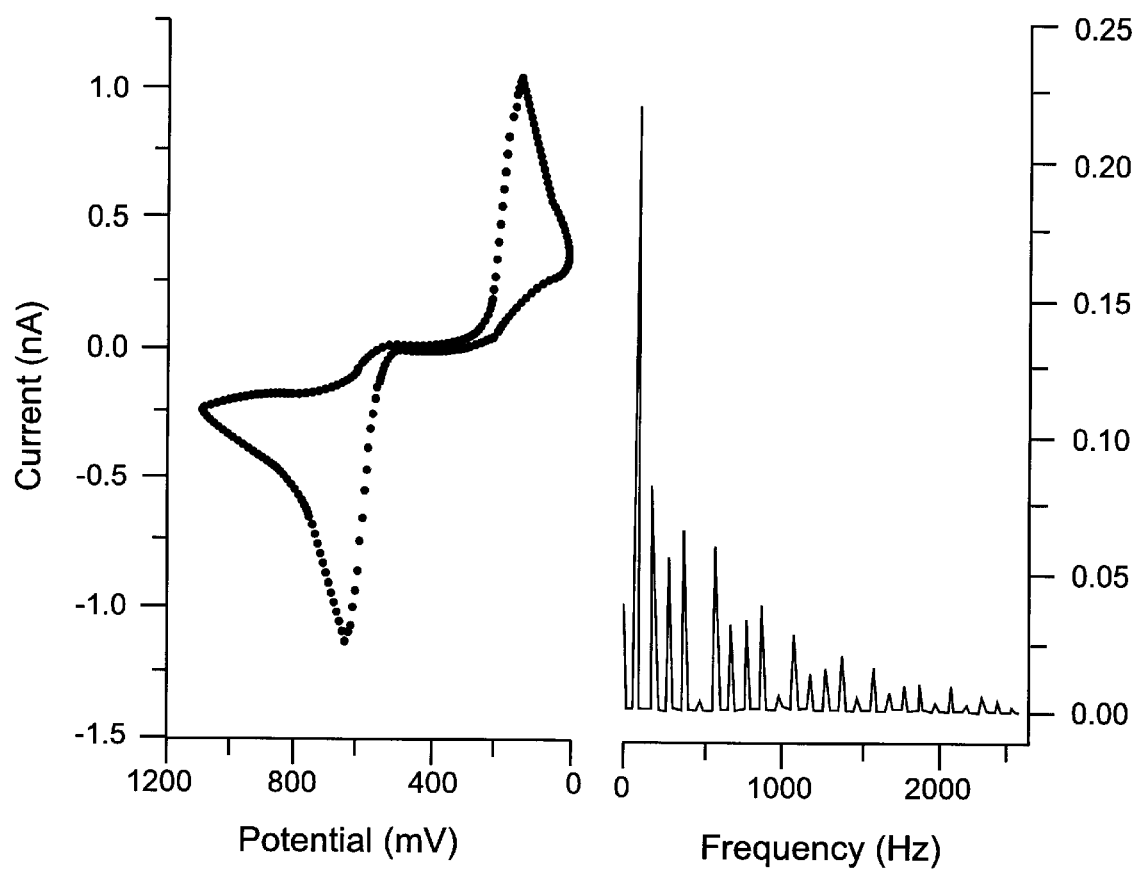
FIG. 10 illustrates a frequency domain spectrum of the faradaic SV response. Note that the numerous harmonic frequency components depend on many of the same voltammetric parameters (e.g., $E°$, $E_{switch}$, scan rate, number of electrons, etc.) that govern the response observed in cyclic voltammetry, and can be easily isolated in the frequency domain.

More recently, sinusoidal voltammetry (SV) has been shown to have significant advantages over traditional waveforms in an electrochemical experiment (Singhal et al. (1997) Anal. Chem., 69: 1662–1668. For example, the background current resulting from cyclic voltammetry (consisting primarily of charging current) resembles a square wave, which contains significant intensity at both fundamental and odd harmonic frequencies. In contrast, the charging current resulting from sine wave excitation has only one frequency component centered at the fundamental, while the faradaic current is distributed over many frequencies as is illustrated in FIG. 10. This characteristic of sine wave excitation simplifies the electroanalytical measurement, since the signal from each oxidation state can be fine-tuned by "locking-in" on one of the higher frequency harmonics. Ultimately, the speed at which this can be performed is only limited by the kinetics of the redox reaction, which may ultimately lead to megahertz frequency operation.

Since most electrochemical methods rely on differences between the $E_{1/2}$'s ($E_{1/2}$ is the potential at which half of the subject molecules are oxidized or reduced to a particular oxidation state) to differentiate compounds present in a sample and thereby to generate the selectivity for the measurement, this has severely limited the utility of electrochemical methods for the analysis of many complex matrices. In contrast, sinusoidal voltammetry can exploit the vast diversity in electron transfer rates observable at solid electrodes ($k^0$, the rate of electron transfer) can vary over ten orders of magnitude at the same electrode surface) to obtain additional selectivity in the electrochemical measurement.

The composition of the frequency spectrum is extremely dependent on the rate of electron transfer. By adjusting the frequency of the sinusoidal (or other time-varying) excitation waveform, it becomes possible to use this kinetic information as well as the phase information to discriminate between two molecules which have very similar electrochemical properties. For example, this technique has been used for the detection of the direct oxidation of double-stranded DNA at copper electrodes (Singhal and Kuhr (1997) Anal. Chem., 69: 1662–1668). Where this is usually undetectable at conventional electrodes with standard voltammetric techniques, the use of sinusoidal voltammetry allowed the measurement of 1.0 nM double-stranded DNA. The concentration detection limit (S/N=3) for this size of dsDNA at the 6th harmonic is 3.2 pM. When coupled with a low-volume system, such as a monolayer of the adsorbed material, this allows detection of sub-zeptomole ($10^{-21}$ mole) quantities of the storage medium molecule(s) on the surface.

This procedure may ultimately degrade the memory in the absence of a refresh mechanism. The level of degradation will depend on the total number of molecules ultimately used to ensure acceptable fault tolerance. To avoid degradation problems, however, a refresh cycle (a write cycle resetting the memory to the read value) can be inserted immediately after each read cycle is complete.

B) Reading From a Dynamic Hole Storage Medium

The same methods as described above for the static hole storage media can also be used to read dynamic hole storage media. However, the dynamic hole storage media were designed for and afford the unique possibility of interrogating a particular memory location via examination of the impedance of the working electrode. This reading scheme is possible because the impedance is modulated by the hole that hops between the two identical porphyrinic macrocycle units orthogonal to the surface of the electrode. The frequency of hole hopping is different depending on which pair of redox-active subunits is in an odd-hole state (and whether they are in a three-hole or one-hole state). The value of the bit can be read via determination of that frequency. This is most easily accomplished by an impedance measurement (preferably a function of frequency).

The "hole-hopping" state of the porphyrin will determine the conductive state of the molecular monolayer. Since the hole(s) rapidly hop between the two metalloporphyrins in the odd-hole oxidation states at rates which vary from the 100's of KHz to 100's of MHz, depending on the type of porphyrin, it is possible to find these states by the frequency at which the impedance of the nanostructure dips. In contrast, when each Mg or Zn porphyrin contains the same number of holes, no hopping can occur. The rate of hole hopping will determine the impedance characteristics of each state of each porphyrin nanostructure in the chip, and a decrease in the cell impedance would be expected at the hole-hopping frequency for each state of each porphyrin. While characterization of these hole-hopping states requires the collection of the entire frequency spectrum, the actual read cycle of the DHMU storage medium need only monitor a single frequency at a time. Impedance measurements using lock-in based systems apply only one frequency at a time to the electrode; any other frequencies are nearly totally suppressed by the lock-in amplifier. Thus, it is possible to monitor the frequency characteristic of hole-hopping level of each state and simultaneously determine the logic level of each element in the array using lock-in techniques.

This method of reading is extremely sensitive for molecular memories that utilize relatively small numbers of redox-active units (e.g. porphyrinic macrocycle nanostructures). The examination of the impedance can also be performed without compromising the integrity of a particular memory element.

For all I/O operations with the molecular memories of this invention, the use of molecular electronic components as on-chip buffering and decoding circuitry is desirable although not required. Hybrid systems can easily be produced incorporating the devices of this invention into conventional integrated circuit packages that contain all the circuitry required for encoding/decoding data, reading and writing to the storage element, monitoring fault tolerance and dynamically optimizing/selecting active storage elements to maximize fault tolerance.

C) Instrumentation For Reading/Writing Molecular Memories

As indicated above, the molecular memory devices can be read by any of a wide variety of electrochemical technologies including amperometric methods (e.g. chronoamperometry), coulometric methods (e.g. chronocoulometry), voltammetric methods (e.g., linear sweep voltammetry, cyclic voltammetry, pulse voltammetries, sinusoidal voltammetry, etc.), any of a variety of impedance and/or capacitance measurements, and the like. Such readouts can be performed in the time and/or frequency domain.

1) Fast Potentiostat/Voltammetry System

In one preferred embodiment, readout is accomplished using a fast potentiostat/voltammetry system. Such a system is capable of reading and writing the memory elements, on a microsecond time scale. Such a system can be modified from a prototypical system described in U.S. Pat. No. 5,650,061.

Figure 11:
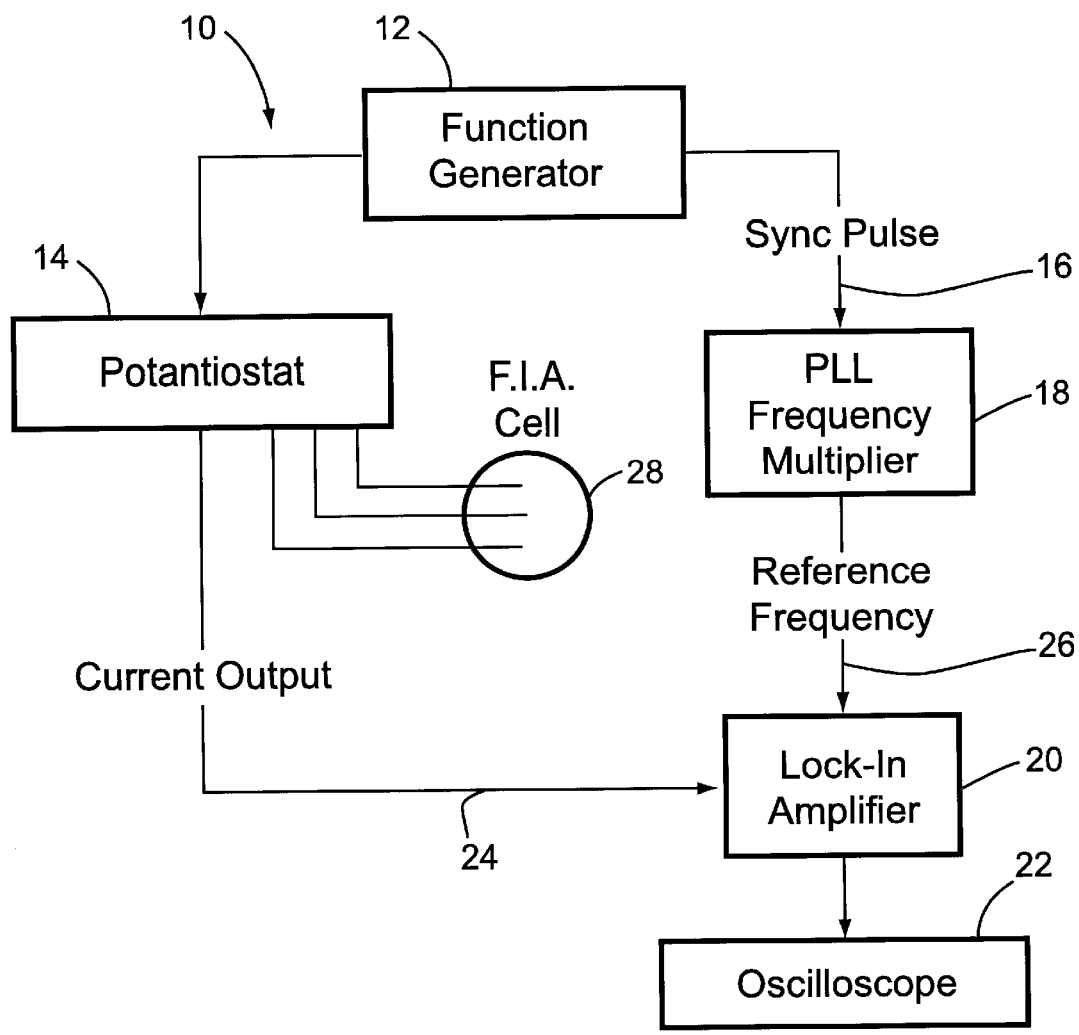
FIG. 11 illustrates a sinusoidal voltammetry system suitable for readout of the memory devices of this invention.

As illustrated in FIG. 11, a potentiostat with an RC time constant less than one microsecond is provided by using a fast voltage driver (e.g., video buffer amplifier). A preferred video buffer amplifier retains a usable bandwidth beyond 20 MHz and is used to rephase the voltage and current in the excitation signal to zero phase shift between voltage and current. This rephasing of the excitation signal immediately before the working electrode cancels out any phase shift which might be introduced by capacitance in the cable leading from the Arbitrary Waveform Synthesizer (AWS) function generator. An important part of the current monitor is a wide band op-amp. By using an op-amp with a very wide gain-bandwidth product, the amplifier gain can be set to 10,000 and still retain a bandwidth usable from DC to above 1 MHz. This allows the collection of impedance data from electrodes as small as a 1 $\mu$m disk over a frequency range from 15 kHz to 5 MHz.

2) A Megahertz Impedance Analysis System

An ultrafast impedance analysis system capable of characterizing the SHMU storage medium on a microsecond time scale can be constructed using an Arbitrary Waveform Synthesizer (e.g., HP 8770A, AWS) and a 1-GHz Digitizing Oscilloscope (e.g., HP 54111D) controlled by a computer system (e.g. HP 9000 series 300 computer system, Hewlett-Packard, Palo Alto, Calif.). The impedance data sets can be collected with the digital scope with 8192 time domain points at 25 MHz. Thus, a full 8192 point data set can be acquired in a total of 328 $\mu$s. Both the excitation and the response waveforms are measured; the excitation waveform is measured prior to the start of the experiment so that the response acquisitions can be done during the course of the experiment without interruption. One preferred excitation signal consists of a waveform with an amplitude of 60 $mV_{(p-p)}$ which covers a frequency band from approximately 30 KHz to over 1 MHz. If five complete replicates of each excitation or response waveform are contained within the 8192 data points set captured by the capture device (e.g. oscilloscope), because no further ensemble averaging is needed, each full impedance spectra can be acquired in 328 $\mu$s. Therefore, the whole frequency band under study can be excited and monitored in a single acquisition. The FFT of the time domain data provides frequency-amplitude and frequency-phase characterization of the data equivalent to the data given by a lock-in based system.

VIII. Use of the Storage Device in Computer Systems

Figure 12:
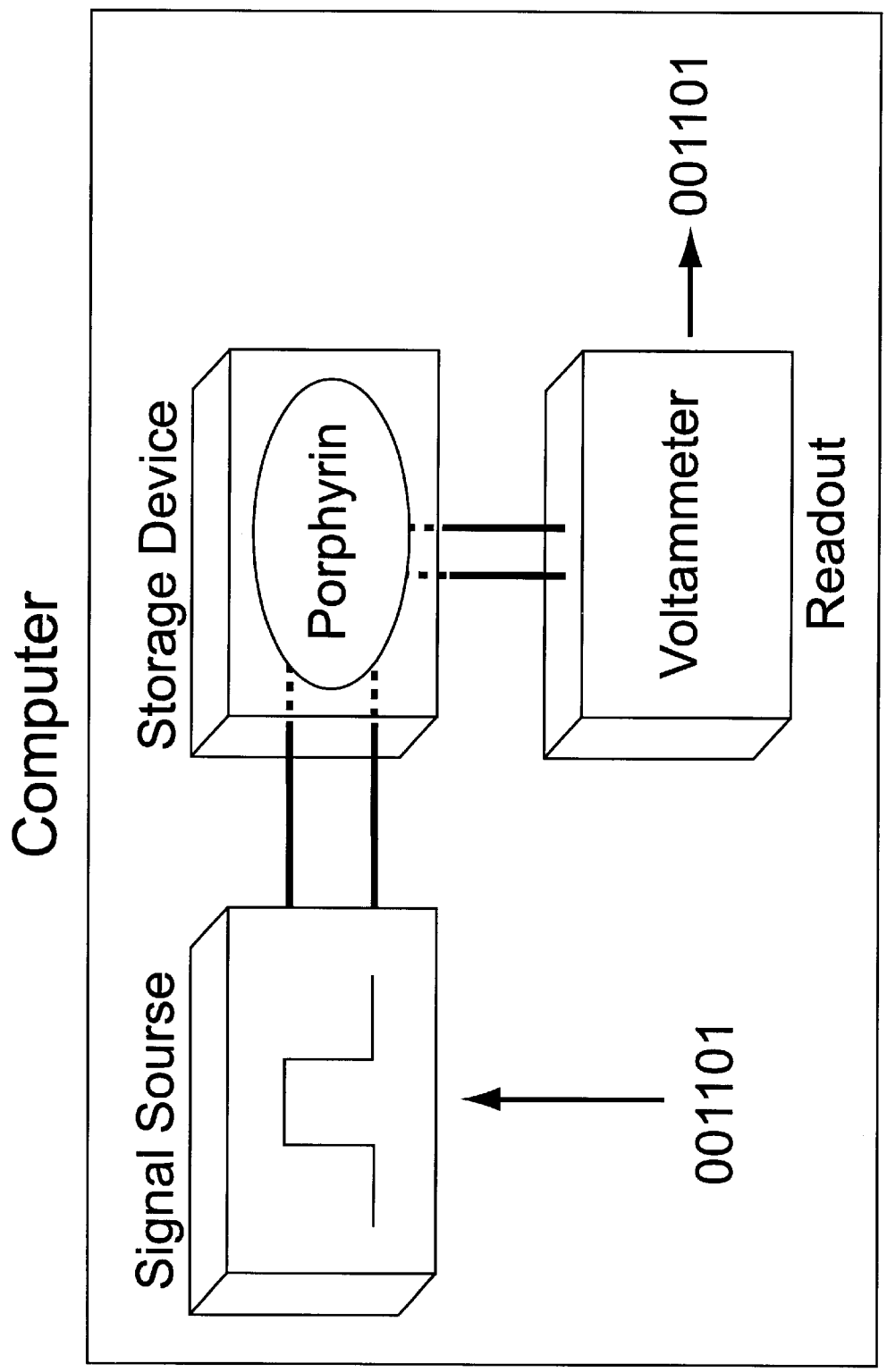
FIG. 12 illustrates a computer system embodying the memory devices described herein. Typically the memory device will be fabricated as a sealed "chip". Ancillary circuitry on the chip and/or in the computer permits writing bits into the memory and retrieving the written information as desired.
Figure 13:
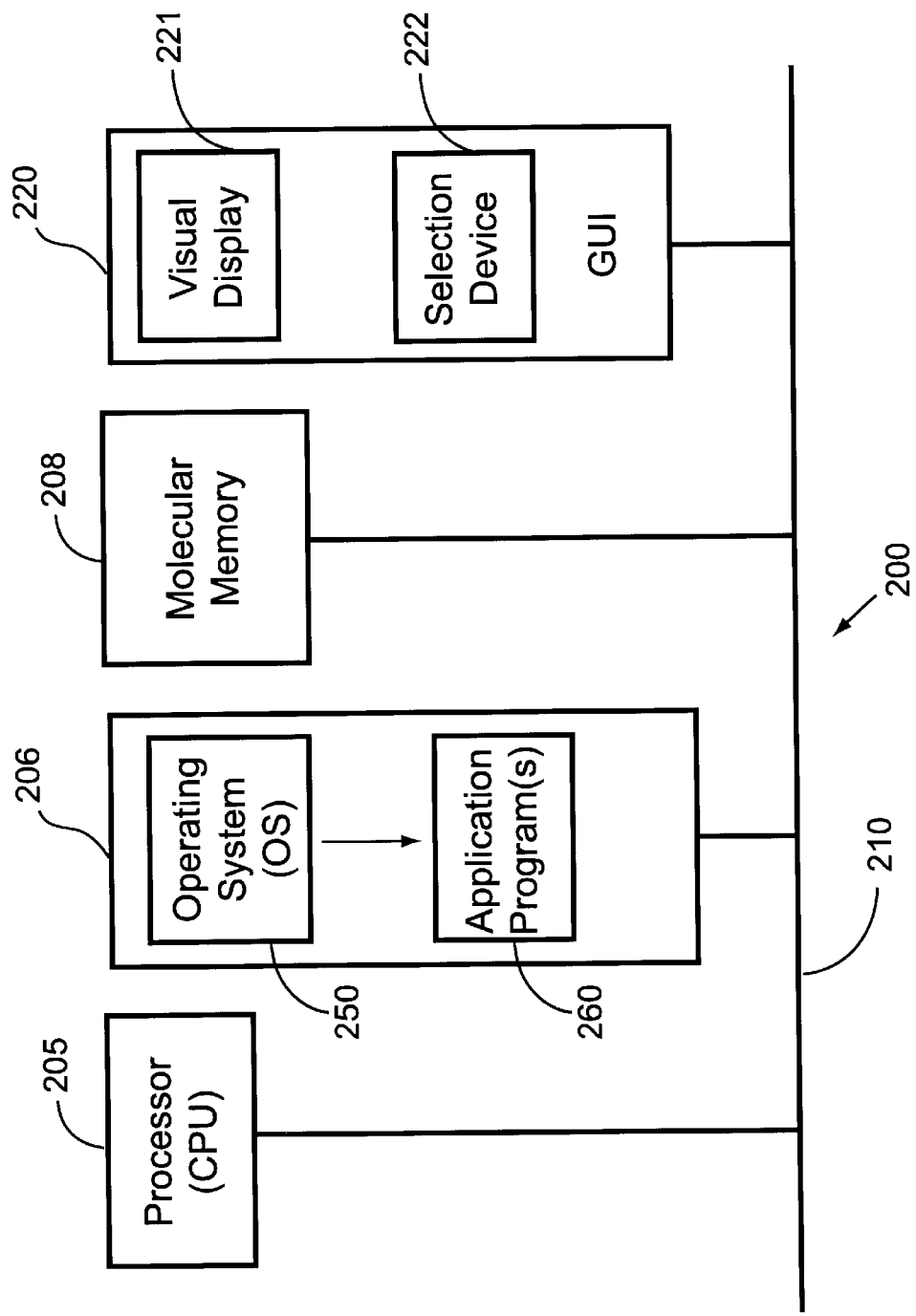
FIG. 13 illustrates the memory devices of this invention integrated into a standard computer architecture or computer system 200.

The use of the storage devices of this invention in computer systems is contemplated. One such computer system is illustrated in FIG. 12. The computer comprises a signal source (e.g. I/O device or CPU) a storage device of this invention and appropriate circuitry (e.g. voltammetry circuitry) to read the state(s) of the storage device. In operation, voltages representing the bits to be stored are applied to the working electrodes of the storage device thereby setting the memory. When retrieval is necessary (e.g. for output, or further processing) the state(s) of the storage device is read by the I/O circuitry and the information is passed off to other elements (e.g. CPU) in the computer.

FIG. 12 illustrates the memory devices of this invention integrated into a standard computer architecture or computer system 200. The hardware of system 200 includes a processor (CPU) 205, a memory 206 (which can comprise molecular memory devices), a persistent storage 208 which does comprise molecular memory devices of this invention, and hardware for a graphical user interface (GUI) 220, coupled by a local bus or interface 210. The persistent memory 208 can include the elements shown in FIG. 11. System 200 can further include additional hardware components (not shown).

System 200 can be, for example, a personal computer or workstation. Processor 205 can be, for example, a microprocessor, such as the 80386, 80486 or Pentium™ microprocessor, made by Intel Corp. (Santa Clara, Calif.). Memory 206 can include, for example, random-access memory (RAM), read-only memory (ROM), virtual memory, molecular memory (FIG. 11) or any other working storage medium or media accessible by processor 205.

Persistent storage 208 can include a hard disk, a floppy disk, an optical or magneto-optical disk, a molecular memory or any other persistent storage medium. GUI 220 facilitates communications between a user and system 200. Its hardware includes a visual display 221 and a selector device (mouse, keyboard, etc.) 222. Through visual display 221, system 200 can deliver graphical and textual output to the user. From selector device 222, system 200 can receive inputs indicating the user's selection of particular windows, menus, and menu items. Visual display 221 can include, for example, a cathode-ray tube (CRT) or flat-panel display screen, or a head-mounted display such as a virtual reality display. Selector device 222 can be, for example, a two-dimensional pointing device such as a mouse, a trackball, a track pad, a stylus, a joystick, or the like. Alternatively or additionally, selector device 222 can include a keyboard, such as an alphanumeric keyboard with function and cursor-control keys.

The software of system 200 includes an operating system 250 and an application program 260. The software of system 200 can further include additional application programs (not shown). Operating system 150 can be, for example, the Microsoft® Windows™ 95 operating system for IBM PC and compatible computers having or emulating Intel 80386, 80486, or Pentium™ processors. Alternatively, the operating system can be specialized for operation utilizing molecular memory elements. Application program 160 is any application compatible with the operating system and system 200 architecture. Persons of skill in the art will appreciate that a wide range of hardware and software configurations can support the system and method of the present invention in various specific embodiments.

EXAMPLES

The following examples are offered to illustrate, but not to limit the claimed invention.

Example 1
Thiol-Porphyrins For Attachment to Electroactive Surfaces as Molecular Memory Devices

I. Molecular Design

This example presents the design and synthesis of porphyrins that can be attached covalently, in defined geometries, to electroactive surfaces. For the present purposes, we consider only the surface of a gold electrode. Three design features we sought to obtain included the following: (1) The ability to attach porphyrins via a sulfide linkage to the gold electrode surface with the porphyrins oriented vertically or horizontally. (2) The ability to tune the porphyrin electrochemical oxidation potential through the use of electron-withdrawing or releasing substituents at the periphery of the porphyrin, or the use of different metals in metalloporphyrins. (3) The use of thiol protecting groups that would cleave spontaneously on the gold surface, thereby avoiding the potential practical problems of handling free thiols.

In order to achieve a vertical orientation of the porphyrin attached to the gold surface, we employed $A_3B$ meso-substituted porphyrins where the B group bears the thiol for surface attachment. The remaining three A groups bear substituents for control of the electrochemical potential. In order to achieve a horizontal orientation of the porphyrin attached to the gold surface, we employed porphyrins possessing two or four $CH_2SH$ groups in the meta position of the meso-phenyl rings. The tuning of the electrochemical potential can be achieved in a straightforward manner in the $A_3B$-porphyrins, where the A group can range from electron-rich substituents such as mesityl to electron-deficient substituents such as the pentafluorophenyl group. With the horizontally-oriented porphyrins, the introduction of substituents to tune the potential must be done without interfering with the meta-$CH_2SH$ groups. Accordingly, we have elected to investigate different metals with the horizontally-positioned porphyrins. The selection of the thiol protecting group poses extensive challenges. The protecting group of choice should be stable under diverse conditions, including the acidic and oxidative conditions of porphyrin formation as well as conditions for porphyrin metalation (generally involving mild Lewis acids, in some cases in the presence of bases). One objective is to be able to construct diarylethyne-linked multiporphyrin arrays, which require Pd-mediated coupling reactions. We sought thiol protecting groups that would meet these diverse criteria.

II. Results
Aldehydes

Figure 14:
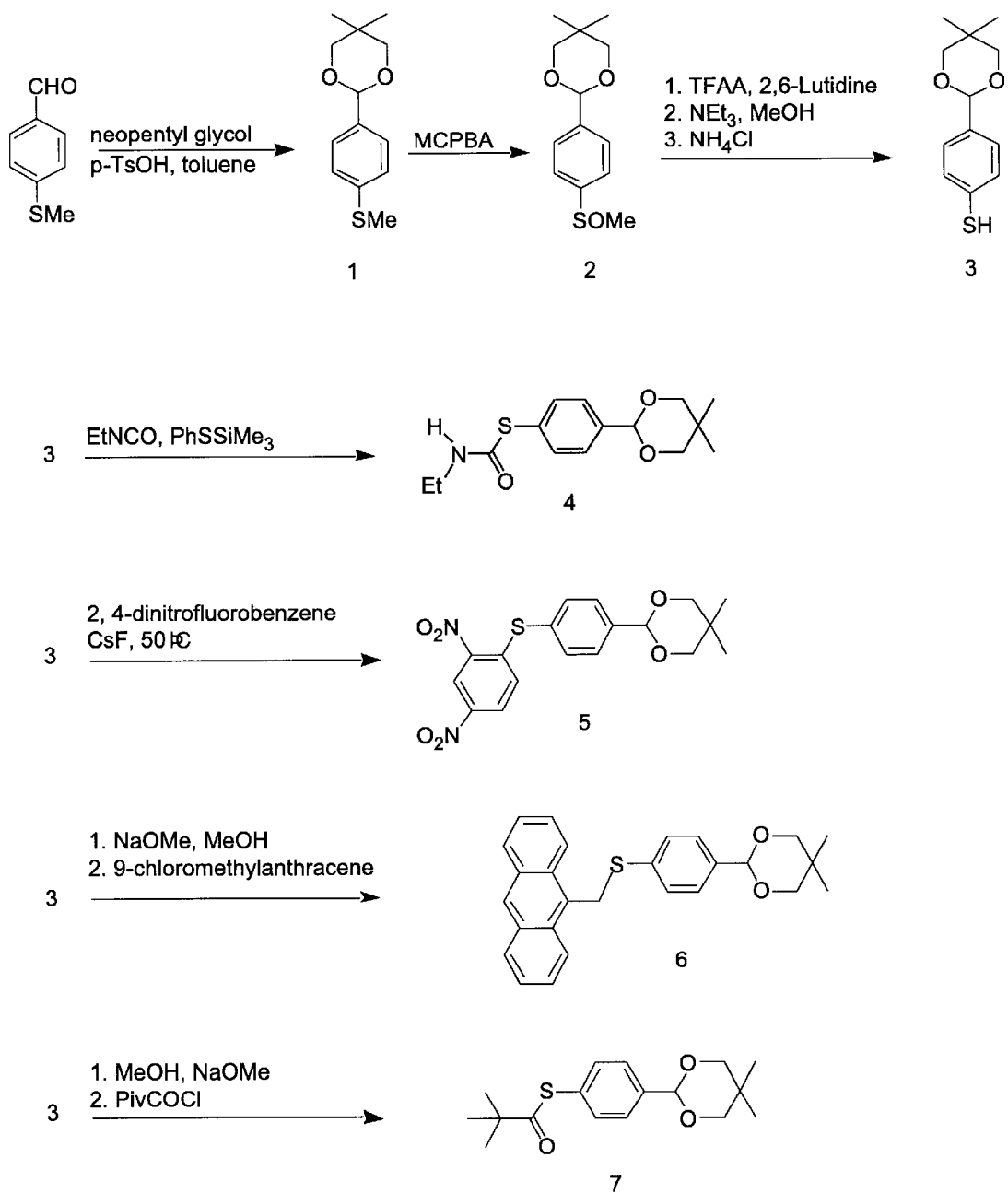
FIG. 14 illustrates synthesis scheme 1 for the synthesis of latent benzaldehydes with various protecting groups for the p-thiol moiety. These are used in the synthesis of thiol-substituted porphyrins.

Our initial synthetic strategy toward mono-thiol ($A_3B$) porphyrins for vertical orientation started from 4-methylthiobenzaldehyde which we hoped to convert to 4-mercaptobenzaldehyde dimethyl acetal (using the strategy of Young et al. (Young et al. (1984) *Tetrahedron Lett.*, 25: 1753–1756)) and next to the thiol-protected dimethyl acetals. The first step involved conversion of the aldehyde group to its dimethyl acetal under standard conditions. The sulfide obtained was successfully converted to the sulfoxide in 95% yield but treatment of the sulfoxide with TFAA led to polymerization rather than the thiol (probably because of cleavage of acetal and intermolecular thioacetalization). We overcame this problem by making two improvements: (1) the dimethyl acetal was replaced by a more bulky acetal protecting group at an earlier stage of the synthesis, (2) milder conditions for the Pummerer rearrangement were employed (Sugihara et al. (1978) *Synthesis*, 881). Thus protection of the carbonyl group with neopentyl glycol (Rondestvedt (1961) *J. Org. Chem.*, 26: 2247–2253) followed by oxidation of the resulting acetal (1) smoothly afforded sulfoxide 2 in 86% overall yield (Scheme 1, FIG. 14). Treatment of sulfoxide 2 with TFAA in the presence of 2,6-lutidine followed by hydrolysis of the resulting intermediate furnished thiol 3. Compound 3 was transformed into the S-protected acetals 4, 5, 6, and 7 using ethyl isocyanoacetate (Ricci et al. (1977) *J. Chem. Soc. Perkin Trans.* 1: 1069–1073), 2,4-dinitrofluorobenzene (Vorozhtsov et al. (1958) *Z. Obs. Chim.*, 28: 40–44, Engl. Transl. 40–44), 9-chloromethylanthracene (Kornblum and Scott (1974) *J. Am. Chem. Soc.*, 96: 590–591), and pivaloyl chloride, respectively, in overall yields of 20–65% from the sulfoxide 2. The acetal group in 4, 5, 6 and 7 was selectively hydrolyzed prior to formation of the corresponding porphyrin.

Figure 15:
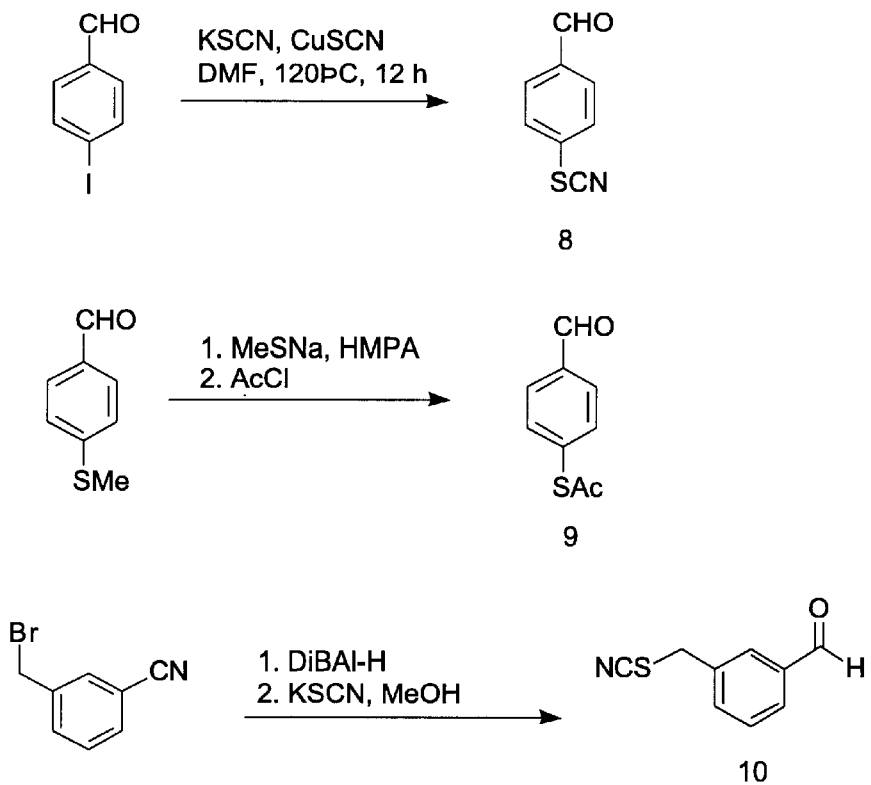
FIG. 15 illustrates synthesis scheme 2 for the synthesis of benzaldehydes with protected thiol groups. These are used in the synthesis of thiol-derivatized porphyrins.

Two other S-protectedp-thiobenzaldehydes were obtained as shown in Scheme 2 (FIG. 15). The thiocyanatobenzaldehyde 8 was prepared according to a general procedure (Suzuki and Abe (1996) *Synth. Commun.*, 26: 3413–3419) in 20% yield. All attempts to improve the yield by replacement of DMF with 1,3-dimethyl-2-imidazolidinone, increasing the temperature, or prolonging the reaction time were unsuccessful. S-cetylthiobenzaldehyde 9 was prepared in a two-step one-flask procedure. Cleavage of the ethyl group of 4-methylthiobenzaldehyde according to a general procedure (Tiecco et al. (1982) *Synthesis*, 478–480) followed by trapping of the resulting anion with acetyl chloride afforded the desired S-acetylthiobenzaldehyde 9 in 55% yield.

Our approach toward horizontally-oriented porphyrins required access to S-protected m-(HSCH$_2$)benzaldehydes. The commercially available m-(bromomethyl)benzonitrile was reduced with DiBAI-H to the corresponding m-(bromomethyl)benzaldehyde (Wagner et al. (1997) *Tetrahedron*, 53: 6755–6790) (Scheme 2, FIG. 15). Substitution of the bromine with potassium thiocyanate gave the thiocyanatobenzaldehyde 10 as colorless crystals in 74% yield. By using the thiocyanate as protecting group, incorporation and protection of the sulfur unit could be achieved in one step.

Porphyrins

Figure 16:
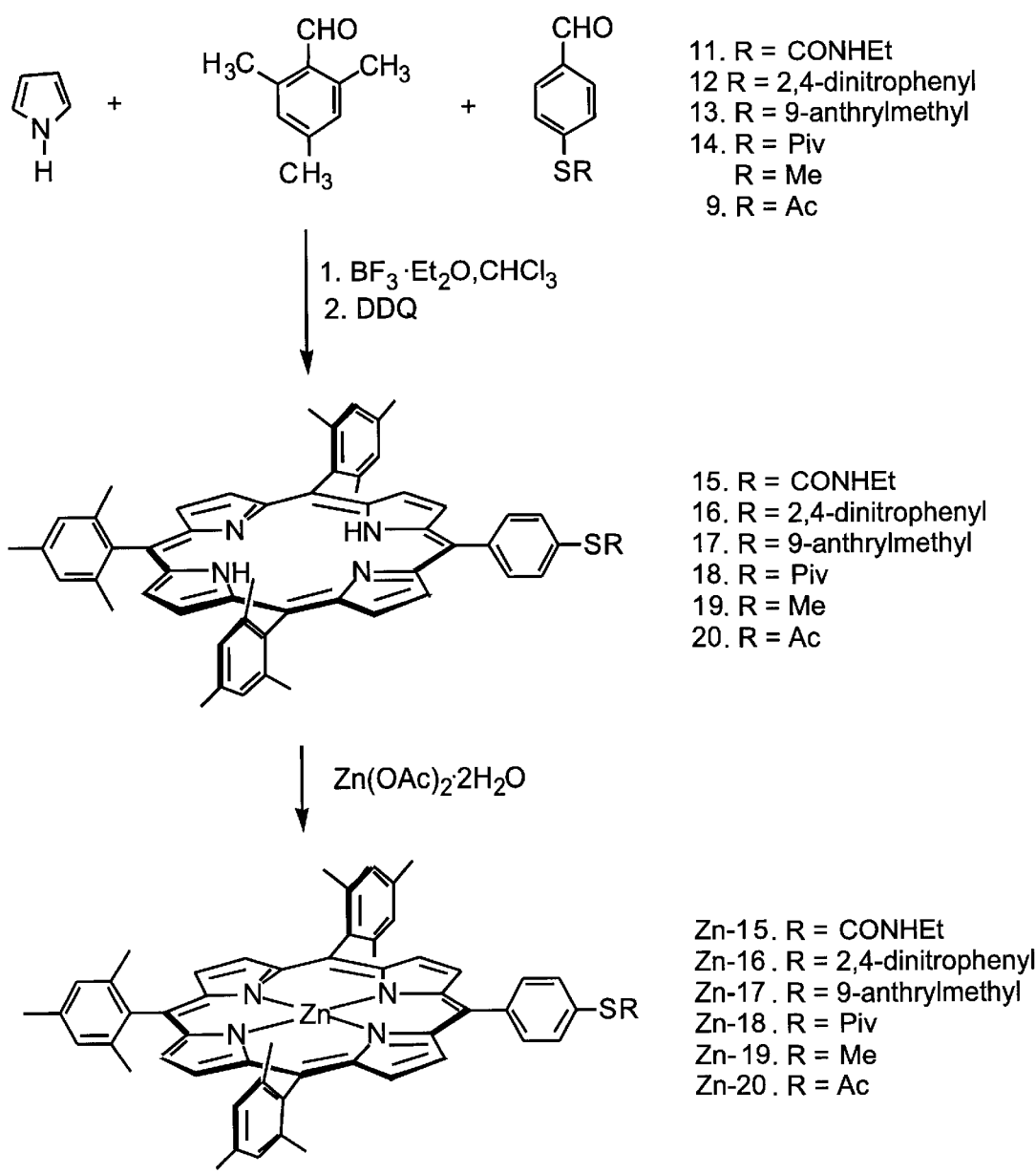
FIG. 16 illustrates synthesis scheme 3 for the synthesis of metallo-free and zinc porphyrins each bearing three mesityl groups and one protected p-thiophenyl group.

The A$_3$B-porphyrins were prepared using a two-step, one-flask room temperature synthesis of meso-substituted porphyrins that is compatible with a variety of precursor aldehydes including the ortho-disubstituted benzaldehydes that yield facially-encumbered porphyrins (Lindsey and Wagner (1989) *J. Org. Chem.*, 54: 828–836, Lindsey, J. S. in *Metalloporphyrins-Catalyzed Oxidations;* Montanari, F., Casella, L., Eds.; Kluwer Academic Publishers: The Netherlands, 1994; pp 49–86, Lindsey et al. (1994) *J. Org. Chem.*, 59: 579–587). A mixed-aldehyde condensation of mesitaldehyde, a thiol-protected aldehyde, and pyrrole afforded a mixture of porphyrins, from which the desired thiol-protected A$_3$B-porphyrin was obtained by chromatography. The acetals 4–7 were hydrolyzed with trifluoroacetic acid and the resulting aldehydes 11–14 were used directly without purification in the respective porphyrin syntheses. Thus, aldehydes 9, 11, 12, 13 or 14 as well as commercially available 4-methylthiobenzaldehyde afforded thiol-protected A3B-porphyrins 20, 15, 16, 17, 18 or 19, respectively, in ~10% yield (Scheme 3, FIG. 16). The porphyrins obtained were metalated using Zn(OAc)$_2$.2H$_2$O, affording Zn-20, Zn-15, Zn-16, Zn-17, Zn-18 or Zn-19.

Figure 17:
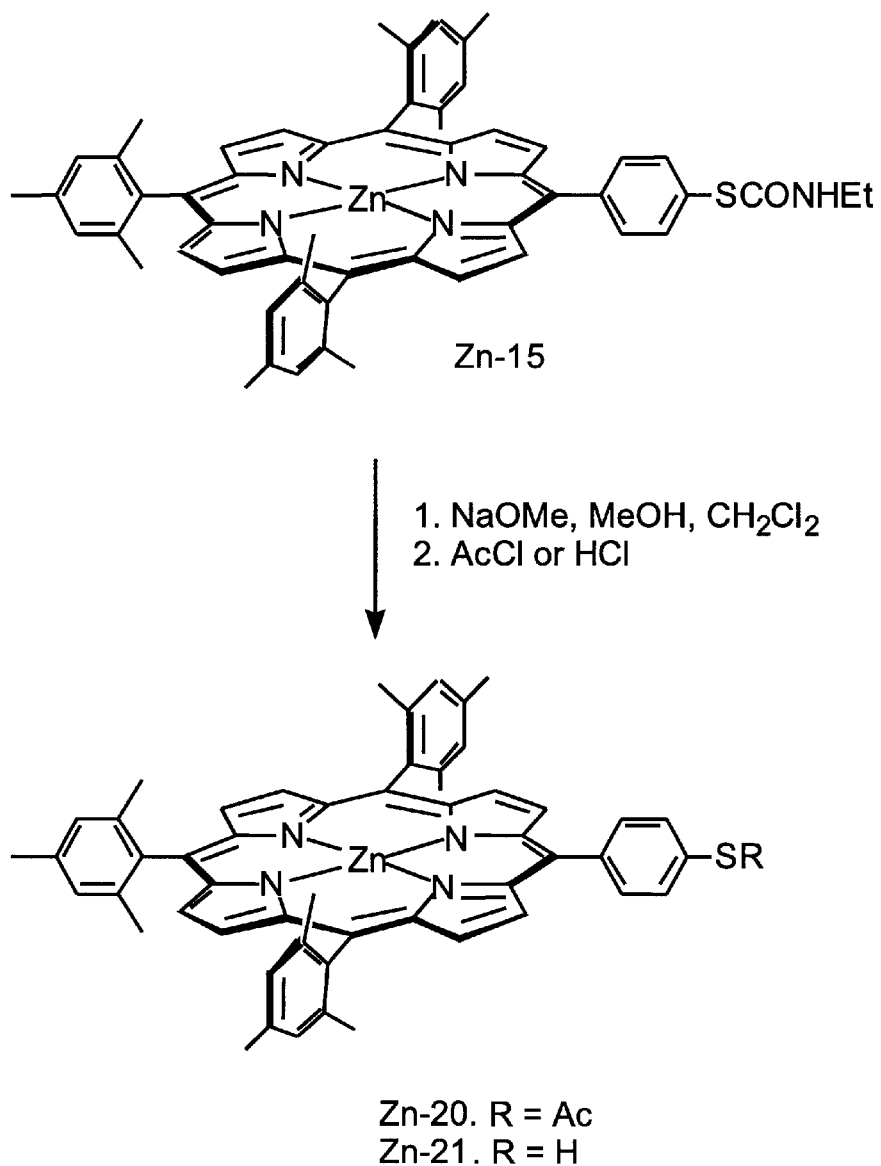
FIG. 17 illustrates synthesis scheme 4 for the synthesis of a zinc porphyrin bearing three mesityl groups and one free thiol group.

Examination of the behavior of various thiol-protected zinc porphyrins revealed that the S-(N-ethylcarbamoyl) and S-acetyl groups easily cleaved in situ and the resulting porphyrin product bound on the gold surface (vide infra). We decided to confirm this result by also cleaving the S-(N-ethylcarbamoyl) group in porphyrin Zn-15 using basic conditions. Treatment of porphyrin Zn-15 with sodium methoxide followed by acidic workup gave mono-thiol porphyrin Zn-21, which was air-sensitive and proved very difficult to purify to homogeneity (the porphyrin disulfide was also present) (Scheme 4, FIG. 17). The same reaction performed with quenching by acetyl chloride afforded the S-acetyl porphyrin Zn-20. Both Zn-15 and Zn-20 were found to bind to the gold surface identically with that of the free thiol containing porphyrin Zn-21.

Figure 18:
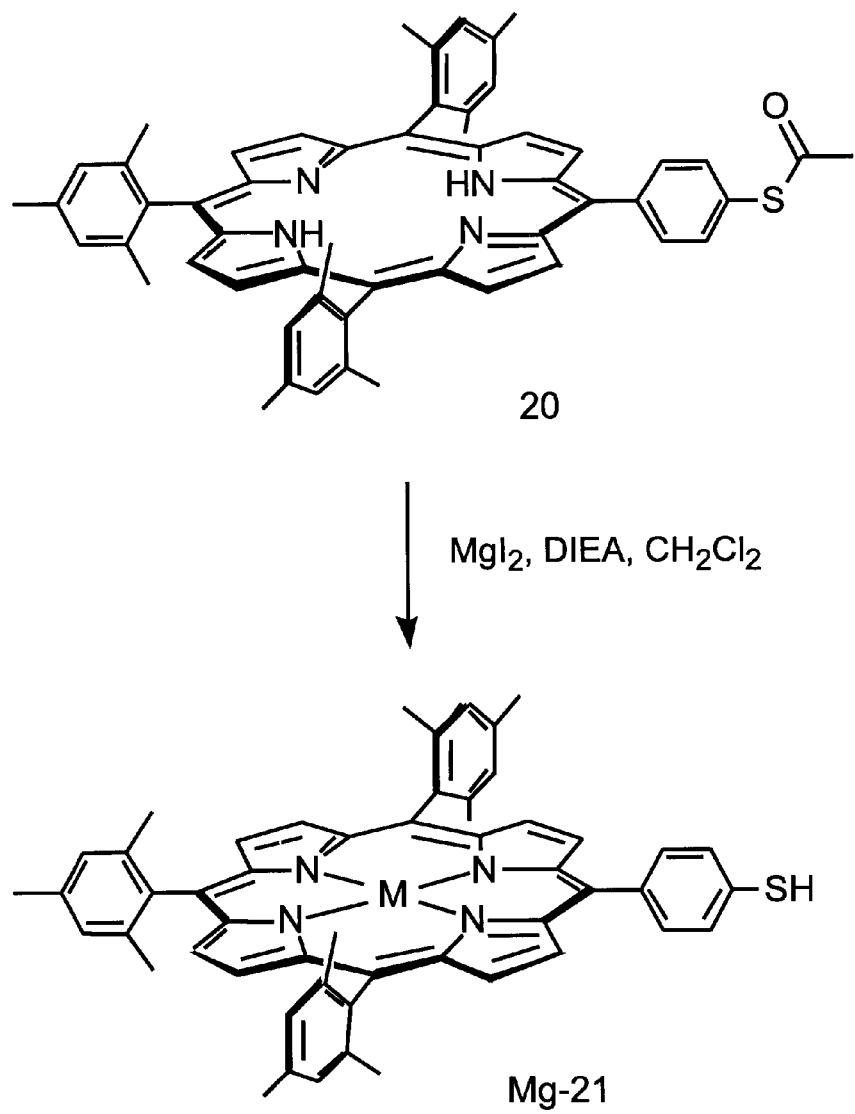
FIG. 18 illustrates synthesis scheme 5 for the synthesis of a magnesium porphyrin bearing three mesityl groups and one p-mercaptophenyl group.

We attempted to insert magnesium into porphyrins 15 and 16 using MgI$_2$ and N,N-diisopropylethylamine in CH$_2$Cl$_2$ (Lindsey and Woodford (1995) *Inorg. Chem.* 34: 1063–1069). In both cases we obtained complex mixtures of porphyrins due to cleavage of the protecting groups. The resulting salts likely contain the thiolate anion complexed with the protonated diisopropylethylamine. All attempts at acidification caused demetalation of magnesium. Magnesium insertion occurred with 5,10,15-trimesityl-20-(4-thiocyanatophenyl)porphyrin under these conditions but the Mg-chelate could not be purified to homogeneity. The difficulty in purification may stem from lability of the thiocyanate group on alumina, as we observed that the thiocyanate group of 5,10,15-trimesityl-20-(4-thiocyanatophenyl)porphyrin is cleaved during chromatography on alumina. Finally we subjected the S-acetyl-derivatized porphyrin 20 to the same magnesium insertion conditions. Magnesium insertion occurred but with cleavage of the thiol protecting group, affording the free thiol Mg-21 in 32% yield (Scheme 5, FIG. 18).

Figure 19:
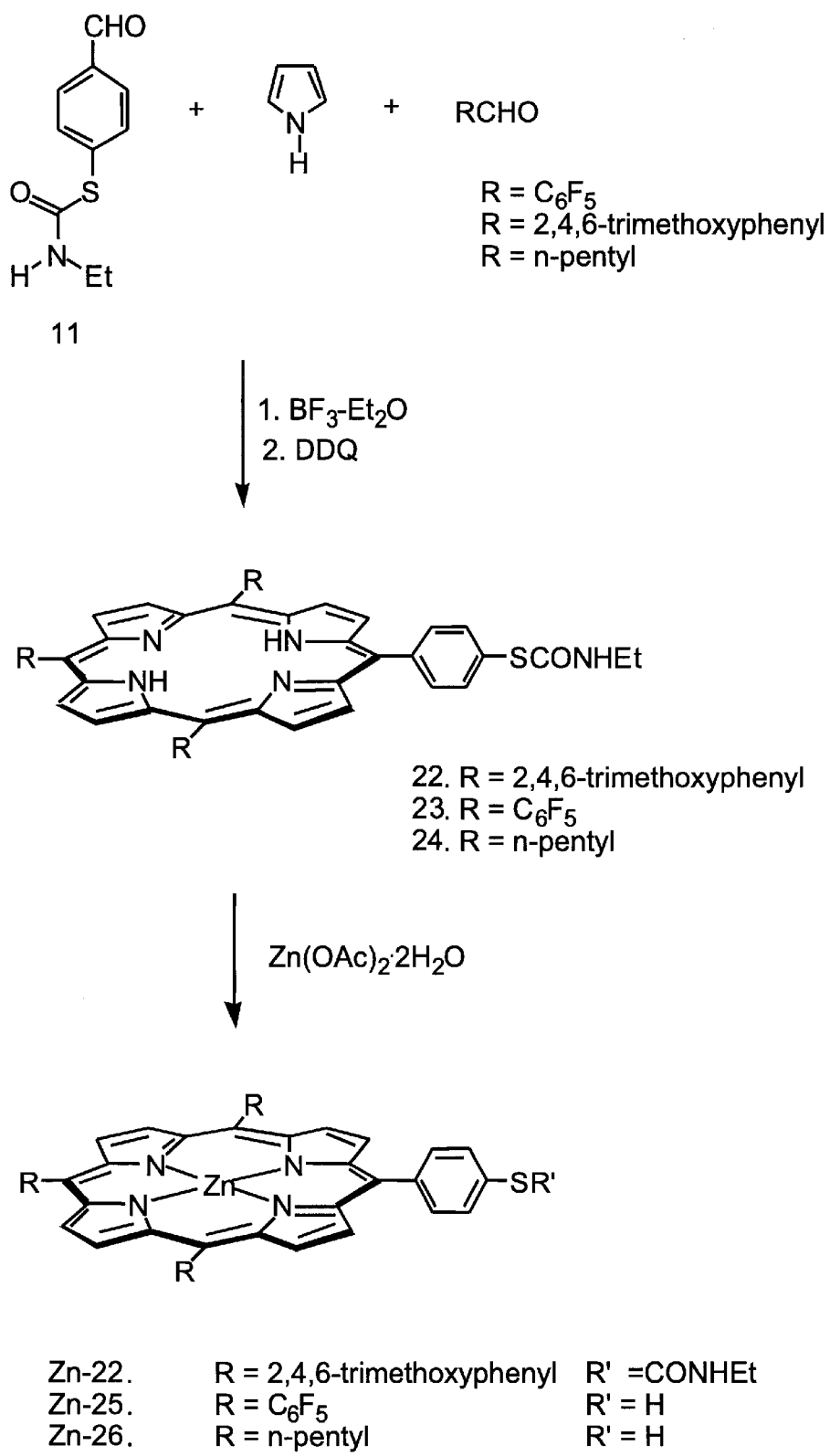
FIG. 19 illustrates synthesis scheme 6 for the synthesis of metallo-free and zinc porphyrins each bearing three groups to tune the oxidation potential and one free or protected p-thiophenyl group.

The results of the gold-binding studies (vide infra) prompted us to use the S-carbamoyl benzaldehyde 11 in subsequent syntheses. Thus mixed aldehyde-pyrrole condensations of aldehyde 11 with 2,4,6-trimethoxybenzaldehyde, pentafluorobenzaldehyde, or n-hexanal yielded porphyrins 22, 23 or 24, respectively (Scheme 6, FIG. 19). Attempted conversion to the zinc chelate gave the thiol-protected porphyrin Zn-22, however the more forcing conditions required for metalation of the tris(pentafluorophenyl)porphyrin and tri-n-pentyl-substituted porphyrin resulted in cleavage of the S-(N-ethylcarbamoyl) group, giving Zn-25 and Zn-26.

The design of porphyrins oriented in a horizontal manner can be achieved by the synthesis of porphyrins bearing a meta-(mercaptomethyl)phenyl group at each of the four meso-positions. We attempted to repeat the synthesis of the unprotected 5,10,15,20-tetrakis[m-(mercaptomethyl) phenyl]porphyrin (Wen et al. (1997) *J. Am. Chem. Soc.*, 119: 7726–7733), but encountered solubility problems due to disulfide formation. Because of the promising results with other thiol protecting groups cleaved directly on the gold surface we decided to synthesize the corresponding thiol-protected porphyrin. As a protected sulfide entity we chose the thiocyanate group due to its high chemical stability.

Figure 20:
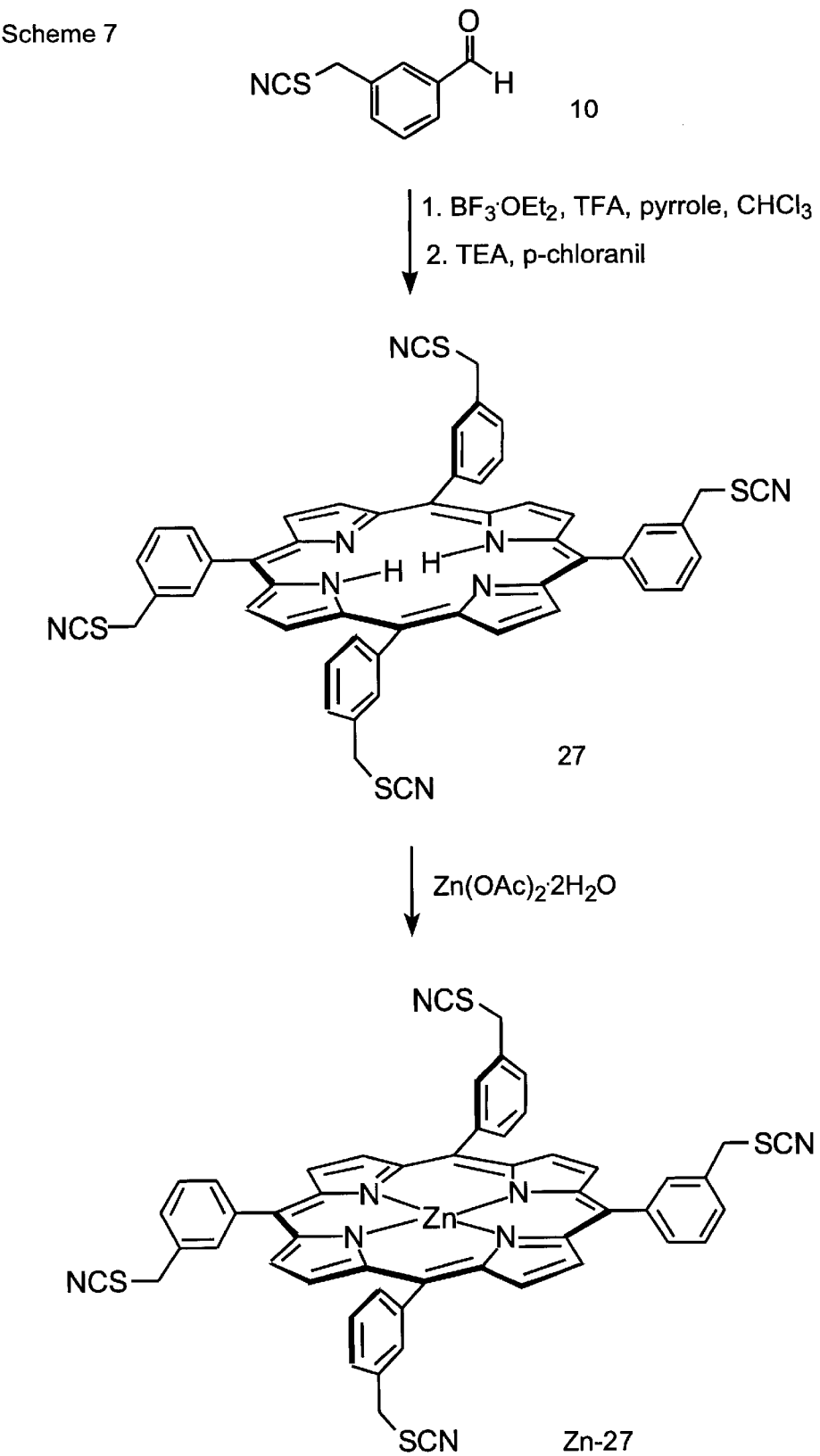
FIG. 20 illustrates synthesis scheme 7 for the synthesis of metallo-free and zinc porphyrins bearing four m-(thiocyanatomethyl)phenyl groups for horizontal orientation on a gold surface.

Condensation of 10 with pyrrole at room temperature afforded the desired 5,10,15,20-tetrakis[m-(thiocyanatomethyl)phenyl]porphyrin 27 as a dark purple solid. Metalation with zinc acetate afforded the zinc-chelate Zn-27 as a purple solid in 79% yield (Scheme 7, FIG. 20). The thiocyanates were easily cleaved on the gold surface, affording a self-assembled porphyrin oriented parallel to the gold surface using all four thiol groups for binding (vide infra).

Figure 21:
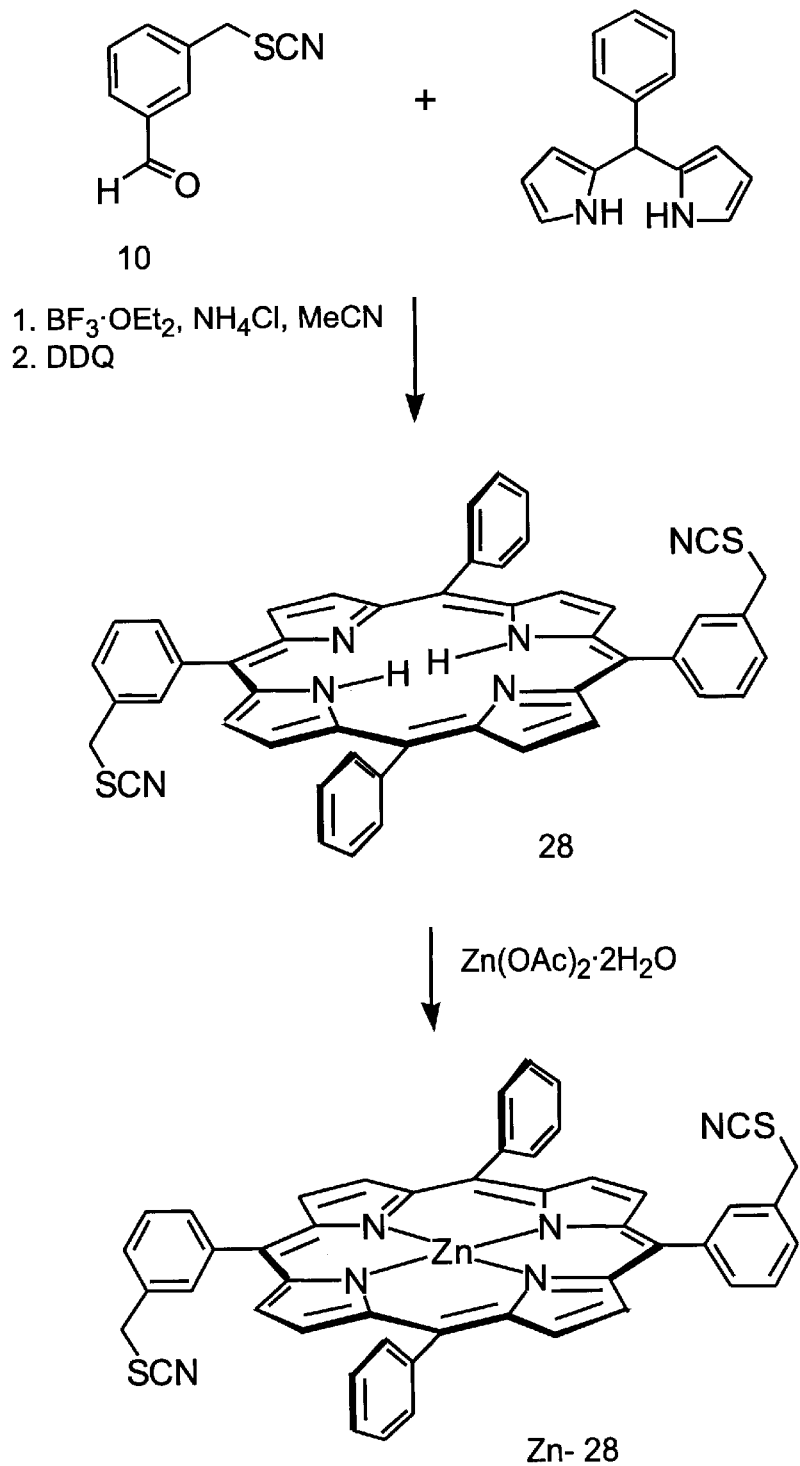
FIG. 21 illustrates synthesis scheme 8 for the synthesis of metallo-free and zinc porphyrins bearing two m-(thiocyanatomethyl)phenyl groups for horizontal orientation on a gold surface.

Driven by these positive results we decided to synthesize a porphyrin with only two 'legs' for attachment to the gold surface. Condensation of aldehyde 10 with 5-phenyldipyrromethane (Lee and Lindsey (1994) *Tetrahedron*, 50: 11427–11440, Littler et al. (1999) *J. Org. Chem.*, 64: 1391–1396) using BF$_3$.OEt$_2$ in acetonitrile to minimize scrambling (Littler et al. (1999) *J. Org. Chem.*, 64: 2864–2872) gave the desired trans-porphyrin 28 in 7% yield (accompanied by 10,15,20-triphenyl-5-[m-(thiocyanatomethyl)phenyl]porphyrin in 2% yield due to scrambling) (Scheme 8, FIG. 21). Metalation of 28 with zinc acetate afforded the zinc porphyrin Zn-28 as a purple solid in 59% yield. Porphyrin Zn-28 also bound to the gold surface by in situ cleavage of the thiocyanate units.

Figure 22:
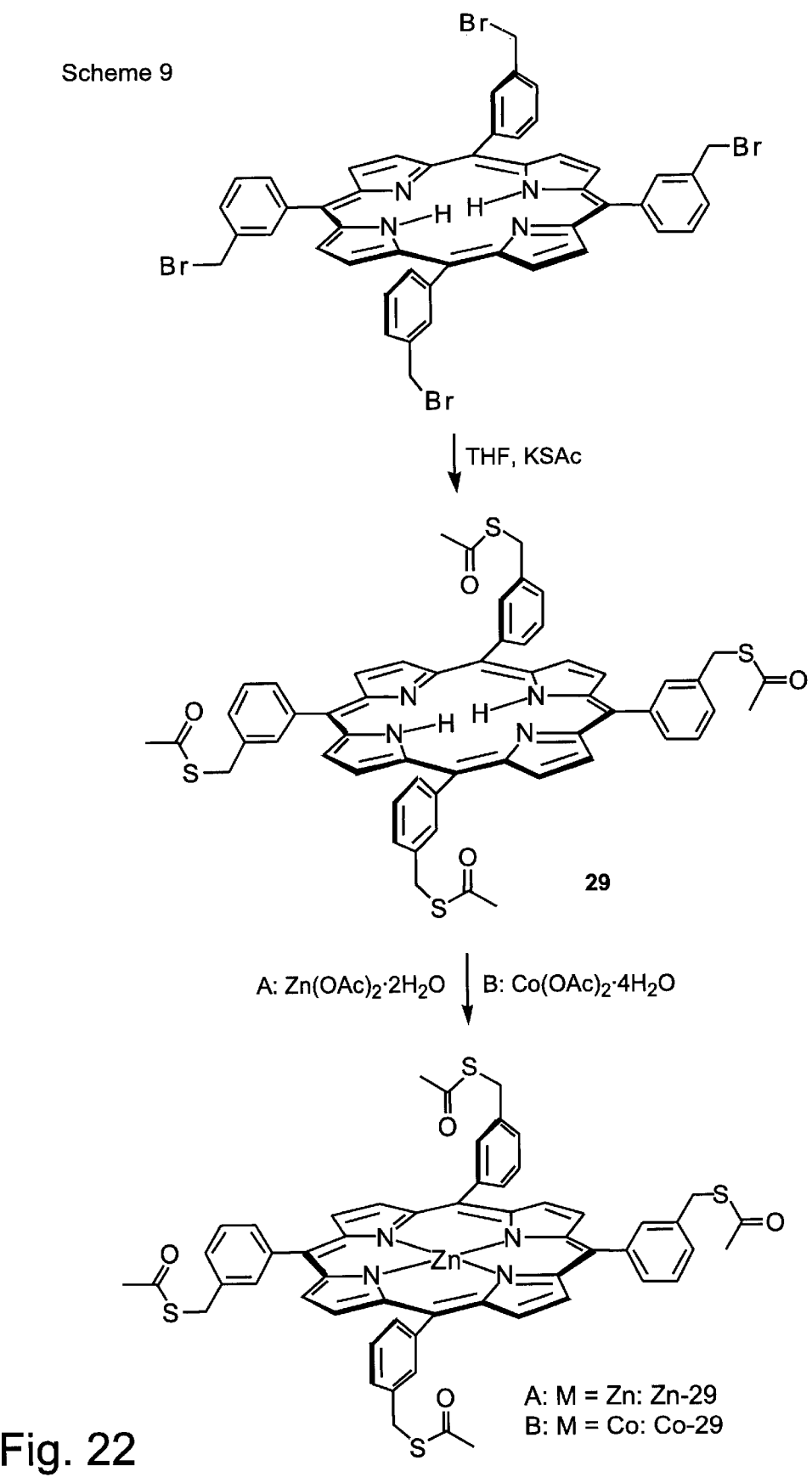
FIG. 22 illustrates synthesis scheme 9 for the synthesis of metallo-free and zinc porphyrins bearing four m-(S-acetylthiomethyl)phenyl groups for horizontal orientation on a gold surface.

To achieve horizontally-oriented porphyrins with different potentials we decided to metalate 5,10,15,20-tetrakis[m-(S-acetylthiomethyl)phenyl]porphyrin (29) with various metal acetates (Scheme 9, FIG. 22). 29 was synthesized by substitution of all four bromides in 5,10,15,20-tetrakis[m-(bromomethyl)phenyl]porphyrin (Wen et al. (1997) *J. Am. Chem. Soc.*, 119: 7726–7733, Karaman et al. (1992) *J. Am. Chem. Soc.*, 114: 4889–4898) with potassium thioacetate in 63% yield. Metalation of free base porphyrin 29 with zinc acetate gave the desired zinc porphyrin Zn-29 in quantitative yield as a purple solid. Using Co(OAc)$_2$.4H$_2$O afforded the corresponding cobalt chelate Co-29 as an orange-purple solid in quantitative yield.

Characterization

The synthetic porphyrins are purple solids with a metallic reflection. The porphyrins are stable to air but slowly decompose in solution in the presence of light. The purity of all porphyrin compounds was routinely checked by TLC, $^1$H NMR spectroscopy (with the exception of the paramagnetic Co-29), LD-MS and UV/VIS spectroscopy. Fluorescence emission and excitation spectroscopy was used to confirm the completeness of the different metalation procedures. FAB-MS and IR spectra were measured to support the structure of the porphyrins.

Generally the LD-MS spectrum of a porphyrin shows the cationic molecule ion peak M$^+$ in high intensity with only little fragmentation (Srinivasan et al. (1999) *J. Porphyrins Phthalocyanines*, 3: 283–291). But some porphyrins with delicate peripheral groups undergo characteristic and extensive fragmentation upon LD-MS analysis. Porphyrins with thiocyanate substituents show the loss of the cyano and the thiocyanato groups, with the latter exhibiting more intense peaks. If more than one thiocyanate group is present, fragmentation can occur for each of these groups. Porphyrins with S-acetyl groups show loss of both the acetyl (—COCH$_3$) and the thioacetate (—SCOCH$_3$) groups. Such fragmentation can generally occur for each thioacetate substituent. A further LD-MS feature observed with thioacetate-derivatized porphyrins involves the appearance of an (M+15)$^+$ peak. Because this peak occurred in the LD-MS spectra of all porphyrins with thioacetate substituents, which were synthesized via different routes, and no other types of spectra show any evidence for the presence of another species, this cannot be an impurity but must be a photochemical artifact involving the transfer of a methyl group. In each case the (M +15)$^+$ peak exhibited the same pattern of fragmentation as observed for the parent molecule ion (M)$^+$. The intensity of the (M+15)$^+$ peak is about 10% of that of the M$^+$ peak.

Behavior on Gold

We surveyed the behavior of the thiol-protected zinc chelates Zn-15, Zn-16, Zn-17, Zn-18, Zn-19 and Zn-20 on gold electrodes. The members of this set of zinc porphyrins each bears three mesityl groups and differ only in the nature of the thiol protecting group. These studies revealed that the S-(N-ethylcarbamoyl) (Zn-15) and S-acetyl (Zn-20) groups were easily cleaved on the gold surface, whereas the S-(2, 4-dinitrophenyl) (Zn-16), S-(9-anthrylmethyl) (Zn-17), S-pivaloyl (Zn-18) and S-methyl (Zn-19) protecting groups were not cleaved. When no cleavage occurred, the thiol-protected porphyrins were not bound to the gold surface. We found that Zn-15 (S-(N-ethylcarbamoyl) protected), Zn-20 (S-acetyl protected), and Zn-21 (free thiol) bind to the gold surface identically. We also examined thiocyanatomethyl-derivatized porphyrins (Zn-27, Zn-28) on gold electrodes. We found that the thiocyanato protecting group cleaves in situ and the corresponding thiol- derivatized porphyrin binds on the gold surface. These results are in accord with and extend a previous report (Tour et al. (1995) *J. Am. Chem. Soc.* 117: 9529–9534) that the S-acetyl group of various thiol-substituted arenes (not porphyrins) is cleaved on the gold surface. Of the three thiol protecting groups that we identified to undergo cleavage in situ on gold electrodes, we also found in survey experiments that only the S-acetyl group is compatible with Pd-coupling reactions for the preparation of diarylethyne-linked multiporphyrin arrays.

Porphyrins Zn-15, Zn-20, Zn-21, Zn-22, Zn-25, Zn-26, Zn-27, Zn-28, and Mg-21 have been attached to a gold electrode. Porphyrins Zn-15, Zn-20, Zn-21, Zn-22, Zn-25, Zn-26, and Mg-21 bear one thiol or protected thiol and bind to the gold surface in a vertical orientation. Porphyrins Zn-27 and Zn-28 bind to the surface in a horizontal orientation with four and two sites of attachment, respectively.

The set of zinc porphyrins with three mesityl (Zn-15, Zn-20, Zn-21), n-pentyl (Zn-26), 2,4,6-trimethoxyphenyl (Zn-22), or pentafluorophenyl (Zn-25) groups, as well as the magnesium porphyrin with three mesityl groups (Mg-21), demonstrate the storage of data (upon oxidation) at different electrochemical potentials.

III. Experimental

General

All chemicals were obtained commercially and used as received unless otherwise noted. Reagent grade solvents (CH$_2$Cl$_2$, CHCl$_3$, hexanes) and HPLC grade solvents (acetonitrile, toluene) were used as received from Fisher. Pyrrole was distilled from CaH$_2$. $^1$H NMR spectra (300 MHz, General Electric GN 30 ONB), absorption spectra (HP 8453, Cary 3), and emission spectra (Spex FluoroMax) were collected routinely. All reported NMR results were obtained at 300 MHz in CDCl$_3$. UV-Vis absorption spectra were recorded in CH$_2$Cl$_2$ or toluene. Flash chromatography was performed on flash silica (Baker, 200–400 mesh) or alumina (Fisher, 80–200 mesh). Mass spectra were obtained via laser desorption (LD-MS) in the absence of an added matrix (Fenyo et al. (1997) *J. Porphyrins Phthalocyanines*, 1: 93–99) using a Bruker Proflex II mass spectrometer, fast atom bombardment (FAB-MS) using a JEOL HX 110HF mass spectrometer (ion source 40 ° C., CsKI or polyethylene glycol standards, 10 ppm elemental compositional accuracy for the porphyrins), or electron-impact mass spectrometry (EI-MS).

2-[(4-Methylthio)phenyl]-5,5-dimethyl-1,3-dioxane (1)

Samples of 4-methylthiobenzaldehyde (20.0 mL, 150 mmol), neopentyl glycol (16.0 g, 155 mmol), toluene (250 mL) and p-toluenesulfonic acid (190 mg, 1.00 mmol) were placed in a 500 mL flask fitted with a Dean-Stark trap and a reflux condenser. The mixture was refluxed cautiously until a sudden exotherm ceased, then for an additional hour (total ~1.5 h). The cooled mixture was washed with sodium bicarbonate solution and with water. After drying with Na$_2$SO$_4$ and evaporation, white crystals crystallized from hexanes (32.2 g, 89.4%). mp 74–75° C.; $^1$H NMR (CDCl$_3$) δ0.83 (s, 3H, CH$_3$C), 1.33 (s, 3H, CH$_3$C), 2.50 (s, 3H, CH$_3$S), 3.67 (AB/2, 2H, CH$_2$O, J=10.2 Hz), 3.79 (AB/2, 2H, Ch$_2$O, J=10.2 Hz), 5.25 (s, 1H, acetal), 7.30, (AA'BB', 4H, ArH); $^{13}$C NMR (CDCl$_3$) δ16.5, 22.6, 23.8, 30.9, 78.3, 102.1, 127.1, 127.4, 136.2, 140.0; EI-MS m/z 238.1028 (M)$^+$ (C$_{13}$H$_{18}$O$_2$S requires 238.1028); Anal. Calcd. for C$_{13}$H$_{18}$O$_2$S: C, 65.51; H, 7.61; S, 13.45; Found: C, 65.62; H, 7.70; S, 13.55.

2-[(4-Methylsulfoxy)phenyl]-5,5-dimethyl-1,3-dioxane (2)

A solution of acetal 1 (19 g, 80 mmol) in CH$_2$Cl$_2$ (150 mL) was cooled to −20° C. and stirred vigorously. Then a solution of MCPBA (31 g of 50–55% water suspension, 90 mmol) in CH$_2$Cl$_2$ (100 mL) was added dropwise over 1 h. The mixture was stirred at 0° C. for an additional 1 h. Then Ca(OH)$_2$ (11 g, 0.15 mmol) and Na$_2$SO$_4$ (20 g) were added and stirring was continued for 1 h. After filtration and evaporation, the warm colorless oil was dissolved in CH$_2$Cl$_2$ (20 mL) and hexanes was added, affording white crystals that were isolated by filtration (14.6 g). The filtrate was evaporated and the residual oil was recrystallized, affording a second crop of white crystals. The total yield was 19.6 g (97%). mp 116–117° C.; $^1$H NMR (CDCl$_3$) δ0.77 (s, 3H, CH$_3$C), 1.24 (s, 3H, CH$_3$C), 2.65 (s, 3H, CH$_3$SO), 3.62 (AB/2, 2H, CH$_2$O, J=11.1 Hz), 3.74 (AB/2, 2H, CH$_2$O, J=10.8 Hz), 5.40 (s, 1H, acetal), 7.6–7.7 (m, 4H, ArH); $^{13}$C NMR (CDCl$_3$) δ22.5, 23.7, 30.9, 44.7, 78.3, 101.3, 124.0, 128.0, 142.2, 146.7; EI-MS obsd 254.0975, calcd exact mass 254.0977 (C$_{13}$H$_{18}$O$_3$S); Anal. Calcd. for C$_{13}$H$_{18}$O$_3$S: C, 61.39; H, 7.13; S, 12.61; Found: C, 61.29; H, 7.03; S, 12.70.

2-(4-Mercaptophenyl)-5,5-dimethyl-1,3-dioxane (3)

Sulfoxide 2 (7.62 g, 30.0 mmol) was dissolved in $CH_3CN$ (120 mL). 2,6-Lutidine (10.8 mL, 93.0 mmol) was added and the mixture was cooled to −20° C. To the resulting suspension TFAA (12.7 mL, 90.0 mmol) was added dropwise maintaining the temperature below 0° C. The sulfoxide disappeared and the mixture turned a lemon yellow. When the addition was complete, the mixture was stirred at ~0° C. for 1 h. The mixture was then allowed to warm to room temperature. All volatile materials were evaporated at 30° C. Next a precooled mixture of $NEt_3$ (50 mL) and MeOH (50 mL) was added. After 30 min at room temperature all volatile materials were evaporated under reduced pressure at low temperature. The residual yellow oil was dissolved in ether (70 mL) and extracted with sat. $NH_4Cl$ (250 mL). The layers were separated, the organic layer was dried ($Na_2SO_4$) and concentrated to dryness giving a yellow-orange oil (6.61 g, 98% yield of crude material) of which ~70% was the desired compound. The crude thiol was pure enough for the next step. A small sample was oxidized to the respective disulfide and characterized. mp 134–136° C.; $^1H$ NMR ($CDCl_3$) δ0.80 (s, 3H, $CH_3C$), 1.28 (s, 3H, $CH_3C$), 3.63 (AB/2, 2H, $CH_2O$, J=10.2 Hz), 3.76 (AB/2, 2H, $CH_2O$, J=11.2 Hz), 5.36 (s, 1H, acetal), 7.43, 7.49 (AA'BB', ArH); $^{13}C$ NMR ($CDCl_3$) δ16.5, 22.6, 23.7, 30.9, 78.3, 101.8, 127.6, 128.1, 138.2, 138.4; FAB-MS obsd 446.1574, calcd exact mass 446.1586 ($C_{24}H_{30}O_4S_2$); Anal. Calcd. for $C_{24}H_{30}O_4S_2$: C, 64.54; H, 6.77; S, 14.36; Found: C, 64.52; H, 6.70; S, 14.44.

2-[(4-S-(N-Ethylcarbamoyl)thiophenyl]-5,5-dimethyl-1,3-dioxane (4)

To the crude thiol 3 (6.60 g, 29.5 mmol) was added ethyl isocyanoacetate (2.33 mL, 29.5 mmol) followed by phenylthiotrimethylsilane (0.568 mL, 3.00 mmol). The reaction mixture was stirred for 3 h at room temperature. During this time the mixture gradually solidified to a pale yellow solid. Then n-pentane (5 mL) was added and the suspension was filtered and washed thoroughly with n-pentane. The yellowish crystals were dissolved in hot toluene and hexanes was added. After standing for a few hours, off-white crystals were collected (4.01 g, yield 45.2% from sulfoxide 2). mp 117–118° C.; $^1H$ NMR ($CDCl_3$) δ0.81 (s, 3H, $CH_3C$), 1.08 (t, 3H, $CH_3$—$CH_2$, J=7.2 Hz), 1.29 (s, 3H, $CH_3C$), 3.2–3.3 (m, 2H, $CH_2N$), 3.67 (AB/2, 2H, $CH_2O$, J=10.8 Hz), 3.78 (AB/2, 2H, $CH_2O$, J=11.1 Hz), 5.42 (s, 1H, acetal), 5.57 (bs, 1H, NH), 7.58 (bs, 4H, ArH); $^{13}C$ NMR ($CDCl_3$) δ15.5, 22.6, 23.7, 30.9, 37.2, 78.3, 101.5, 128.1, 130.0, 136.0, 140.7, 166.4; EI-MS obsd 295.1235, calcd exact mass 295.1242 ($C_{15}H_{21}NO_3S$); Anal. Calcd. for $C_{15}H_{21}NO_3S$: C, 60.99; H, 7.17; N, 4.74; S, 10.86; Found: C, 61.16; H, 7.05; N, 4.70; S, 11.02.

2-[(4-S-(2,4-Dinitrophenyl)thiophenyl]-5,5-dimethyl-1,3-dioxane (5)

Crude thiol 3 (1.00 g, 4.46 mmol) was mixed with 2,4-dinitrofluorobenzene (830 mg, 4.46 mmol). After heating to 35 ° C., cesium fluoride (1.35 g, 8.92 mmol) was added. The yellow mixture was stirred and heated at 45° C. for 1 h. Next toluene (10 mL) was added and the hot suspension was filtered to remove insoluble materials. The filtrate was evaporated to dryness, giving an orange oil. The crude product was chromatographed on silica ($CH_2Cl_2$/hexanes 1:2) affording a yellow oil, which finally was crystallized from hot ethanol, affording yellow crystals (1.2 g, 63% from sulfoxide 2). mp 132–133° C.; $^1H$ NMR ($CDCl_3$) δ0.77 (s, 3H, $CH_3C$), 1.24 (s, 3H, $CH_3C$), 3.63 (AB/2, 2H, $CH_2O$, J=10.8 Hz), 3.74 (AB/2, 2H, $CH_2O$, J=11.1 Hz), 5.40 (s, 1H, acetal), 6.93 (d, 1H, ArH-5, J=8.7 Hz), 7.57 (AA'BB', 4H, ArH), 8.00 (dd, 1H, ArH-6, J=8.7 Hz, J=2.1 Hz), 8.99 (d, 1H, ArH-3, J=2.1 Hz); $^{13}C$ NMR ($CDCl_3$) δ22.4, 23.6, 30.9, 78.4, 101.2, 122.0, 127.5, 129.2, 129,6, 130.0, 136.4, 142.2, 144.9, 148.8; EI-MS obsd 390.0873, calcd exact mass 390.0886 ($C_{18}H_{18}N_2O_6S$); Anal. Calcd. for $C_{18}H_{18}N_2O_6S$: C, 55.38; H, 4.65; N, 7.18; S, 89.21; Found: C, 55.50; H, 4.64; N, 7.12; S, 8.30.

2-[(4-S-(9-Pivaloylthiophenyl]-5,5-dimethyl-1,3-dioxane (6)

Crude thiol 3 (1.15 g, 50.0 mmol) was dissolved in methanol (10 mL). To this solution was added a freshly prepared solution of sodium methoxide [from Na (117 mg, 50.0 mmol) and MeOH (50 mL)]. After 15 min the mixture was evaporated to dryness and the orange solid was dried under vacuum. Then the solid was dissolved in anhydrous DMF (15 mL) at room temperature and a solution of 9-chloromethylanthracene (1.13 g, 50.0 mmol) in DMF (10 mL) was added. The reaction mixture was stirred at room temperature for 72 h. The DMF was evaporated under reduced pressure, and the resulting yellow oil was chromatographed on alumina (hexanes/$CH_2Cl_2$). The resulting yellow crystals were recrystallized from $CH_2Cl_2$/hexanes to afford 1.17 g of the desired product (56.4%). mp 158–159° C.; $^1H$ NMR ($CDCl_3$) δ0.84 (s, 3H, $CH_3C$), 1.37 (s, 3H, $CH_3C$), 3.69 (AB/2, 2H, $CH_2O$, J=10.8 Hz), 3.84 (AB/2, 2H, $CH_2O$, J=10.8 Hz), 5.01 (s, 2H, $CH_2S$), 5.44 (s, 1H, acetal), 7.4–7.6 (m, 8H, anthracene), 8.01, 8.26 (AA'BB', 4H, ArH), 8.42 (s, 1H, anthracene); $^{13}C$ NMR ($CDCl_3$) δ22.6, 23.8, 30.9, 32.7, 78.4, 102.0, 124.8, 125.8, 127.1, 127.6, 128.1, 128.5, 129.7, 129.9, 130.8, 132,2, 137.5, 139.3; FAB-MS obsd 414.1653, calcd exact mass 414.1654 ($C_{27}H_{26}O_2S$); Anal. Calcd. for $C_{27}H_{26}O_2S$: C, 78.22; H, 6.32; S, 7.73; Found: C, 78.05; H, 6.24; S, 7.63.

2-[(4-S-Pivaloylthiophenyl]-5,5-dimethyl-1,3-dioxane (7)

Crude thiol 3 (2.24 g, 10.0 mmol) was dissolved in $CH_2Cl_2$ (10 mL) and methanol (10 mL) was added. To this solution was added a freshly prepared solution of sodium methoxide [from Na (230 mg, 10.0 mmol) and MeOH (5 mL)]. After 30 min pivaloyl chloride (1.40 mL, 11.4 mmol) was added and the mixture was stirred for an additional 3 h at room temperature. After evaporation of all volatile components, the residual oil was chromatographed on silica, affording a mixture of less polar compounds. The yellowish oil was further chromatographed using centrifugal preparative chromatography to afford a mixture of the title compound and the corresponding disulfide. The mixture was dissolved in $CH_2Cl_2$ and MeOH was added. Next $CH_2Cl_2$ was flushed out with argon. The crystals were filtered and dissolved in hot methanol and the mixture was carefully cooled. After 30 min crystals of the title compound were collected (502 mg, 16.0%). mp 115–116 ° C.; $^1H$ NMR ($CDCl_3$) δ0.80 (s, 3H, $CH_3C$), 1.28 (s, 3H, $CH_3C$), 1.32 (s, 9H, $C(CH_3)_3$), 3.64 (AB/2, 2H, $CH_2O$, J=10.2 Hz), 3.77 (AB/2, 2H, $CH_2O$, J=1.02 Hz), 5.41 (s, 1H, acetal), 7.40, 7.55 (AA'BB', 4H, ArH); $^{13}C$ NMR ($CDCl_3$) δ22.6, 23.7, 28.1, 30.9, 47.6, 78.3, 101.6, 127.5, 129.3, 135.4, 140.1; Anal. Calcd. for $C_{17}H_{24}O_3S$: C, 66.20; H, 7.84; S, 10.40; Found: C, 66.22; H, 7.92; S, 10.60.

4-Thiocyanatobenzaldehyde (8)

Under an argon atmosphere, a mixture of 4-iodobenzaldehyde (232 mg, 1.00 mmol), KSCN (95.0 mg, 1.00 mmol), CuSCN (120 mg, 1.00 mmol) and DMF (7.5 mL) was heated with stirring in an oil bath maintained at 140° C. for 12 h. After cooling, the mixture was diluted with toluene and water, and then filtered through a Celite bed. The aqueous phase was extracted with toluene, the organic fractions were combined and washed with water, dried and concentrated. The resulting dark oil was chromatographed on silica gel using centrifugal preparative chromatography to obtain off-white crystals (33 mg, 20%). mp 82–83° C.; $^1$H NMR (CDCl$_3$) δ7.63, 7.92 (AA'BB', 2H, ArH), 10.01 (s, 1H, CHO); $^{13}$C NMR (CDCl$_3$) δ109.4, 129.3, 131.6, 132.9, 191.3; EI-MS obsd 163.0092, calcd exact mass 163.0092 (C$_8$H$_5$NOS); Anal. Calcd. for C$_8$H$_5$NOS: C, 58.88; H, 3.09; N, 8.58; S, 19.65; Found: C, 58.85; H, 2.99; N, 8.61; S, 19.68.

4-S-Acetylthiobenzaldehyde (9)

4-Methylthiobenzaldehyde (4.45 mL, 0.033 mol) and sodium thiomethoxide (10 g, 0.13 mol) were suspended in HMPA (100 mL) and the reaction mixture was heating with stirring at 100° C. for 18 h. The resulting brown suspension was cooled and acetyl chloride (10 mL) was added. After 2 h the resulting suspension was poured into water and diethyl ether was added. The ethereal layer was extracted with water three times, dried and evaporated. Next chromatography was performed (silica, CH$_2$Cl$_2$/hexanes, 1:1). A yellow oil was collected containing the title compound with some impurities (3.33 g, crude yield 55.5%). This oil was recrystallized from ethanol giving off-white crystals (1.05 g, 18.3%). mp 44–45° C. (lit. 46° C., Zhdanov et al. (1970) *Zh. Organ. Khim.*, 6: 554–559, Engl. Transl. (1970), 6: 551–555); $^1$H NMR (CDCl$_3$) δ2.44 (s, 3H, COCH3), 7.56 (AA'BB', 2H, ArH), 7.87 (AA'BB', 2H, ArH), 10.00 (s, 1H, CHO); $^{13}$C NMR (CDCl$_3$) δ31.2, 130.6, 135.2, 136.1, 137.1, 192.1, 192.9; Anal. Calcd. for C$_9$H$_8$O$_2$S: C, 59.98; H, 4.47; S, 17.79; Found: C, 59.58; H, 4.52; S, 17.78.

m-(Thiocyanatomethyl)benzaldehyde (10)

To a solution of 300 mg of m-(bromomethyl)benzaldehyde (Wagner et al. (1997) *Tetrahedron*, 53: 6755–6790) (1.5 mmol) in 5 mL of methanol was added a solution of 321 mg of potassium thiocyanate (3.3 mmol) in 4 mL of methanol under stirring at ambient temperature. After a few minutes a precipitate formed. The reaction was monitored by TLC and stopped by adding 20 mL of H$_2$O when no starting material was detectable. 30 mL of ether was added and the phases were separated. The aqueous phase was washed twice with 20 mL of ether and the combined organic phases were dried (Na$_2$SO$_4$). Column chromatography over flash silica gel with ether/hexanes (1:2) gave 198 mg (1.1 mmol, 74% yield) of a slightly yellow oil which solidified upon standing at 0° C. Recrystallization (ether/hexanes) gave colorless crystals (mp 39° C.). IR (neat): ν=3060 cm$^{-1}$ (m, arom. CH), 2996 (m, CH), 2832 (s, CH), 2751 (m, CH), 2149 (s, CN), 1695 (s, C=O), 1603 (s, arom. C=C), 1450 (m, arom. C=C), 1424 (m), 1394 (w), 1294 (w), 1145 (s), 1084 (w), 1006 (w), 960 (w), 908 (w), 881 (w), 803 (s), 754 (w), 696 (s), 652 (s); $^1$H NMR (300.5 MHz, CDCl$_3$): δ=4.22 (s, 2H, CH$_2$), 7.55–7.69 (m, 2H, ArH), 7.86–7.93 (m, ArH), 10.04 (s, 1H, CHO); $^{13}$C NMR (75.6 MHz, CDCl$_3$, APT): δ=32.7 (+, CH$_2$), 111.4 (+, CN), 129.6 (−, CH), 129.8 (−, CH), 130.1 (−, CH), 134.6 (−, CH), 135.7 (+, C$_q$), 136.8 (+, C$_q$), 191.4 (−, CHO); GC-MS (EI) obsd 177 [M$^+$], 149 [M$^+$−CO], 120, 119 [M$^+$−SCN], 91 [M$^+$−SCN−CO], 90, 89, 77 [C$_6$H$_5^+$], 65, 63; Anal. Calcd for C$_9$H$_7$NOS, C, 60.99; H, 3.98; N, 7.90; S, 18.09. Found: C, 60.75; H, 4.05; N, 7.86; S, 18.19.

General Procedure For Synthesis of Porphyrins 15–18, 19–20 and 22–24

Acetal (4, 5, 6 or 7) (0.730 mmol) was dissolved in CH$_2$Cl$_2$ (1 mL) and trifluoroacetic acid (2 mL) was added. The mixture was stirred at room temperature overnight. After evaporation of the reaction mixture to dryness, the residue was redissolved in CHCl$_3$ (40 mL). Alternatively, aldehyde 9 or 4-methylthiobenzaldehyde (0.730 mmol) was added to CHCl$_3$ (40 mL). Next samples of the other aldehyde (2.20 mmol), pyrrole (0.200 mL, 2.92 mmol) and BF$_3$OEt$_2$ (0.090 mL, 0.71 mmol) were added. The reaction mixture was stirred at room temperature for 90 min. Then DDQ (500 mg, 2.20 mmol) was added and the reaction mixture was gently refluxed for 1 h. After cooling, the reaction mixture was passed over a short silica column (CH$_2$Cl$_2$) affording porphyrins usually free from dark pigments and quinone species. Further purification details are described for each case as follows.

5,10,15-Trimesityl-20-[4-S-(N-ethylcarbamoyl)thiophenyl]porphyrin (15)

The mixture of porphyrins was loaded onto a silica column (4×30 cm, toluene). The title porphyrin comprised the second purple band, affording 72 mg (12%). $^1$H NMR (CDCl$_3$) δ−2.47 (s, 2H, NHpyrrole), 1.32 (t, 3H, CH$_3$—CH$_2$, J=7.2 Hz), 1.94 (s, 18H, ArCH$_3$), 2.69 (s, 9H, ArCH$_3$), 3.4–3.6 (m, 2H, CH$_2$N), 5.65 (bs, 1H, NH), 7.35 (s, 6H, ArH), 8.00, 8.33 (AA'BB', 4H, ArH), 8.72 (s, 4H, β-pyrrole), 8.78 (d, 2H, β-pyrrole, J=4.2 Hz), 8.87 (d, 2H, β-pyrrole, J=4.2 Hz); LD-MS calcd av mass 844.1, obsd 844.6 [M$^+$], 773.1 [M$^+$−CONHEt]; FAB-MS obsd 843.4019, calcd exact mass 843.3971 (C$_{56}$H$_{53}$N$_5$OS); λ$_{abs}$ (CH$_2$Cl$_2$) 419, 515, 548, 591 nm.

5,10,15-Trimesityl-20-[4-S-(2,4-dinitrophenyl)thiophenyl]porphyrin (16)

The mixture of porphyrins was purified by preparative centrifugal TLC (silica, toluene/hexanes, 1:2). The title porphyrin comprised the second purple band, affording 70 mg (10%). $^1$H NMR (CDCl$_3$) δ−2.44 (s, 2H, NHpyrrole), 1.95 (s, 18H, ArCH$_3$), 2.71 (s, 9H, ArCH$_3$), 7.30 (d, 1H, ArH, J=8.1 Hz), 7.37 (s, 6H, ArH), 7.60 (d, 1H, ArH, J=8.7 Hz), 8.00, 8.49 (AA'BB', 4H, ArH), 8.75 (s, 4H, β-pyrrole), 8.8–9.0 (m, 4H, β-pyrrole), 9.30 (d, 1H, ArH, J=2.1 Hz); LD-MS calcd av mass 938.4, obsd 938.0; FAB-MS obsd 938.3632, calcd exact mass 938.3614 (C$_{59}$H$_{50}$N$_6$O$_4$S); λ$_{abs}$ (CH$_2$Cl$_2$) 419, 515, 549, 591, 646 nm.

5,10,15-Trimesityl-20-[4-S-(9-anthrylmethyl)thiophenyl]porphyrin (17)

The mixture was chromatographed on an alumina column (toluene/hexanes, 1:4). The resulting mixture of porphyrins was purified by preparative centrifugal TLC (silica, toluene/hexanes, 1:3). The title porphyrin comprised the second purple band, affording 28 mg (4.0%). $^1$H NMR (CDCl$_3$) δ−2.51 (s, 2H, NHpyrrole), 1.90 (s, 18H, ArCH$_3$), 2.66 (s, 9H, ArCH$_3$), 5.43(s, 2H, CH$_2$S), 7.1–7.8 (m, 5H, anthracene), 7.31 (s, 6H, ArH), 7.79, 8.52 (AA'BB', 4H, ArH), 8.0–8.2 (m, 4H, anthracene), 8.68 (s, 4H, β-pyrrole), 8.75 (d, 2H, β-pyrrole, J=4.5 Hz), 8.80 (d, 2H, ,pyrrole, J=4.5 Hz); LD-MS calcd av mass 962.5, obsd 964.0, 787.4 [M$^+$−C$_{14}$H$_8$], 773.1 [M$^+$−C$_{15}$H$_{10}$]; FAB-MS obsd 962.4368, calcd exact mass 962.4382 (C$_{68}$H$_{58}$N$_4$S); λ$_{abs}$ (CH$_2$Cl$_2$) 420, 515, 549, 593, 648 nm.

5,10,15-Trimesityl-20-[4-S-pivaloyl-thiophenyl]porphyrin (18)

The mixture was chromatographed on a silica column (toluene/hexanes, 1:1). The title porphyrin comprised the second purple band, affording 68 mg (11%). $^1$H NMR (CDCl$_3$) δ−2.49 (s, 2H, NH), 1.52 (s, 9H, C(CH$_3$)$_3$), 1.92 (s, 18H, ArCH$_3$), 2.68 (s, 9H, ArCH$_3$), 7.35 (s, 6H, ArH), 7.83, 8.30 (AA'BB', 4H, ArH), 8.70 (s, 4H, β-pyrrole), 8.75 (d, 2H, β-pyrrole, J=5.4 Hz), 8.88 (d, 2H, β-pyrrole, J=5.4 Hz); LD-MS calcd av mass 856.4, obsd 858.6, 831.5 [M$^+$−C$_2$H$_6$], 774.2 [M$^+$−COC(CH$_3$)$_3$]; FAB-MS obsd 856.4186, calcd exact mass 856.4175 (C$_{58}$H$_{56}$N$_4$OS); λ$_{abs}$ (CH$_2$Cl$_2$) 419, 515, 548, 591, 646 nm.

5,10,15-Trimesityl-20-[4-S-methylthiophenyl]porphyrin (19)

The mixture was chromatographed on a silica column (toluene/hexanes, 1:1). The resulting mixture was next chromatographed on silica column (toluene/hexanes, 1:4). The title porphyrin comprised the second purple band, affording 57 mg (10%). $^1$H NMR (CDCl$_3$) δ −2.49 (s, 2H, NH), 1.92 (s, 18H, ArCH$_3$), 2.68 (s, 9H, ArCH$_3$), 2.79 (s, 3H, SCH$_3$), 7.33 (s, 6H, ArH), 7.67, 8.18 (AA'BB', 4H, ArH), 8.70 (s, 4H, β-pyrrole), 8.74 (d, 2H, β-pyrrole, J=5.1 Hz), 8.87 (d, 2H, β-pyrrole, J=5.1 Hz); LD-MS calcd av mass 786.4, obsd 786.9; FAB-MS obsd 786.3790, calcd exact mass 786.3756 (C$_{54}$H$_{50}$N$_4$S); λ$_{abs}$ (CH$_2$Cl$_2$) 420, 515, 550, 592, 648 nm.

5,10,15-Trimesityl-20-[4-S-acetylthiophenyl]porphyrin (20)

The mixture was chromatographed on a silica column (toluene/hexanes 1: 1, then toluene). The title porphyrin comprised the second purple band, affording 62 mg (10.5%). $^1$H NMR (CDCl$_3$) δ −2.46 (s, 2H, NH), 1.94 (s, 18H, ArCH$_3$), 2.66 (s, 3H, COCH$_3$), 2.70 (s, 9H, ArCH$_3$), 7.35 (s, 6H, ArH, 7.88, 8.35 (AA'BB', 4H, ArH), 8.73 (s, 4H, β-pyrrole), 8.79 (d, 2H, β-pyrrole, J=4.2 Hz), 8.89 (d, 2H, β-pyrrole, J=4.2 Hz); LD-MS calcd av mass 814.4, obsd 815.7, 813.9 [M$^+$+15]; 787.7 [M$^+$−CH$_3$CO+15], 773.7 [M$^+$−CH$_3$CO]; FAB-MS obsd 814.3694, calcd exact mass 814.3705 (C$_{55}$H$_{50}$N$_4$OS); λ$_{abs}$ (CH$_2$Cl$_2$) 419, 515, 548, 591, 647 nm.

5,10,15-Tris(2,4,6-trimethoxyphenyl)-20-[4-S-(N-ethylcarbamoyl)thiophenyl]porphyrin (22)

Purification was performed by preparative centrifugal chromatography (silica, CH$_2$Cl$_2$/MeOH, 98:2). The title compound was obtained as a ~1:1 mixture with 5,10,15,20-tetrakis(2,4,6-trimethoxyphenyl)porphyrin. The presence of the title compound was confirmed by mass spectrometry (LD-MS C$_{56}$H$_{53}$N$_5$O$_{10}$S calcd av mass 987.4, obsd 988.6). This mixture was not purified further but was used in the metalation reaction to prepare Zn-22.

5,10,15-Tris(2,3,4,5,6-pentafluorophenyl)-20-[4-S-(N-ethylcarbamoyl)thiophenyl]-porphyrin (23)

The mixture of porphyrins was chromatographed on a silica column (4×30 cm, hexanes/CH$_2$Cl$_2$, 2:1). The title porphyrin comprised the second purple band, affording 72 mg (10%). $^1$H NMR (CDCl$_3$) δ −2.74 (s, 2H, NHpyrrole), 1.32 (t, 3H, CH$_3$—CH$_2$, J=7.2 Hz), 3.5–3.6 (m, 2H, CH$_2$N), 5.67 (bs, 1H, NH), 8.00, 8.32 (AA'BB', 4H, ArH), 8.94 (d, 2H, β-pyrrole, J=5.1 Hz), 9.02 (s, 4H, β-pyrrole), 9.09 (d, 2H, β-pyrrole, J=4.2 Hz); LD-MS calcd av mass 987.1, obsd 989.9, 918.7 [M$^+$−CONHEt]; FAB-MS obsd 987.1136, calcd exact mass 987.1149 (C$_{47}$H$_{20}$F$_{15}$N$_5$OS); λ$_{abs}$ (CH$_2$Cl$_2$) 415, 509, 540, 584, 638 nm.

5,10,15-Tri-n-pentyl-20-[4-S-(N-ethylcarbamoyl)thiophenyl]porphyrin (24)

The free base was purified by preparative centrifugal chromatography (silica/CH$_2$Cl$_2$/hexanes, 5:1) followed by column chromatography (silica/CH$_2$Cl$_2$/toluene, 4:1). The title porphyrin comprised the second purple band, affording 9 mg (4%). $^1$H NMR (CDCl$_3$) δ −2.62 (s, 2H, NH), 1.00–1.10 (m, 9H, CH$_3$—CH$_2$), 1.30–1.70 (m, 9H, CH$_2$ aliphatic+CH$_3$—CH$_2$—N), 1.75–1.90 (m, 6H, CH$_2$), 2.45–2.70 (m, 6H, CH$_2$), 3.50–3.62 (m, 4H, N—CH$_2$), 4.90–5.10 (m, 6H, CH$_2$-porphyrin), 5.63 (bt, 1H, NH, J=5.1Hz), 7.98, 8.26 (AA'BB', 4H, ArH), 8.85 (d, 2H, β-pyrrole, J=4.2 Hz), 9.43 (d, 2H, β-pyrrole, J=5.1 Hz); 9.52–9.62 (m, 4H, β-pyrrole); LD-MS calcd av mass 699.4, obsd 700.7; FAB-MS obsd 699.3996, calcd exact mass 699.3971 (C$_{44}$H$_{53}$N$_5$OS); ) λ$_{abs}$ (CH$_2$Cl$_2$) 419, 519, 554, 598, 656 nm.

General Procedure For Zinc Insertion

Porphyrin (0.040 mmol) was dissolved in CH$_2$Cl$_2$ (15 mL) and a solution of Zn(OAc)$_2$·2H$_2$O (880 mg, 4.00 mmol) in methanol (15 mL) was added. The reaction mixture was stirred overnight at room temperature. After metalation was complete (TLC, fluorescence excitation spectroscopy), the reaction mixture was washed with water and 10% NaHCO$_3$, dried (Na$_2$SO$_4$), filtered and rotary evaporated to a purple solid. Purification was achieved by chromatography on silica.

Zn(II)-5,10,15-Trimesityl-20-[4-S-(N-ethylcarbamoyl)thiophenyl]porphyrin (Zn-15)

Column chromatography (silica, CH$_2$Cl$_2$) afforded 29 mg (75%). $^1$H NMR (CDCl$_3$) δ1.30 (t, 3H, CH$_3$—CH$_2$, J=7.5 Hz), 1.87 (s, 18H, ArCH$_3$), 2.66 (s, 9H, ArCH$_3$), 3.4–3.6 (m, 2H, CH$_2$N), 5.61 (bs, 1H, NH), 7.31 (s, 6H, ArH), 7.93, 8.30 (AA'BB', 4H, ArH), 8.74 (s, 4H, β-pyrrole), 8.80 (d, 2H, β-pyrrole, J=5.1 Hz), 8.88 (d, 2H, β-pyrrole, J=4.2 Hz); LD-MS calcd av mass 905.3, obsd 906.7, 835.7 [M$^+$−CONHEt]; FAB-MS obsd 905.3098, calcd exact mass 905.3106 (C$_{56}$H$_{51}$N$_5$OSZn); λ$_{abs}$ (CH$_2$Cl$_2$) 421, 549 nm.

Zn(II)-5,10,15-Trimesityl-20-[4-S-(2,4-dinitrophenyl)thiophenyl]porphyrin (Zn-16)

Column chromatography (silica, toluene/hexanes) afforded 34 mg (85%). $^1$H NMR (CDCl$_3$) δ1.87 (s, 18H, ArCH$_3$), 2.64 (s, 9H, ArCH$_3$), 7.26 (d, 1H, ArH, J=9.0 Hz), 7.29 (s, 6H, ArH), 7.54 (d, 1H, ArH, J=9.0 Hz), 7.99, 8.44 (AA'BB', 4H, ArH), 8.75 (s, 4H, β-pyrrole), 8.86 (AB, 4H, β-pyrrole, J=4.5 Hz), 9.23 (d, 1H, ArH, J=3.0 Hz); LD-MS calcd av mass 1000.3, obsd 1000.3; FAB-MS obsd 1000.2726, calcd exact mass 1000.2749 (C$_{59}$H$_{48}$N$_6$O$_4$SZn); λ$_{abs}$ (CH$_2$Cl$_2$) 422, 550 nm.

Zn(II)-5,10,15-Trimesityl-20-[4-S-(9-anthrylmethyl)thiophenyl]porphyrin (Zn-17)

The product was purified by preparative centrifugal TLC (silica, hexanes/CH$_2$Cl$_2$) 31 mg (74%). $^1$H NMR (CDCl$_3$) δ1.85 (s, 9H, ArCH$_3$), 1.88 (s, 9H, ArCH$_3$), 2.65 (s, 9H, ArCH$_3$), 5.36 (s, 2H, CH$_2$S), 7.1–8.5 (m, 19H, anthracene+ArH), 8.72 (s, 2H, β-pyrrole), 8.73 (s, 2H, β-pyrrole), 8.8–9.0 (m, 4H, β-pyrrole); LD-MS calcd av mass 1024.4, obsd 1027.3, 834.9 [M$^+$−C$_{15}$H$_{10}$]; FAB-MS obsd 1024.3529, calcd exact mass 1024.3517 (C$_{68}$H$_{56}$N$_4$SZn); λ$_{abs}$ (CH$_2$Cl$_2$) 421, 550 nm.

Zn(II)-5,10,15-Trimesityl-20-[4-S-pivaloylthiophenyl]porphyrin (Zn-18)

The product was purified on a silica column (toluene/hexanes, 1:1), affording 31 mg (85%). $^1$H NMR (CDCl$_3$) δ1.50 (s, 9H, C(CH$_3$)$_3$), 1.87 (s, 18H, ArCH$_3$), 2.65 (s, 9H, ArCH$_3$), 7.31 (s, 6H, ArH), 7.79, 8.29 (AA'BB', 4H, ArH), 8.74 (s, 4H, β-pyrrole), 8.79 (d, 2H, β-pyrrole, J=4.2 Hz), 8.91 (d, 2H, β-pyrrole, J=4.2 Hz); LD-MS calcd av mass 918.3, obsd 919.5, 891.4 [M$^+$−C$_2$H$_6$], 835.3 [M$^+$−COC(CH$_3$)$_3$]; FAB-MS obsd 918.3332, calcd exact mass 918.3310 (C$_{58}$H$_{54}$N$_4$OSZn); λ$_{abs}$ (CH$_2$Cl$_2$) 422, 549 nm.

Zn(II)-5,10,15-Trimesityl-20-[4-S-methylthiophenyl]porphyrin (Zn-19)

The mixture was chromatographed on a silica column (toluene/hexanes, 1:1). The resulting mixture was next chromatographed on a silica column (toluene/hexanes, 1:4). The title porphyrin comprised the second purple band, affording 31 mg (90%). $^1$H NMR (CDCl$_3$) δ1.84 (s, 18H, ArCH$_3$), 2.63 (s, 9H, ArCH$_3$), 2.74 (s, 3H, SCH$_3$), 7.26 (s, 6H, ArH), 7.59, 8.13 (AA'BB', 2H, ArH), 8.70 (s, 4H, β-pyrrole), 8.75 (d, 2H, β-pyrrole, J=5.1 Hz), 8.87 (d, 2H, β-pyrrole, J=5.1 Hz); LD-MS calcd av mass 848.3, obsd 851.5; FAB-MS obsd 848.2913, calcd exact mass 848.2891 (C$_{54}$H$_{48}$N$_4$SZn); λ$_{abs}$ (CH$_2$Cl$_2$) 421, 550 nm.

Zn(II)-5,10,15-Trimesityl-20-[4-S-acetylthiophenyl] porphyrin (Zn-20)

Method 1

(From 20 by general zinc insertion procedure). Purification by chromatography (silica, toluene/CH$_2$Cl$_2$). Yield 82%.

Method 2

Zn(II)-porphyrin Zn-15 (9.0 mg, 0.010 mmol) was dissolved in CH$_2$Cl$_2$ (20 mL) and the solution was carefully flushed with argon. Next a solution of sodium methoxide [freshly prepared from sodium (23 mg, 1.0 mmol) and MeOH (10 mL) under argon] was added. The reaction mixture was stirred under argon at room temperature for 1 h. Next acetyl chloride (1 mmol, 0.7 mL) was added and the mixture was evaporated to dryness. The mixture of porphyrins was dissolved in CH$_2$Cl$_2$ and chromatographed (silica, hexanes/CH$_2$Cl$_2$) affording 6.3 mg (72%). $^1$H NMR (CDCl$_3$) δ1.85 (s, 18H, ArCH$_3$), 2.63 (s, 9H, ArCH$_3$), 2.61 (s, 3H, CH$_3$CO), 7.28 (s, 6H, ArH), 7.46, 8.07 (AA'BB', 4H, ArH), 8.70 (s, 4H, β-pyrrole), 8.74 (d, 2H, β-pyrrole, J=5.1 Hz), 8.83 (d, 2H, β-pyrrole, J=5.1 Hz); LD-MS calcd av mass 876.3, obsd 874.6; FAB-MS obsd 878.2983, calcd exact mass 878.2997 (C$_{55}$H$_{50}$N$_4$OSZn).

Zn(II)-5,10,15-Trimesityl-20-[4-mercaptophenyl]porphyrin (Zn-21)

A sample of Zn-15 (9.0 mg, 0.010 mmol) was dissolved in CH$_2$Cl$_2$ (20 mL) and the solution was carefully flushed with argon. Next a solution of sodium methoxide [freshly prepared from sodium (23 mg, 1 mmol) and MeOH (10 mL) and also flushed with argon] was added. The reaction mixture was stirred at room temperature for 1 h. Next HCl (0.2 mL, 5 M soln.) was added and the mixture was evaporated to dryness. The mixture of porphyrins was dissolved in CH$_2$Cl$_2$ and chromatographed (silica, hexanes/CH$_2$Cl$_2$) affording 4.3 mg (51%). $^1$H NMR(CDCl$_3$) δ1.89 (s, 18H, ArCH$_3$), 2.66 (s, 9H, ArCH$_3$), 7.31 (s, 6H, ArH), 7.64, 8.22 (AA'BB', 2H, ArH), 8.76 (s, 4H, β-pyrrole), 8.8–9.0 (m, 4H, β-pyrrole); LD-MS calcd av mass 834.3, obsd 834.0; FAB-MS obsd 834.2071, calcd exact mass 834.2735 (C$_{53}$H$_{46}$N$_4$SZn).

Zn(II)-5,10,15-Tris(2,4,6-trimethoxyphenyl)-20-[4-S-(N-ethylcarbamoyl)thiophenyl]-porphyrin (Zn-22)

30.0 mg of a mixture of the desired free base A$_3$B-porphyrin and the corresponding A$_4$-porphyrin was metalated according to the general procedure. The desired chelate was purified by preparative centrifugal chromatography (silica/CH$_2$Cl$_2$/MeOH, 99:1), affording 10.0 mg (1.3% from acetal 5). $^1$H NMR (CDCl$_3$) δ1.27 (t, 3H, CH$_3$CH$_2$, J=7.2 Hz), 3.4–3.6 (m, 2H, CH$_2$N), 3.49 (s, 18H, OCH$_3$), 4.09 (s, 9H, OCH$_3$), 5.57 (bt, 1H, NH, J=5.1 Hz), 6.57 (s, 6H, ArH), 7.89, 8.26 (AA'BB', 4H, ArH), 8.81 (d, 2H, β-pyrrole, J=4.5 Hz), 8.86 (d, 2H, β-pyrrole, J=4.5 Hz), 8.84 (s, 4H, β-pyrrole); LD-MS calcd av mass 1049.3, obsd 1052.7, 981.5 [M$^+$-CONHEt]; FAB-MS obsd 1049.2666, calcd exact mass 1049.2648 (C$_{56}$H$_{51}$N$_5$O$_{10}$SZn); λ$_{abs}$ (CH$_2$Cl$_2$) 423, 549 nm Zn(II)-5,10,15-Tris(2,3,4,5,6-pentafluorophenyl)-20-[4-mercaptophenyl]porphyrin (Zn-25)

Refluxing a mixture of porphyrin 25 and Zn(OAc)$_2$.2H$_2$O for 8 h followed by purification on silica (CH$_2$Cl$_2$) afforded 25 mg (63% yield). $^1$H NMR (CDCl$_3$) δ3.79 (s, 1H, SH), 7.67, 8.09 (AA'BB', 4H, ArH), 8.93 (d, 2H, β-pyrrole, J=4.2 Hz), 9.00 (s, 4H, β-pyrrole), 9.09 (d, 2H, β-pyrrole, J=4.2 Hz); LD-MS calcd av mass 978.0, obsd 975.4; FAB-MS obsd 977.9925, calcd exact mass 977.9913 (C$_{44}$H$_{13}$F$_{15}$N$_4$SZn). λ$_{abs}$ (CH$_2$Cl$_2$) 416, 545 nm.

Zn(II)-5,10,15-Tri-n-pentyl-20-[4-mercaptophenyl]porphyrin (Zn-26)

The product was purified by column chromatography (silica/CH$_2$Cl$_2$) followed by preparative centrifugal TLC (silica, hexanes/CH$_2$Cl$_2$, 1:9), affording 12 mg (44%). $^1$H NMR (CDCl$_3$) δ0.80–1.40 (m, 12H, CH$_3$—CH$_2$+CH$_3$—CH$_2$—N), 1.50–1.70 (m, 6H, CH$_2$ aliphatic), 1.75–1.95 (m, 6H, CH$_2$), 2.40–2.60 (m, 6H, CH$_2$), 4.70–4.90 (m, 6H, CH$_2$-porphyrin), 8.17, 8.28 (AB'BB', 4H, ArH), 8.95 (d, 2H, β-pyrrole, J=5.1 Hz), 9.35–9.48 (d, 6H, β-pyrrole); LD-MS calcd av mass 690.3, obsd 690.4, 633.1 [M$^+$-C$_4$H$_9$]; FAB-MS obsd 690.2706, calcd exact mass 690.2735 (C$_{41}$H$_{46}$N$_4$SZn); λ$_{abs}$ (CH$_2$Cl$_2$) 419, 554 nm.

Mg(II)-5,10,15-Trimesityl-20-[4-mercaptophenyl]porphyrin (Mg-21)

Porphyrin 20 (16 mg, 0.020 mmol) was dissolved in CH$_2$Cl$_2$ (5 mL) and MgI$_2$ (56 mg, 0.20 mmol) and DIEA (0.070 mL, 0.40 mmol) were added. After 10 min the mixture was diluted with CH$_2$Cl$_2$ (20 mL), washed with 10% NaHCO$_3$ and dried. The resulting pink-violet residue was chromatographed on an alumina column (CH$_2$Cl$_2$/MeOH, 100:1, 100:2, 100:4) to afford the pink-violet product (5.0 mg, 31%). $^1$H NMR (CDCl$_3$) δ1.80 (s, 18H, ArCH$_3$), 2.61 (s, 9H, ArCH$_3$), 7.23 (s, 6H, ArH), 7.8–8.1 (m, 4H, ArH), 8.5–8.9 (m, 8H, β-pyrrole); LD-MS calcd av mass 795.3, obsd 797.4; FAB-MS obsd 794.3278, calcd exact mass 794.3294 (C$_{53}$H$_{46}$N$_4$SMg); λ$_{abs}$ (CH$_2$Cl$_2$) 426, 565, 605 nm.

5,10,15,20-Tetrakis[m-(thiocyanatomethyl)phenyl]porphyrin (27)

A solution of 513 mg of m-(thiocyanatomethyl) benzaldehyde (10, 2.9 mmol) and 0.20 mL of pyrrole (193 mg, 2.9 mmol) in 300 mL of CHCl$_3$ was purged with argon for 30 min. Under stirring at ambient temperature 12 μL of BF$_3$.O(Et)$_2$ (13 mg, 0.1 mmol) and 180 μL of TFA (266 mg, 2.3 mmol) were added. Soon the solution turned yellow and later to dark red. After 2 h an additional 90 μL of BF$_3$.O(Et)$_2$ (98 mg, 0.7 mmol) was added. After 2 h 500 μL of TEA (364 mg, 3.6 mmol) and 583 mg of o-tetrachlorobenzoquinone (2.4 mmol) were added and the mixture was refluxed for 1 h. The mixture was cooled to room temperature and the solvents were removed under reduced pressure. Column chromatography over flash silica gel with ether/hexanes (3:1) gave 119 mg (0.1 mmol, 18% yield) of a dark purple solid. IR (neat) ν=2953 (m, CH), 2917(s, CH), 2846 (m, CH), 2152 (m, CN), 1470 (m), 1392 (w), 1344 (w), 1152 (w), 1082 (w); $^1$H NMR (300.5 MHz, CDCl$_3$): δ=−2.84 (s, 2H, NH), 4.44 (s, 8H, CH$_2$), 7.76–7.85 (m, 8H, ArH), 8.18–8.25 (m, 8H, ArH), 8.88 (s, 8H, β-pyrrole); LD-MS calcd av mass 899.1, obsd 901.7, 876.3 [M$^+$–CN], 843.5 [M$^+$–SCN], 818.1 [M$^+$–SCN–CN], 785.1 [M$^+$–2 SCN], 758.5 [M$^+$–2 SCN–CN], 726.8 [M$^+$–3 SCN], 668.0 [M$^+$–4 SCN], 577.6 [M$^+$–4 SCN–C$_7$H$_7$]; FAB-MS obsd 898.1797, calcd exact mass 898.1789 (C$_{52}$H$_{34}$N$_8$S$_4$); λ$_{abs}$ (toluene) 420, 514, 549, 590, 646 nm.

Zinc(II)-5,10,15,20-Tetrakis[m-(thiocyanatomethyl)phenyl] porphyrin (Zn-27)

To a solution of 84 mg of 5,10,15,20-tetrakis[m-(thiocyanatomethyl)phenyl]porphyrin (27, 93 μmol) in 50 mL of CHCl$_3$ was added 250 mg of Zn(OAc)$_2$.2H$_2$O (1.1 mmol) in 5 mL of methanol under stirring at ambient temperature. After completion of the metalation (checked by fluorescence excitation spectroscopy) the mixture was washed with 20 mL of 10% NaHCO$_3$ and 20 mL of H$_2$O, dried (Na2SO$_4$) and filtered. The solvents were removed under reduced pressure affording 71 mg (74 μmol, 79% yield) of a dark purple solid. Recrystallization (CH$_2$Cl$_2$/methanol) gave dark purple crystals. IR (neat): ν=2995 (m, CH), 2880 (w, CH), 2153 (m, CN), 1652 (w), 1601 (m, arom. C=C), 1478 (m), 1436 (m), 1338 (m), 1206 (m), 1070 (w), 1031 (w), 1001 (s), 934 (m), 795 (s), 707 (s); $^1$H NMR (300.5 MHz, CDCl$_3$): δ=4.44 (s, 8H, CH$_2$), 7.77–7.83 (m, 8H, ArH), 8.20–8.25 (m, 8H, ArH), 8.97 (s, 8H, β-pyrrole); LD-MS calcd av mass 962.5, obsd 958.2, 900.2 [M$^+$-SCN], 843.5 [M$^+$-2 SCN], 787.5 [M$^+$-3 SCN], 726.7 [M$^+$-4 SCN]; FAB-MS obsd 960.0959, calcd exact mass 960.0924 (C$_{52}$H$_{32}$N$_8$S$_4$Zn); λ$_{abs}$ (toluene) 422, 550, 589 nm; λ$_{em}$ (toluene) 603, 652 nm.

10,20-Diphenyl-5,15-bis[-m-(thiocyanatomethyl)phenyl] porphyrin (28)

A mixture of 316 mg of m-(thiocyanatomethyl) benzaldehyde (10, 1.8 mmol), 396 mg of 5-phenyldipyrromethane (Lee and Lindsey (1994) *Tetrahedron*, 50: 11427–11440, Littler et al. (1999) *J. Org. Chem.*, 64: 1391–1396) (1.8 mmol) and 1.07 g of NH$_4$Cl (20.0 mmol) in 200 mL of acetonitrile was purged with argon for 30 min. Under stirring at ambient temperature 23 μL of BF$_3$.O(Et)$_2$ (26 mg, 0.18 mmol) was added. Soon the solution turned to yellow and later to dark red. After 6.5 h, 607 mg of DDQ (2.7 mmol) was added. After 1 h the reaction was quenched with 0.5 mL of TEA (365 g, 3.6 mmol). The solvents were removed under reduced pressure. Purification was done by column chromatography over two flash silica gel columns with different solvent mixtures: (column 1) ether/hexanes (3:1) and (column 2) CH$_2$Cl$_2$/hexanes (gradient, start: 1:1). Two fractions of dark purple solids were obtained. I: 12 mg 10,15,20-triphenyl-5-[m-(thiocyanatomethyl)phenyl]porphyrin (17.5 μmol, 2% yield). II: 44 mg of the title compound (58.1 μmol, 7% yield). IR (neat): ν=2921 (s, CH), 2850 (m, CH), 2154 (m, CN), 1597 (m, arom. C=C), 1471 (s), 1348 (m), 1206 (m), 1181 (w), 1097 (w), 973 (s), 898 (w), 743 (s), 691 (s), 623 (s); $^1$H NMR (300.5 MHz, CDCl$_3$): δ=-2.811 (s, 2H, NH), 4.57 (s, 4H, CH$_2$), 7.71–7.83 (m, 11H, ArH), 8.17–8.25 (m, 8H, ArH), 8.84 (d, 4H, β-pyrrole, $^3$J=5.1 Hz), 8.88 (d, 4H, β-pyrrole); LD-MS calcd av mass 756.9, obsd 757.4, 699.2 [M$^+$-SCN], 641.0 [M$^+$-2 SCN]; FAB-MS obsd 756.2172, calcd exact mass 756.2130 (C$_{48}$H$_{32}$N$_6$S$_2$); λ$_{abs}$ (toluene) 420, 514, 549, 590, 647, 657 nm.

Zinc(II)-10,20-Diphenyl-5,15-bis[-m-(thiocyanatomethyl) phenyl]porphyrin (Zn-28)

A mixture of 38 mg of 10,20-diphenyl-5,15-bis[m-(thiocyanatomethyl)phenyl]porphyrin (28, 50.2 μmol) in 30 mL of CH$_2$Cl$_2$ and a solution of 140 mg of Zn(OAc)$_2$.2H$_2$O (0.64 mmol) in 5 mL of methanol were combined and stirred at ambient temperature. After completion of the metalation (checked by fluorescence excitation spectroscopy) 20 mL of H$_2$O were added. The phases were separated and the organic layer was washed with 20 mL of 5% NaHCO$_3$ and 20 mL of H$_2$O, dried (Na$_2$SO$_4$) and filtered. The solvents were removed under reduced pressure. Column chromatography over flash silica gel with CH$_2$Cl$_2$/hexanes (5:1) gave 22 mg (26.8 μmol, 53% yield) of a dark purple solid. IR (neat): ν=3049 (w, arom. CH), 2924 (s, CH), 2853 (m, CH), 2154 (m, CN), 1598 (m, arom. C=C), 1522 (w), 1480 (m), 1440 (m), 1339 (m), 1206 (m), 1070 (m), 1002 (s), 934 (w), 796 (s), 741 (m), 703 (m), 662 (m); $^1$H NMR (300.5 MHz, CDCl$_3$): δ=4.44 (s, 4H, CH$_2$), 7.70–7.90 (m, 11H, ArH), 8.16–8.28 (m, 8H, ArH), 8.93 (d, 4H, β-pyrrole, $^3$J=4.2 Hz), 8.98 (d, 4H, β-pyrrole); LD-MS calcd av mass 820.31, obsd 819.6, 792.3 [M$^+$-CN], 761.5 [M$^+$-SCN], 703.3 [M$^+$-2 SCN], 626.0 [M$^+$-2 SCN-C$_6$H$_5$], 613.5 [M$^+$-2 SCN-C$_7$H$_7$]; FAB-MS obsd 818.1275, calcd exact mass 818.1265 (C$_{48}$H$_{30}$N$_6$S$_2$Zn); λ$_{abs}$ (toluene) 424, 550, 590 nm; λ$_{em}$ (toluene) 599, 647 nm.

5,10,15,20-Tetrakis[m-(S-acetylthiomethyl)phenyl] porphyrin (29)

A solution of 101 mg of 5,10,15,20-tetrakis[m-(bromomethyl)phenyl)porphyrin (Wen et al. (1997) *J. Am. Chem. Soc.*, 119: 7726–7733, Karaman et al. (1992) *J. Am. Chem. Soc.*, 114: 4889–4898) (102 μmol) and 60 mg of potassium thioacetate (525 μmol) in 20 mL of THF was refluxed. After 5 h the mixture was cooled to room temperature. 30 mL of water was added. The mixture was cooled to room temperature and the phases were separated. The organic phase was washed with 40 mL of 5% NaHCO$_3$ solution and dried (Na$_2$SO$_4$). Column chromatography over flash silica gel with THF afforded a purple wax, which was purified by refluxing in hexanes. The mixture was filtered and the residue was dissolved in CH$_2$Cl$_2$. The solvent was removed under reduced pressure, affording 63 mg (65 μmol, 63% yield) of a purple solid. IR (neat) ν=3423 (m, NH), 3318 (m, NH), 2963 (w, CH), 2926 (w, CH), 1690 (s, CO), 1600 (w), 1562 (w), 1540 (w), 1508 (w), 1472 (w), 1420 (w), 1351 (w), 1132 (m), 1103 (w), 1018 (w), 997 (w), 957 (w), 917 (w), 800 (m), 718 (m); $^1$H NMR (300.5 MHz, CDCl$_3$): δ=-2.83 (s, 2H, NH), 2.40 (s, 12H, CH$_3$), 4.41 (s, 8H, CH$_2$), 7.65–7.75 (m, 8H, ArH), 8.06–8.17 (m, 8H, ArH), 8.84 (s, 8H, β-pyrrole); LD-MS calcd av mass 966.2 (C$_{56}$H$_{46}$N$_4$O$_4$S$_4$), obsd 967.4, 925.3 [M$^+$-COCH$_3$], 892.2 [M$^+$-SCOCH$_3$], 850.0 [M$^+$-SCOCH$_3$-COCH$_3$], 817.2 [M$^+$-2 SCOCH$_3$], 775.5 [M+-2 SCOCH$_3$-COCH$_3$; λ$_{abs}$ (toluene) 421, 515, 550, 591, 648 nm.

Zinc(II)-5,10,15,20-Tetrakis[m-(S-acetylthiomethyl) phenyl]porphyrin (Zn-29)

A mixture of 16.2 mg of 29 (16.7 μmol) in 20 mL of CHCl$_3$ and a solution of 80.0 mg of Zn(OAc)$_2$.2H$_2$O (365 μmol) in 5 mL of methanol were combined and stirred at ambient temperature. After 2 h the metalation was completed (checked by fluorescence excitation spectroscopy) and 40 mL of H$_2$O was added. The phases were separated and the organic layer was washed three times with 5% NaHCO$_3$ and dried (Na$_2$SO$_4$). The solvents were removed under reduced pressure. Column chromatography over flash silica gel with CH$_2$Cl$_2$/hexanes (4:1) gave the title compound as a purple solid in quantitative yield. IR (neat): ν=2922 (w, CH), 2849 (w, CH), 1690 (s, CO), 1655 (m, arom. C=C), 1600 (w, arom. C=C), 1478 (w), 1420(w), 1338 (w), 1208(m), 1131 (m), 1067(w), 1002(m), 955 (w), 932 (w), 794 (m), 717 (m); $^1$H NMR (300.5 MHz, CDCl$_3$): δ=2.30 (s, 12H, CH$_3$), 4.31 (s, 8H, CH$_2$), 7.62–7.69 (m, 8H, ArH), 8.05–8.13 (m, 8H, ArH), 8.92 (s, 8H, β-pyrrole); LD-MS calcd av mass 1028.15 (C$_{56}$H$_{44}$N$_4$O$_4$S$_4$Zn), obsd 1028.8, 986.6 [M$^+$-COCH$_3$], 954 . [M$^+$-SCOCH$_3$], 911.3 [M$^+$-SCOCH$_3$-COCH$_3$], 880.4 [M$^+$-2 SCOCH$_3$], 838.8 [M$^+$-2 SCOCH$_3$-COCH$_3$], 805.3 [M$^+$-3 SCOCH$_3$]; λ$_{abs}$ (toluene) 424, 550, 589 nm; λ$_{em}$ (toluene) 597, 647 nm.

Cobalt(II)-5,10,15,20-Tetrakis[m-(S-acetylthiomethyl) phenyl]porphyrin (Co-29)

A mixture of 14.2 mg of 29 (14.7 µmol) in 20 mL of CHCl$_3$ and a solution of 60.0 mg of Co(OAc)$_2$.4H$_2$O (339 µmol) in 5 mL of methanol were combined and stirred at ambient temperature. After 5 h an additional 261.0 mg of Co(OAc)$_2$.4H$_2$O (1.5 mmol) was added because there was still free base porphyrin left. Stirring at room temperature was continued. After 20 h the metalation was completed (checked by fluorescence excitation spectroscopy) and 30 mL of H$_2$O was added. The phases were separated and the organic layer was washed three times with 5% NaHCO$_3$ and dried (Na$_2$SO$_4$). The solvents were removed under reduced pressure. Column chromatography over flash silica gel with CH$_2$Cl$_2$/hexanes (5:1) gave the title compound as an orange-purple solid in quantitative yield. IR (neat): ν=3037 (w, arom. CH), 2955 (w, CH), 2924 (m, CH), 2849 (w, CH), 1725 (w), 1693 (s, CO), 1601 (w, arom. C=C), 1455 (w), 1422 (w), 1350 (m), 1131 (m), 1003 (m), 957 (w), 796 (m), 714 (m); LD-MS calcd av mass 1023.16 (C$_{56}$H$_{44}$N$_4$O$_4$S$_4$Co), obsd 1023.4, 980.3 [M$^+$-COCH$_3$], 948.3 [M$^+$-SCOCH$_3$], 875.2 [M$^+$-2 SCOCH$_3$]; $\lambda_{abs}$ (toluene) 414, 529 nm.

Example 2

Setting and Reading the State of a Porphyrinic Macrocycle

I. Preparation of Gold Electrodes, Formation of Electrochemical Cell Deposition of Thiol-porphyrin Monolayer Glass slides were soaked in 90° C. piranha solution for thirty minutes, thoroughly rinsed with doubly distilled water, and dried under vacuum. A 1 nm layer of chromium was evaporated onto the glass, followed by 100 nm of gold through a thin mask consisting of four parallel lines, each with a width of approximately 75 microns, spaced at approximately 1 mm intervals. All depositions were done at 10$^{-6}$ torr using an E-beam evaporator.

Immediately after venting of the vacuum system, the slides were removed and stored under dry ethanol until use. The slides were dried with a stream of nitrogen and a piece of PDMS with a 3 mm diameter hole in the center was immediately placed over all four gold electrodes and filled with a porphyrin solution (0.1 mg per milliliter in dry ethanol) (Z15 from example 1).

Figure 23:
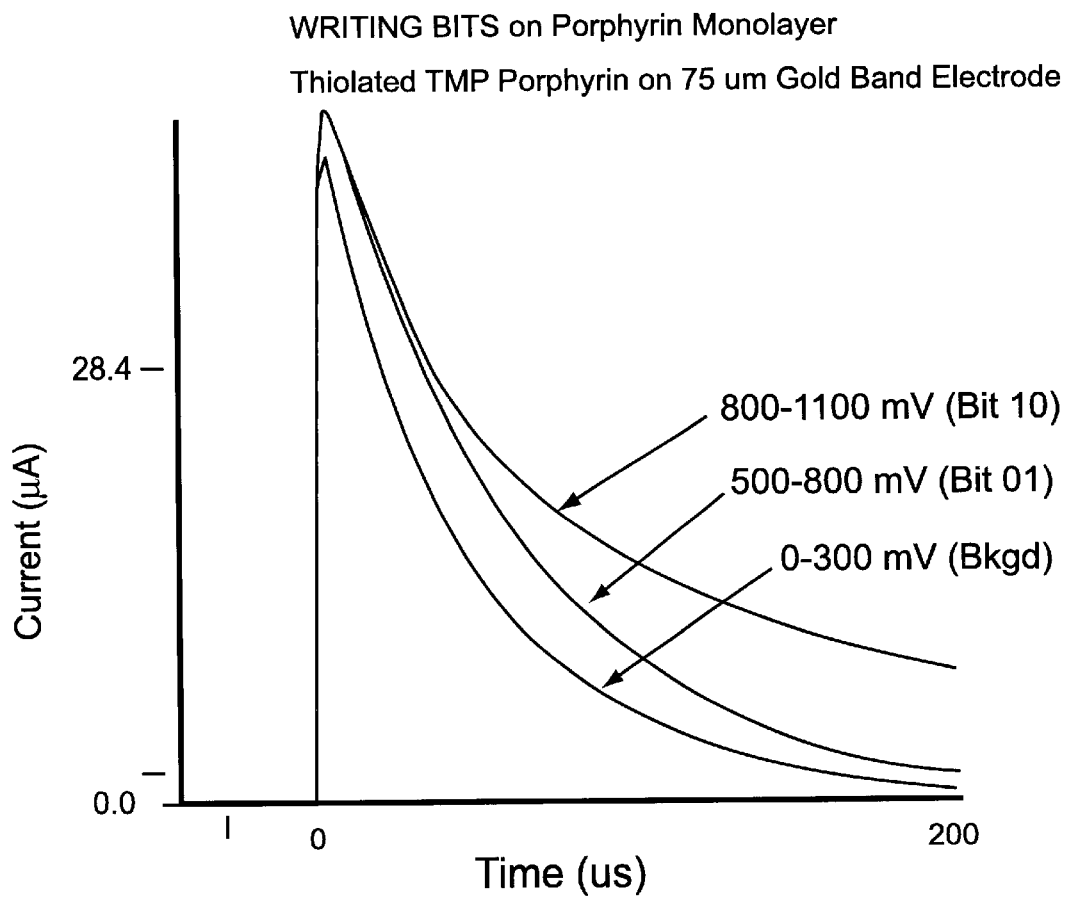
FIG. 23 illustrates the writing of bits on a porphyrin monolayer having two non-neutral oxidation states. A plot of current versus time at 3 applied voltages is illustrated. At 0–300 mV, no bit is set and the plot provides a background signal. At 500–800 mV and at 800–1100 mV the first and second bits are written, respectively.

The slide was then sonicated at room temperature for 15 minutes which was found to facilitate monolayer formation. After sonication, the PDMS mask was removed and the slide was rinsed with dry ethanol. A new PDMS mask was prepared by casting a 10:1 ratio solution of monomer to catalyst into a mold consisting of a pyramidal channel with a 40 µm by 1 cm base width. This new mask was placed on top of the porphyrin-covered electrodes to form the electrochemical cell. The channel was filled with 1.0 M TBAP, and a silver wire reference electrode was used to complete the electrical circuit. This creates four identical porphyrin-covered gold electrodes with 40 by 75 micron dimensions, each of which is individually addressable using a common backplane reference electrode. The porphyrin monolayer was then analyzed with cyclic voltammetry to establish that the porphyrin had bound to the gold substrate and to establish the extent of coverage of the monolayer on the gold surface (FIG. 23).

II. Reading and Writing Porphyrin Bits

A labview program was written to apply a potential pulse (the pulse was applied to the reference electrode, since the working electrode was maintained at ground potential). Thus, the potential was inverted and applied to the reference electrode. The waveform was generated at 5 MHz and applied to a bare silver wire reference electrode. The current response was monitored through the gold working electrode. The reference electrode was poised at a constant DC potential using a home built potentiostat that also amplifies the resulting current.

In order to write a bit into the porphyrin monolayer, it was necessary to apply the appropriate potential to create the appropriate oxidation state of the porphyrin. The reference electrode was poised at three DC potentials while the working electrode was held at zero potential, in order to probe the response at the neutral and at both non-neutral oxidation states of the porphyrin (FIG. 23). A 0–300 mV potential pulse was applied below the first oxidation potential to record the background charging current. At 300 mV, there was no redox process occurring, thus, only the background charging current was observed. The electrode was then set at 500 mV DC and an identical 300 mV potential pulse was applied raising the potential to 800 mV and thereby eliciting the first oxidation of the porphyrin.

This current response was the sum of the faradaic current superimposed on the background charging current. Because the background was constant, the first response could be subtracted from the latter and the remainder was the faradaic current.

A second potential step was applied from 800–1100 mV. This step oxidized the porphyrin into the second oxidation state and produced a second increment of faradaic current which again was background subtracted. The background subtracted currents had approximately equal magnitude because each corresponded to a one electron processes in the same molecule(s) immobilized to the electrode surface. The amplified signal was acquired at 5 MHz giving a time resolution of 200 ns per data point which was sufficient to detect the roughly 70 µs transient response. The background-subtracted instantaneous current was integrated to produce a plot of the instantaneous charge as a function of time (FIG. 23).

Figure 24:
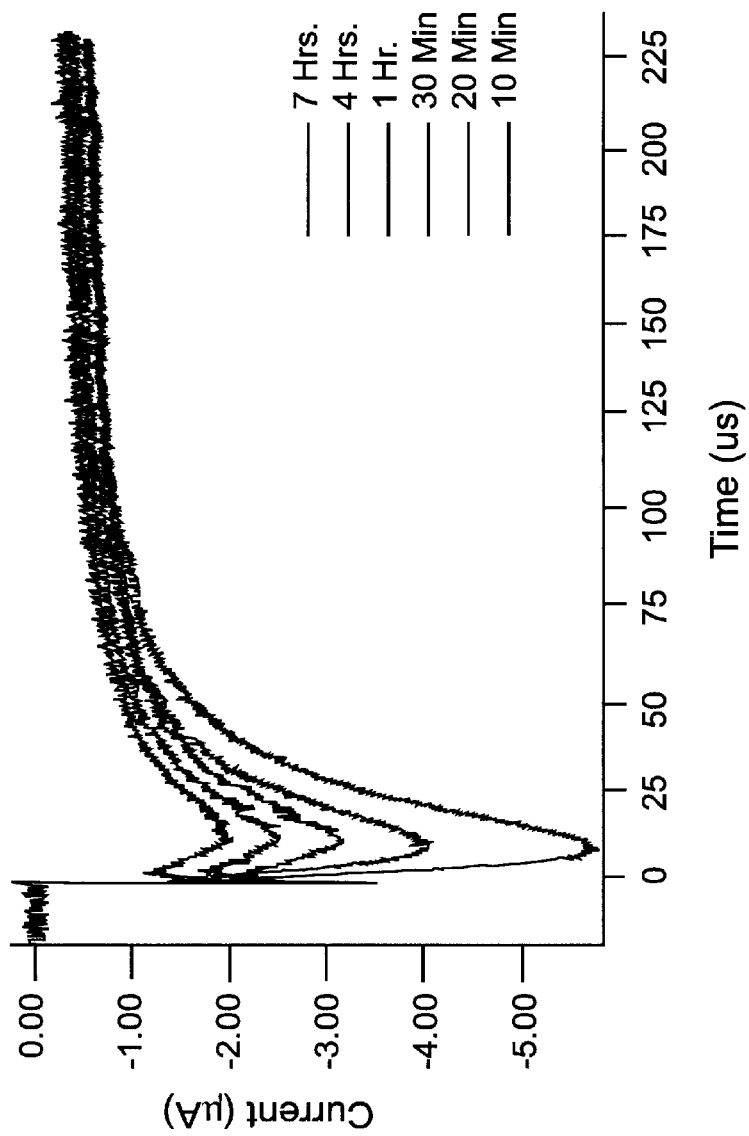
FIG. 24 illustrates the read/write of a monomeric porphyrin. Current is plotted as a function of potential.
Figure 25:
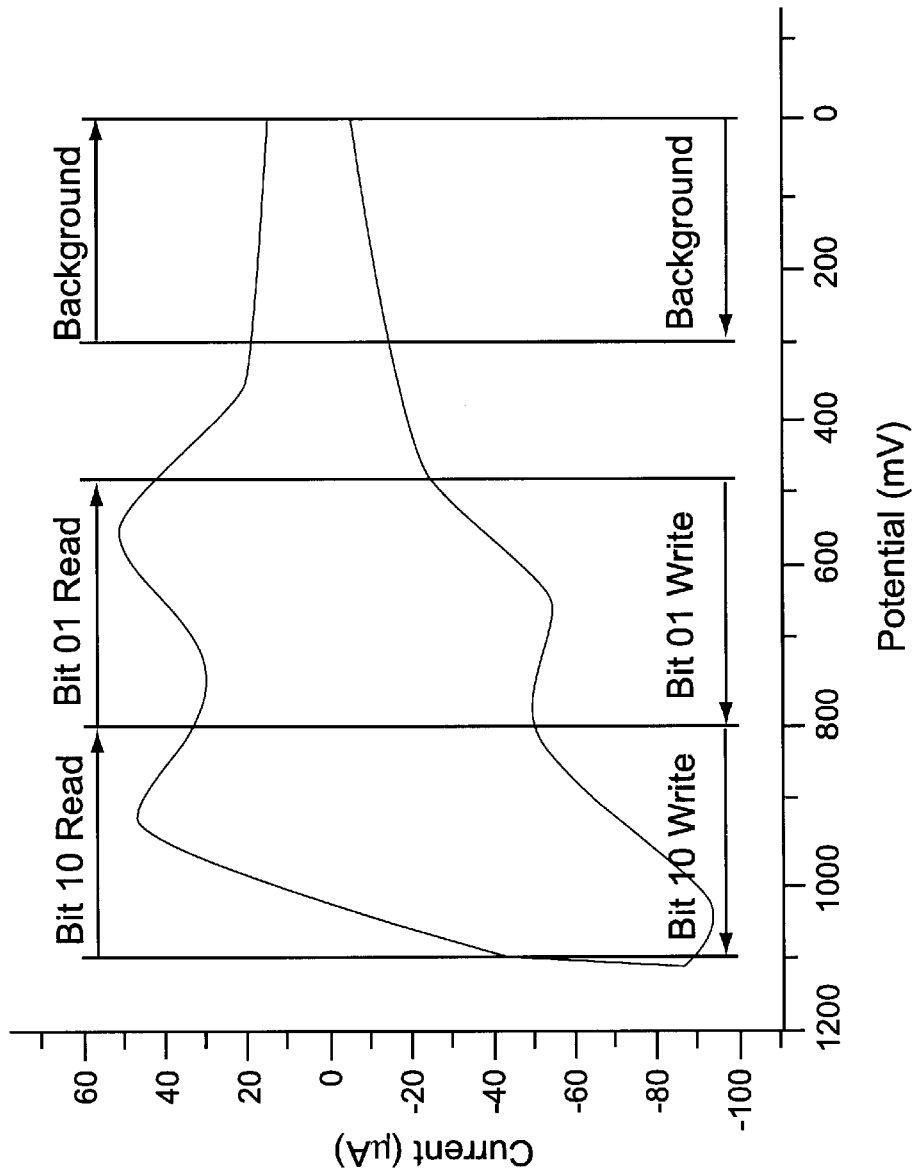
FIG. 25 illustrates background-subtracted faradaic read current.

Once the porphyrin was set at a given oxidation state, it could be read by applying the appropriate negative potential step. For example, the higher bit could be read simply by stepping between 1100–800 mV. The lower bit could be read by stepping between 800–500 mV. The charging current could be determined by stepping between 300–0 mV. Again, the background was subtracted from each step to determine the background-subtracted read current (FIG. 25). The read/write cycles are illustrated in FIG. 24.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An apparatus for storing data, said apparatus comprising:
   a fixed electrode electrically coupled to
   a storage medium having a multiplicity of different and distinguishable oxidation states wherein data is stored in said oxidation states by the addition or withdrawal of one or more electrons from said storage medium via the electrically coupled electrode, wherein said storage medium comprises a molecule selected from the group consisting of a porphyrinic macrocycle, a metallocene, a linear polyene, a cyclic polyene, a heteroatom-substituted linear polyene, a heteroatom-substituted cyclic polyene, a tetrathiafalvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, and a peri-bridged naphthalene dichalcogenide.

2. The apparatus of claim 1, wherein said storage medium stores data at a density of at least one bit per molecule.

3. The apparatus of claim 1, wherein said storage medium comprises a molecule having at least two different and distinguishable oxidation states.

4. The apparatus of claim 1, wherein said storage medium comprises a molecule having at least eight different and distinguishable oxidation states.

5. The apparatus of claim 1, wherein said storage medium is covalently linked to said electrode.

6. The apparatus of claim 1, wherein said storage medium is electrically coupled to said electrode through a linker.

7. The apparatus of claim 1, wherein said storage medium is juxtaposed in the proximity of said electrode such that electrons can pass from said storage medium to said electrode.

8. The apparatus of claim 1, wherein said storage medium is juxtaposed to a dielectric material imbedded with counterions.

9. The apparatus of claim 1, wherein said storage medium and said electrode are fully encapsulated in an integrated circuit.

10. The apparatus of claim 1, wherein said storage medium is electronically coupled to a second electrode that is a reference electrode.

11. The apparatus of claim 1, wherein said storage medium is present on a single plane in said device.

12. The apparatus of claim 1, wherein said device refreshes the oxidation state of said storage medium after reading said oxidation state.

13. The apparatus of claim 1, wherein said storage medium is covalently linked to said electrode through a linker.

14. The apparatus of claim 13, wherein said linker is a thiol linker.

15. The apparatus of claim 1, wherein said storage medium is present at a multiplicity of storage locations.

16. The apparatus of claim 15, wherein said storage locations are present on a single plane in said device.

17. The apparatus of claim 15, wherein said apparatus comprises multiple planes and said storage locations are present on multiple planes of said device.

18. The apparatus of claim 15, wherein said storage locations range from about 1024 to about 4096 different locations.

19. The apparatus of claims 18, wherein each location is addressed by a single electrode.

20. The apparatus of claim 18, wherein each location is addressed by two electrodes.

21. The apparatus of claim 1, wherein said electrode is connected to a voltage source.

22. The apparatus of claim 21, wherein said voltage source is the output of an integrated circuit.

23. The apparatus of claim 1, wherein said electrode is connected to a device to read the oxidation state of said storage medium.

24. The apparatus of claim 23, wherein said device provides a Fourier transform of the output signal from said electrode.

25. The apparatus of claim 23, wherein said device refreshes the oxidation state of said storage medium after reading said oxidation state.

26. The apparatus of claim 23, wherein said device is selected from the group consisting of a voltammetric device, an amperometric device, and a potentiometric device.

27. The apparatus of claim 26, wherein said device is an impedance spectrometer or a sinusoidal voltammeter.

28. The apparatus of claim 1, wherein said storage medium comprises a molecule selected from the group consisting of a porphyrin, an expanded porphyrin, a contracted porphyrin, a ferrocene, a linear porphyrin polymer, and a porphyrin array.

29. The apparatus of claim 28, wherein said storage medium comprises a porphyrinic macrocycle substituted at a β-position or at a meso-position.

30. The apparatus of claim 28, wherein said storage medium comprises a molecule having five different and distinguishable oxidation states.

31. The apparatus of claim 30, wherein said molecule has the formula:

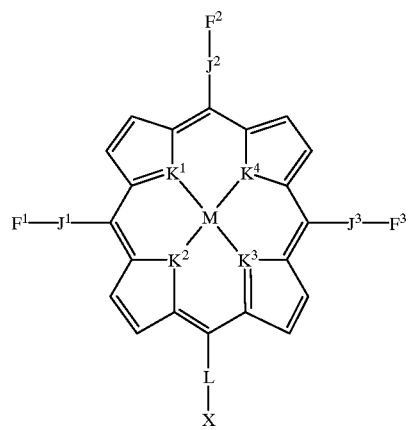

wherein
M$^1$ is a metal;
F$^1$, F$^2$, and F$^3$ are independently selected ferrocenes or substituted ferrocenes;
j$^1$, J$^2$, and J$^3$ are independently selected linkers;
K$^1$, K$^2$, K$^3$ and K$^4$ are independently selected from the group consisting of N, O, S, Se, Te, and CH;
L is a linker; and
X is selected from the group consisting of a substrate, a reactive site that can covalently couple to a substrate, and a reactive site that can ionically couple to a substrate.

32. The apparatus of claim 31, wherein
K$^1$, K$^2$, K$^3$ and K$^4$ are the same;

$M^1$ is a metal selected from the group consisting of Zn, Mg, Cd, Hg, Cu, Ag, Au, Ni, Pd, Pt, Co, Rh, Ir, Mn, B, Pb, Al, Ga, and Sn;

$J^2$, $J^2$, and $J^3$ are the same; and $F^1$, $F^2$, and $F^3$ are all different.

33. The apparatus of claim 32, wherein said molecule is

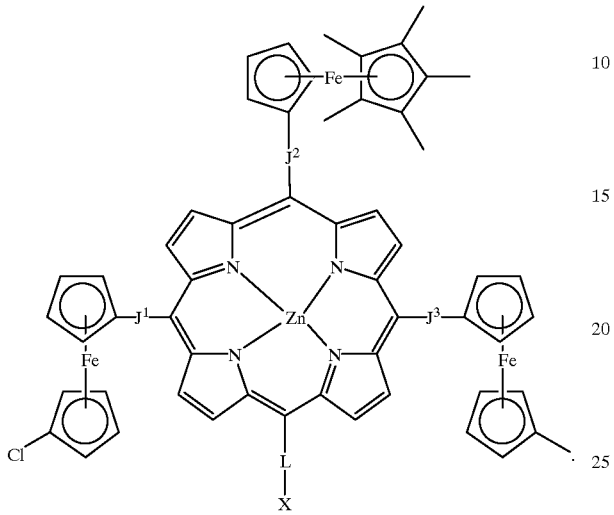

34. The appartus of claim 28, wherein said storage medium comprises a molecule having three different and distinguishable oxidation states.

35. The apparatus of claim 34, wherein said molecule has the formula:

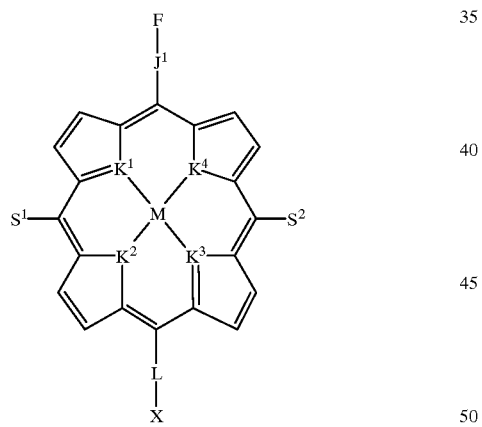

wherein

F is selected from the group consisting of a ferrocene, a substituted ferrocene, a metalloporphyrin, and a metallochlorin;

$J^1$ is a linker;

M is a metal;

$S^1$ and $S^2$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts $K^1$, $K^2$, $K^3$, and $K^4$ are independently selected from the group consisting of N, S, O, Se, Te, and CH;

L is a linker; and and X is selected from the group consisting of a substrate, a reactive site that can covalently couple to a substrate, and a reactive site that can ionically couple to a substrate;

and said molecule has at least three different and distinguishable oxidation states.

36. The apparatus of claim 35, wherein $J^1$, $J^2$, and $J^3$ are selected from the group consisting of 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, and 4,4"-terphenyl.

37. The apparatus of claim 35, wherein said molecule has the formula:

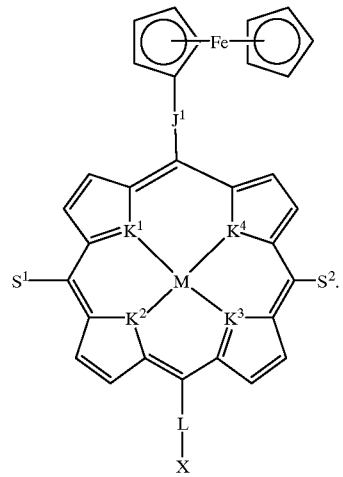

38. The apparatus of claim 37, wherein said molecule is

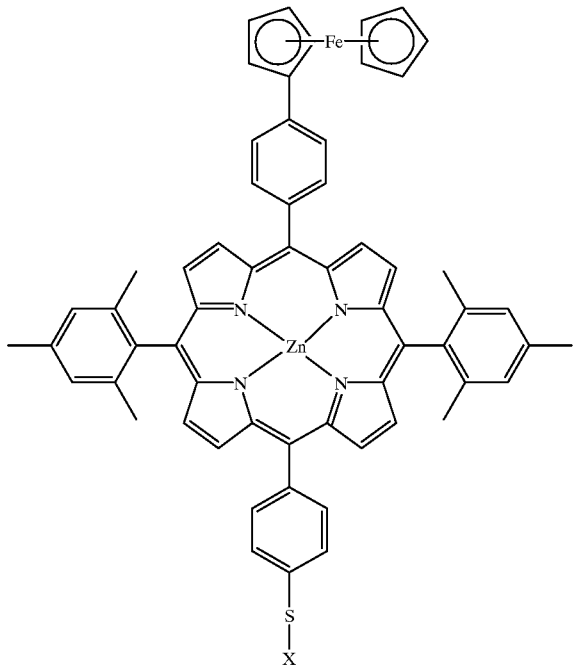

39. The apparatus of claim 35, wherein said molecule has the formula:

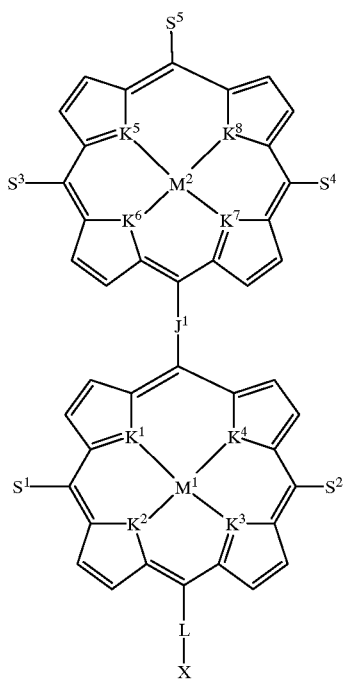

wherein
M² is a metal;
K⁵, K⁶, K⁷, and K⁸ are independently selected from the group consisting of N, S, O, Se, Te, and CH;
S³, S⁴, and S⁵ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts; and
L—X is selected from the group consisting of 4-(2-(4-mercaptophenyl)ethynyl)phenyl, 4-mercaptomethylphenyl, 4-hydroselenophenyl, 4-(2-(4-hydroselenophenyl)ethynyl)phenyl, 4-hydrotellurophenyl, and 4-(2-(4-hydrotellurophenyl)ethynyl)phenyl.

40. The apparatus of claim 39, wherein said molecule is

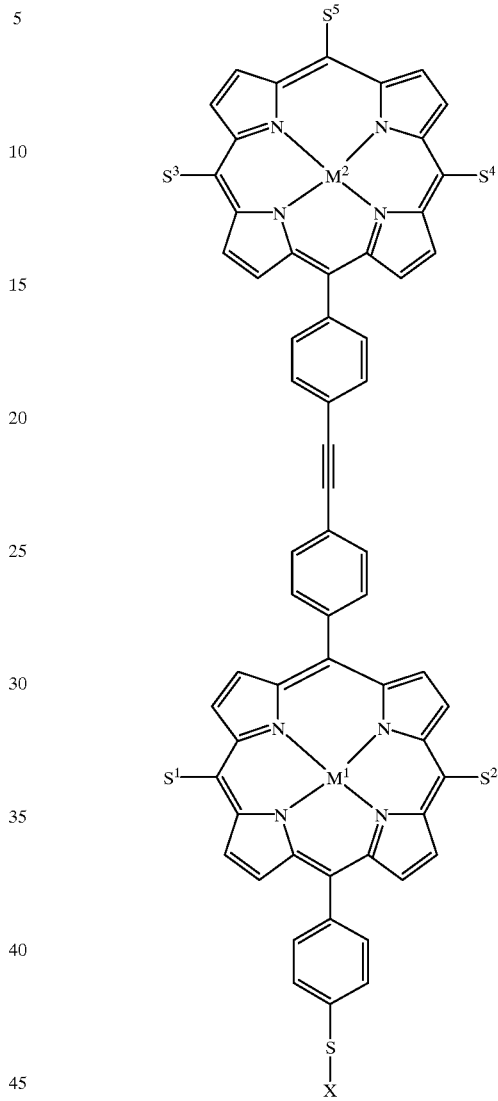

41. The apparatus of claim 35, wherein said molecule has the formula:

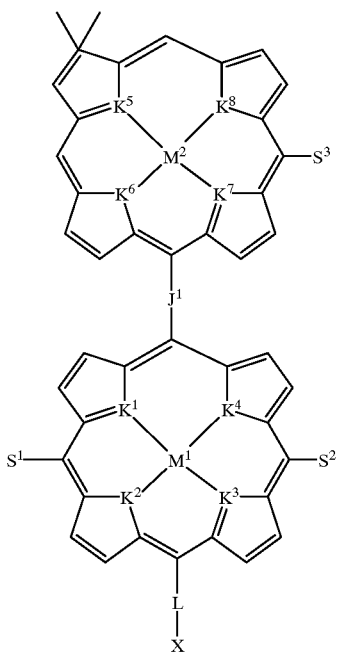

wherein $M^2$ is a metal;

$K^5$, $K^6$, $K^7$, and $K^8$ are independently selected from the group consisting of N, O, S, Se, Te, and CH;

$S^3$ is selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts and L—X is selected from the group consisting of 4-(2-(4-mercaptophenyl)ethynyl)phenyl, 4-mercaptomethylphenyl, 4-hydroselenophenyl, 4-(2-(4-hydroselenophenyl)ethynyl)phenyl, 4-hydrotellurophenyl, and 4-(2-(4-hydrotellurophenyl) ethynyl)phenyl.

42. The apparatus of claim 41, wherein said molecule is

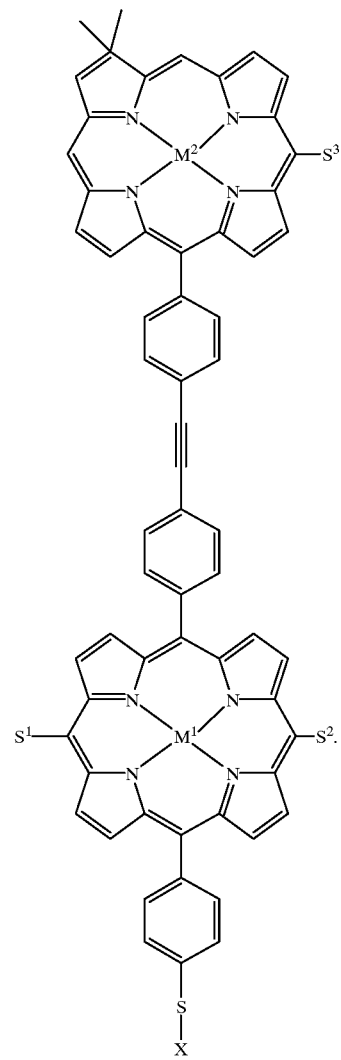

43. A method of storing data, said method comprising:
 i) providing an apparatus according to claim 1; and
 ii) applying a voltage to said electrode at sufficient current to set an oxidation state of said storage medium.

44. The method of claim 43, wherein said voltage ranges up to about 2 volts.

45. The method of claim 43, wherein said voltage is the output of an integrated circuit.

46. The method of claim 43, wherein said voltage is the output of a logic gate.

47. The method of claim 43, wherein said storage medium comprises a molecule selected from the group consisting of a porphyrin, an expanded porphyrin, a contracted porphyrin, a ferrocene, a linear porphyrin polymer, and a porphyrin array.

48. The method of claim 43, wherein said storage medium comprises a porphyrinic macrocycle substituted at a β-position or at a meso-position.

49. The method of claim 43, further comprising detecting the oxidation state of said storage medium and thereby reading out the data stored therein.

50. The method of claim 49, wherein said detecting the oxidation state of the storage medium further comprises refreshing the oxidation state of the storage medium.

51. The method of claim 49, wherein said detecting comprises analyzing a readout signal in the time domain.

52. The method of claim 49, wherein said detecting utilizes a voltammetric method.

53. The method of claim 49, wherein said detecting utilizes impedance spectroscopy.

54. The method of claim 49, wherein said detecting comprises exposing said storage medium to an electric field to produce an electric field oscillation having characteristic frequency and detecting said characteristic frequency.

55. The method of claim 49, wherein said detecting comprises analyzing a readout signal in the frequency domain.

56. The method of claim 55, wherein said detecting comprises performing a Fourier transform on said readout signal.

57. An information storage medium, said storage medium comprising one or more storage molecules such that said storage medium has at least two different and distinguishable non-neutral oxidation states, wherein said one or more storage molecules are independently selected from the group consisting of a a porphyrinic macrocycle, a metallocene, a linear polyene, a cyclic polyene, a heteroatom-substituted linear polyene, a heteroatom-substituted cyclic polyene, a tetrathiafulvalene, a tetraselenafalvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, and a peri-bridged naphthalene dichalcogenide.

58. The storage medium of claim 57, wherein said storage medium comprises a storage molecule selected from the group consisting of a porphyrin, an expanded porphyrin, a contracted porphyrin, a ferrocene, a linear porphyrin polymer, and a porphyrin array.

59. The storage medium of claim 58, comprising a storage molecule that contains two or more covalently linked redox-active subunits.

60. the storage medium of claim 58, wherein said storage molecule has three different and distinguishable non-neutral oxidation states.

61. The storage medium of claim 60, wherein said storage molecule has the formula:

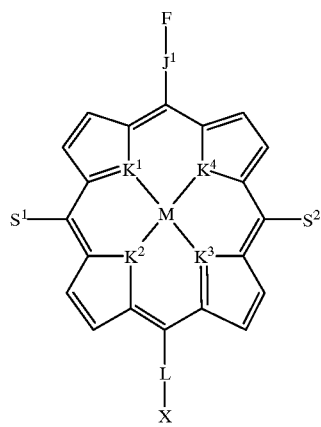

wherein
- $F^1$ is selected from the group consisting of a ferrocene, a substituted ferrocene, a metalloporphyrin, and a metallochlorin;
- $J^1$ is a linker;
- $M^1$ is a metal;
- $S^1$ and $S^2$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts;
- $K^1$, $K^2$, $K^3$, and $K^4$ are independently selected from the group consisting of N, O, S, Se, Te, and CH;
- L is a linker; and
- X is selected from the group consisting of a substrate, a reactive site that can covalently couple to a substrate, and a reactive site that can ionically couple to a substrate, and said molecule has at least three different and distinguishable oxidation states.

62. The storage medium of claim 61, wherein said storage molecule has the formula:

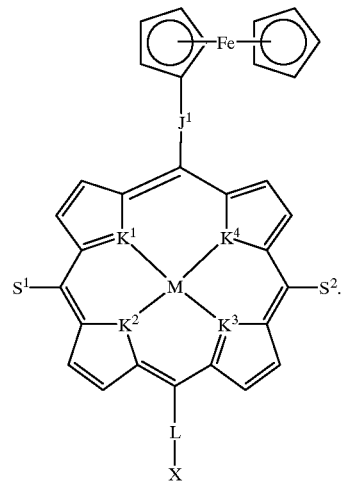

63. The storage medium of claim 62, wherein said storage molecule has the formula:

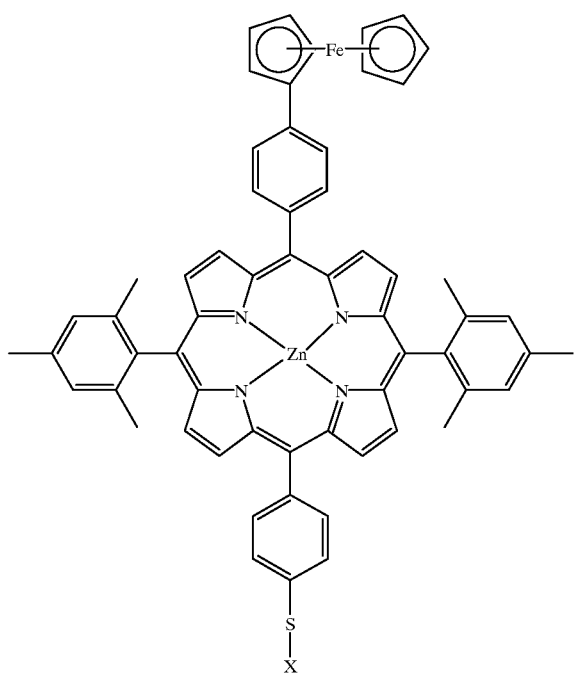

64. The storage medium of claim 61, wherein said storage molecule has the formula:

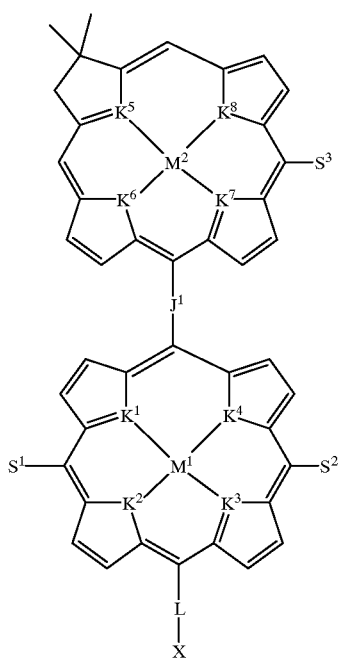

wherein $M^2$ is a metal;

$K^5$, $K^6$, $K^7$, and $K^8$ are independently selected from the group consisting of N, O, S, Se, Te, and CH;

$S^3$ is selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts.

65. The storage medium of claim 64, wherein said storage molecule has the formula:

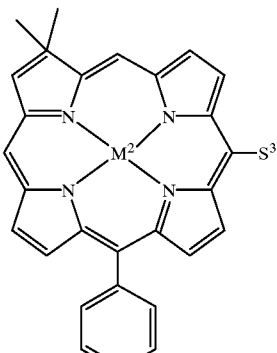

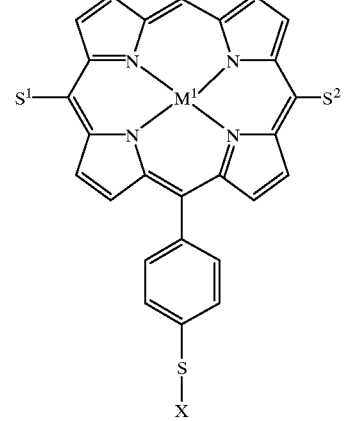

66. The storage medium of claim 61, wherein said storage molecule has the formula:

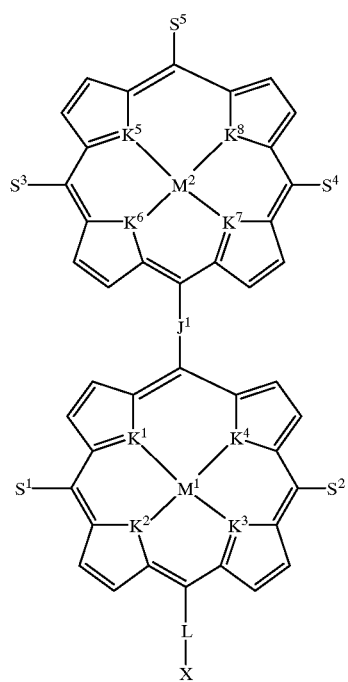

wherein $M^2$ is a metal;

$K^5$, $K^6$, $K^7$, and $K^8$ are independently selected from the group consisting of N, O, S, Se, Te, and CH;

$S^3$, $S^4$, and $S^5$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts.

67. The storage medium of claim 66, wherein said storage molecule has the formula:

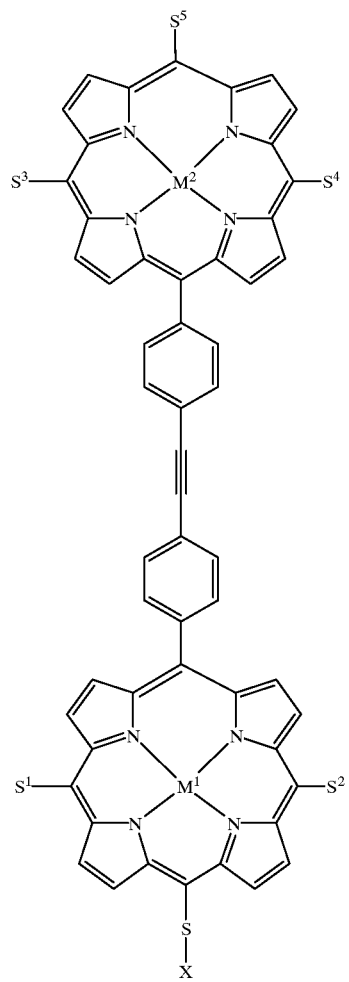

68. The storage medium of claim 58, wherein said storage molecule has five different and distinguishable non-neutral oxidation states.

69. The storage medium of claim 68, wherein said storage molecule has the formula:

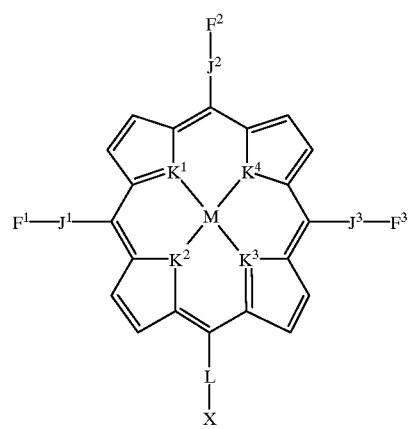

wherein

M is a metal;

$F^1$, $F^2$, and $F^3$ are independently selected ferrocenes or substituted ferrocenes;

$J^1$, $J^2$, and $J^3$ are independently selected linkers;

$K^1$, $K^2$, $K^3$, and $K^4$ are independently selected from the group consisting of N, O, S, Se, Te, and CH;

L is a linker; and

X is selected from the group consisting of a substrate, a reactive site that can covalently couple to a substrate, and a reactive site that can ionically couple to a substrate.

70. The storage medium of claim 69, wherein $J^1$, $J^2$, and $J^3$ are selected from the group consisting of 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, and 4,4"-terphenyl.

71. The storage medium of claim 69, wherein $K^1$, $K^2$, $K^3$ and $K^4$ are the same;

M is a metal selected from the group consisting of Zn, Mg, Cd, Hg, Cu, Ag, Au, Ni, Pd, Pt, Co, Rh, Ir, Mn, B, Al, Pb, Ga, and Sn;

$J^1$, $J^2$, and $J^3$ are the same; and $F^1$, $F^2$, and $F^3$ are all different.

72. The storage medium of claim 71, wherein said molecule is

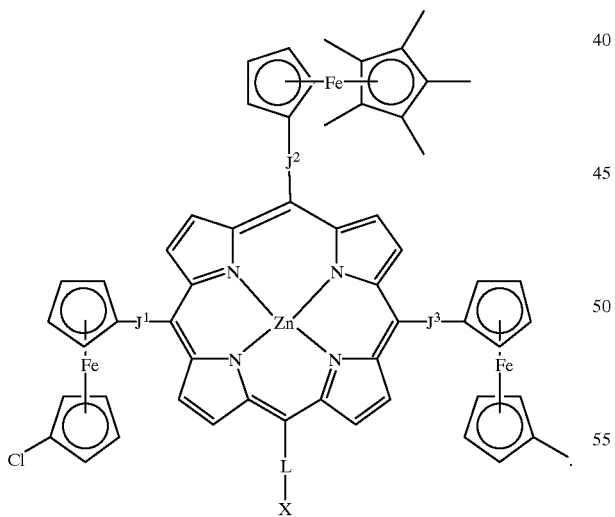

73. A molecule for the storage of information, said molecule having the formula:

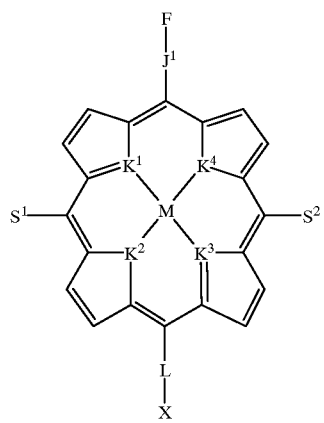

$F^1$ is selected from the group consisting of a ferrocene, a substituted ferrocene, a metalloporphyrin, and a metallochlorin;

$J^1$ is a linker;

M is a metal;

$S^1$ and $S^2$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts;

$K^1$, $K^2$, $K^3$, and $K^4$ are independently selected from the group consisting of N, O, S, Se, Te, and CH;

L is a linker; and

X is selected from the group consisting of a substrate, a reactive site that can covalently couple to a substrate, and a reactive site that can ionically couple to a substrate, and said molecule has at least three different and distinguishable oxidation states.

74. The molecule of claim 73, wherein said molecule has the formula:

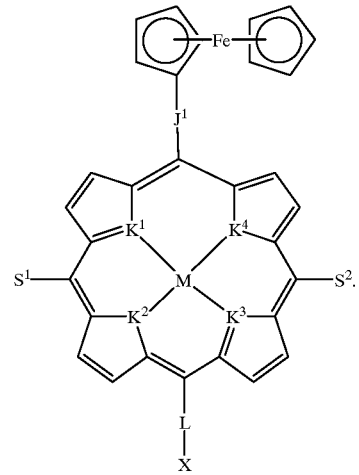

75. The molecule of claim 73, wherein said molecule is

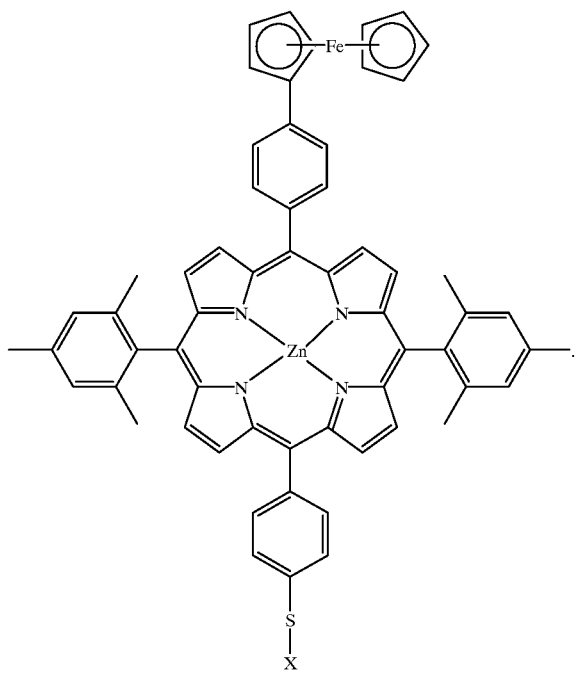

76. The molecule of claim 73, wherein said molecule has the formula:

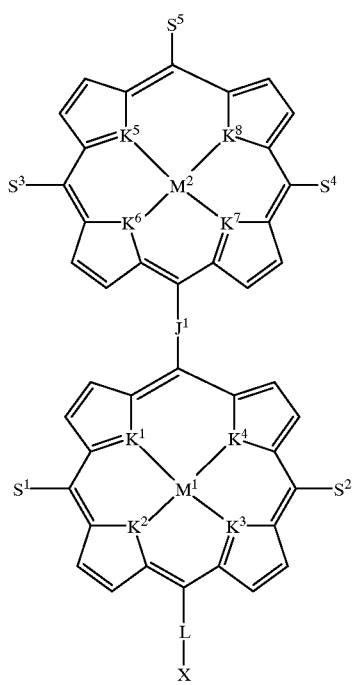

wherein
M² is a metal;

$K^5$, $K^6$, $K^7$, and $K^8$ are independently selected from the group consisting of N, S, O, Se, Te, and CH;

$S^3$, $S^4$, and $S^5$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts; and L—X is selected from the group consisting of 4-(2-(4-mercaptophenyl)ethynyl)phenyl, 4-mercaptomethylphenyl, 4-hydroselenophenyl, 4-(2-(4-hydroselenophenyl)ethynyl)phenyl, 4-hydrotellurophenyl, and 4-(2-(4-hydrotellurophenyl)ethynyl)phenyl.

77. The apparatus of claim 76, wherein said molecule is

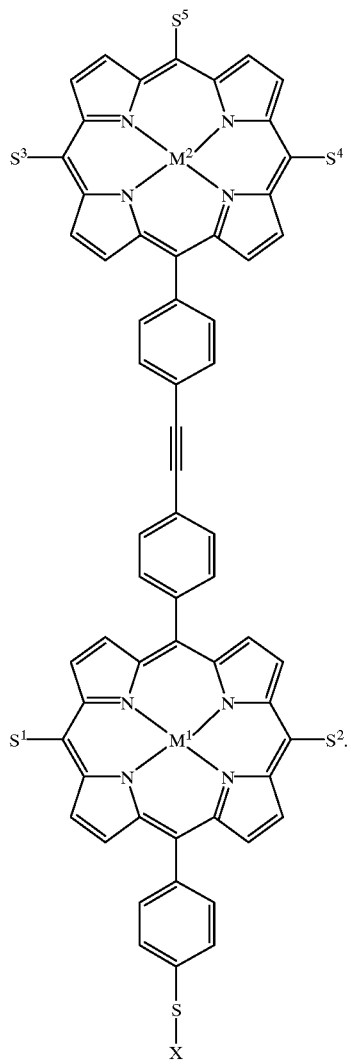

78. The molecule of claim 73, wherein said molecule has the formula:

79. The apparatus of claim 78, wherein said molecule is

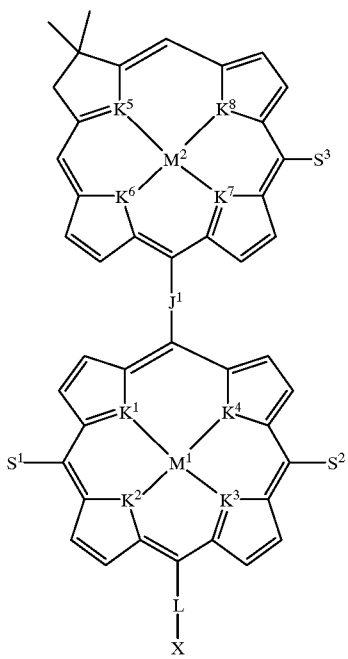

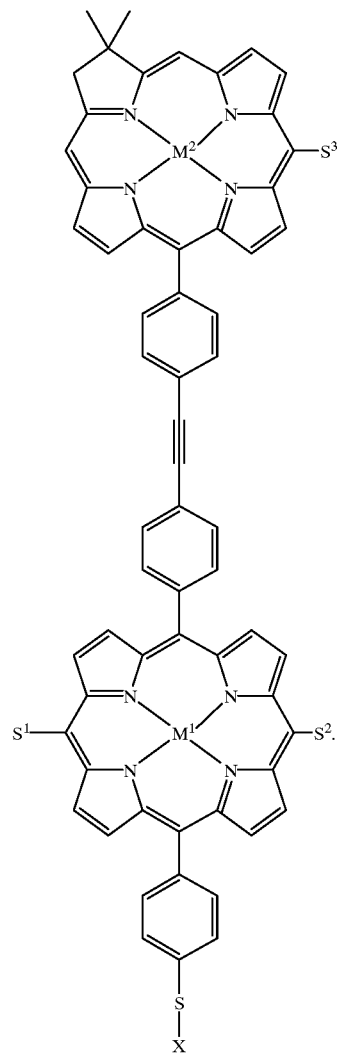

wherein $M^2$ is a metal;

$K^5$, $K^6$, $K^7$, and $K^8$ are independently selected from the group consisting of N, O, S, Se, Te, and CH;

$S^3$ is selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts and L—X is selected from the group consisting of 4-(2-(4-mercaptophenyl)ethynyl)phenyl, 4-mercaptomethylphenyl, 4-hydroselenophenyl, 4-(2-(4-hydroselenophenyl)ethynyl)phenyl, 4-hydrotellurophenyl, and 4-(2-(4-hydrotellurophenyl) ethynyl)phenyl.

80. An apparatus for storing data, said apparatus comprising:
  a fixed electrode electrically coupled to
  a storage medium having a multiplicity of different and distinguishable oxidation states wherein data is stored in said oxidation states by the addition or withdrawal of one or more electrons from said storage medium via the electrically coupled electrode, wherein said storage medium is present at a multiplicity of storage locations and said storage locations range from about 1024 to about 4096 different locations.

81. The apparatus of claim 80, wherein each location is addressed by a single electrode.

82. The apparatus of claim 80, wherein each location is addressed by two electrodes.

83. The apparatus of claim 80, wherein said different and distinguishable oxidation states of said storage medium can be set by a voltage difference no greater than about 2 volts.

84. The apparatus of claim 80, wherein said electrode is connected to a voltage source.

85. The apparatus of claim 84, wherein said voltage source is the output of an integrated circuit.

86. The apparatus of claim 80, wherein, wherein said storage medium comprises a molecule selected from the group consisting of a porphyrinic macrocycle, a metallocene, a linear polyene, a cyclic polyene, a heteroatom-substituted linear polyene, a heteroatom-substituted cyclic polyene, a tetrathiafalvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, and a peri-bridged naphthalene dichalcogenide.

87. The apparatus of claim 86, wherein said storage medium comprises a molecule selected from the group consisting of a porphyrin, an expanded porphyrin, a contracted porphyrin, a ferrocene, a linear porphyrin polymer, and a porphyrin array.

88. The apparatus of claim 87, wherein said storage medium comprises a porphyrinic macrocycle substituted at a β-position or at a meso-position.

89. The apparatus of claim 80, wherein said electrode is connected to a device to read the oxidation state of said storage medium.

90. The apparatus of claim 89, wherein said device refreshes the oxidation state of said storage medium after reading said oxidation state.

91. The apparatus of claim 89, wherein said device is selected from the group consisting of a voltammetric device, an amperometric device, and a potentiometric device.

92. The apparatus of claim 91, wherein said device is an impedance spectrometer or a sinusoidal voltammeter.

93. The apparatus of claim 92, wherein said device provides a Fourier transform of the output signal from said electrode.

* * * * *